(12) United States Patent
Ikeya et al.

(10) Patent No.: US 8,088,916 B2
(45) Date of Patent: *Jan. 3, 2012

(54) HYALURONIC ACID-METHOTREXATE CONJUGATE

(75) Inventors: Hitoshi Ikeya, Machida (JP); Tadashi Morikawa, Machida (JP); Koichi Takahashi, Machida (JP); Tatsuya Tamura, Gotenba (JP); Akira Okamachi, Susono (JP); Takenori Ishizawa, Gotenba (JP); Haruhiko Sato, Gotenba (JP); Yoshinobu Higuchi, Gotenba (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 1520 days.

This patent is subject to a terminal disclaimer.

(21) Appl. No.: 10/591,653

(22) PCT Filed: Mar. 4, 2005

(86) PCT No.: PCT/JP2005/003739
§ 371 (c)(1),
(2), (4) Date: Sep. 5, 2006

(87) PCT Pub. No.: WO2005/085294
PCT Pub. Date: Sep. 15, 2005

(65) Prior Publication Data
US 2007/0197465 A1    Aug. 23, 2007

(30) Foreign Application Priority Data

Mar. 5, 2004   (JP) .................................. 2004-062616
Jun. 4, 2004   (JP) .................................. 2004-167755

(51) Int. Cl.
C08B 37/00   (2006.01)
A01N 43/04   (2006.01)
A01N 43/60   (2006.01)

(52) U.S. Cl. .............................. 536/53; 514/54; 514/251

(58) Field of Classification Search ................ 514/2, 54, 514/249, 251; 530/300, 322; 536/123.1, 536/53; 544/260
See application file for complete search history.

(56) References Cited

U.S. PATENT DOCUMENTS

| 4,489,065 | A |   | 12/1984 | Walton |        |
|-----------|---|---|---------|--------|--------|
| 5,688,931 | A | * | 11/1997 | Nogusa et al. | 536/20 |
| 5,902,795 | A |   | 5/1999  | Toole  |        |
| 6,197,326 | B1 |  | 3/2001  | Suzuki et al. | |
| 6,322,815 | B1 |  | 11/2001 | Saltzman | |
| 6,428,804 | B1 |  | 8/2002  | Suzuki et al. | |
| 7,807,675 | B2 | * | 10/2010 | Ikeya et al. | 514/249 |

FOREIGN PATENT DOCUMENTS

| EP | 0640622 A1 | 3/1995 |
| EP | 0 911 025 A1 | 4/1999 |
| EP | 1 082 963 A1 | 3/2001 |
| EP | 1 712 257 A1 | 10/2006 |
| EP | 1710257 A1 | 10/2006 |
| JP | 05-039306 | 2/1993 |
| JP | 8-507750 | 8/1996 |
| JP | 11-222425 | 8/1999 |
| JP | 2002-542304 | 12/2002 |
| WO | 92/11037 A2 | 7/1992 |
| WO | WO 94/13327 | 6/1994 |
| WO | WO 94/19376 | 9/1994 |
| WO | 95/34325 A1 | 12/1995 |
| WO | WO 99/59603 | 11/1999 |
| WO | WO 00/64486 | 11/2000 |
| WO | 01/68105 A1 | 9/2001 |
| WO | WO 02/44218 A1 | 6/2002 |
| WO | WO 2005/066214 A1 | 1/2005 |

OTHER PUBLICATIONS

Garnett, Advanced Drug Delivery Reviews vol. 53, Issue 2, Dec. 17, 2001, pp. 171-216.*

Andre Rosowsky, Ronald A. Forsch; James H. Freisheim; John Galivan and Michael Wick; Methotrexate Analogues. 23. Synthesis, Dihydrofolate Reductase Affinity, Cytotoxicity, and in Vivo Antitumor Activity of Some Putative Degradation Products of Methotrexate-Poly (L-lysine) Conjugates; J. Med. Chem. 1984, 27, 888-893.

Luo, Yi et al., "A Hyaluronic Acid-Taxol Antitumor Bioconjugate Targeted to Cancer Cells" Biomolecules, vol. 1, No. 2, 2000, pp. 208-218 XP002601147.

Ouchi, T. et al., "Chapter 8: Design of Polysaccharide-5-Fluorouracil Conjugates Exhibiting Antitumor Activities", American Chemical Society, Symposium Series, vol. 469, Polym. Drugs Drug Delivery System, 1991, pp. 71-83, XP008126996.

* cited by examiner

*Primary Examiner* — Nizal Chandrakumar
*Assistant Examiner* — David E Gallis
(74) *Attorney, Agent, or Firm* — Browdy and Neimark, PLLC

(57) ABSTRACT

An object of the present invention is to provide a hyaluronic acid-methotrexate conjugate useful as a therapeutic drug for joint diseases.

There is provided a hyaluronic acid-methotrexate conjugate useful as a therapeutic drug for joint diseases, wherein methotrexate is conjugated with a carboxyl group of hyaluronic acid through a linker containing a peptide chain consisting of 1 to 8 amino acids.

9 Claims, 5 Drawing Sheets

*P<0.0001 vs HA-MTX conjugate Mean+SEM

HYALURONIC ACID-METHOTREXATE CONJUGATE

TECHNICAL FIELD

The present invention relates to a hyaluronic acid-methotrexate conjugate and a pharmaceutical use thereof.

BACKGROUND ART

Osteoarthritis (hereinafter also referred to "OA") is one of so-called degenerative diseases which occur on the basis of aging. The number of OA patients has been steadily increasing in the current aging society, but no adequate diagnostic or therapeutic method therefor has yet been established. The initial pathologic changes in OA are thought to be the degeneration and wear of the joint cartilage caused by mechanical stress due to aging. These changes advance at an extremely slow rate and lead to the gradual progression of pain.

The current drug therapy of OA uses, in systemic therapy, 1) an antipyretic analgesic (acetaminophen) or 2) nonsteroidal anti-inflammatory drugs (hereinafter also referred to as NSAIDs), or, in topical therapy (intra-articular injection), 3) hyaluronic acid (hereinafter also referred to as HA) preparations, and 4) steroid preparations. When systemic drug therapy including NSAIDs does not alleviate the pain or swelling of a local part of a joint, the intra-articular injection of steroid preparations, which have the most excellent anti-inflammatory activity, has been heretofore carried out. However, steroid preparations have problems in terms of safety e.g. because they may cause intra-articular injection syndrome (steroid arthropathy) and may have systemic side effects. Thus, HA preparations are becoming more useful as a safer intra-articular injection alternative to steroid preparations.

HA is an endogenous polysaccharide composed of repeating units of N-acetylglucosamine and glucuronic acid. HA serves to hold the viscoelasticity and load-absorbing and lubricating effects of synovial fluid as a main component constituting the synovial fluid, and, in the cartilage matrix, plays a central role in maintaining the water-holding capacity and viscoelasticity thereof by binding to cartilage proteoglycan to form a polymer called aggrecan.

Since the injection of HA with a molecular weight of about 600,000 daltons or a crosslinked product thereof into a knee joint eliminates pain derived from OA, HA preparations are widely used as one of OA therapies. Further, a high molecular weight type HA preparation having a molecular weight close to that of HA present in normal synovial fluid (product name: Suvenyl™, manufacture and distribution: Chugai Pharmaceutical Co., Ltd.) is approved in Japan with regard to an indication for the elimination of knee pain associated with rheumatoid arthritis (hereinafter also referred to as RA). In this regard, it is said that the molecular weight of HA correlates with the potency thereof and the effect of a high molecular weight type HA is longer-lasting and more potent than that of a low molecular weight type HA.

It is generally thought that HA preparations reverse the impaired viscosity and elasticity of synovial fluid resulting from the pathologic condition of OA (or RA), to eliminate pain. However, an effect of an externally added HA preparation lasts over a long period of time whereas the HA disappears from synovial fluid within several days. Thus, there is also suggested a possibility that an externally added HA preparation could act in eliminating pain by a mechanism different from that for the above-described improvement in the viscoelasticity of synovial fluid. Examples of the mechanism include an inhibitory effect against OA synovitis which is to be described hereinafter.

The pathogenic mechanism for pain and inflammation in OA still has many unclear points, but attention has been recently given to a possible link of the mechanism with synovitis which is secondarily triggered by cartilage degeneration. OA synovitis is thought to be the major exacerbation factor promoting the pathologic condition of OA because it not only becomes the main cause of symptoms of pain and inflammation such as hydrarthrosis or heat, but also accelerates joint destruction through the production of proteases, cytokines, and radicals. In addition, OA synovitis does not exhibit such a significant proliferative change as seen in RA, but has many aspects common to RA synovitis, such as synovial cell proliferation, angiogenesis, hyperemia, and subsynovial edema and fibrosis. Thus, the control of OA synovitis is important from the standpoint of efficiently eliminating pain and inflammation in OA to prevent the progression of the pathologic condition thereof.

The effect of HA on the synovial membrane has not been fully elucidated yet, but it is known from an experiment using an isotope that HA accumulates and is present over a longer period of time in the synovial membrane than in the articular cavity. It has been also reported that receptors recognizing HA (CD44 and RHAMM (receptor for HA-mediated motility)) are present on the surface layer of synovial cells constructing synovial tissue and that synovial cells are provided with a mechanism for incorporating HA even with a molecular weight of 2,000,000 or more into the cell through CD44 on the surface layer thereof. It is suggested from these findings that at least part of the pain-eliminating effect of HA is exerted through its effect on the synovial membrane; however, HA preparations do not have enough effect to inhibit inflammatory symptoms per se induced in OA synovitis, and therefore, their effect against OA and RA, which exhibit strong inflammatory symptoms, are far from adequate.

As drugs controlling synovitis have been well known a class of drugs called disease modifying anti-rheumatic drugs (hereinafter also referred to as DMARD) used in treating RA. Among others, methotrexate (hereinafter also referred to as MTX) is a drug having advantages, for example, of having excellent potency and of having relatively short time before the exertion of its effect. However, MTX is known to cause, in regions other than joint which is to be treated, serious side effects (hepatopathy, hematopoietic disorder, lung disorder, gastrointestinal tract disturbance, etc.) ascribed to the mechanism of the action of MTX, because the use of MTX has been approved only for systemic administration (only capsules of MTX have been currently approved as a pharmaceutical for treating RA in Japan; tablets and injections thereof have been approved abroad). As a result, it is essential in the use of MTX that side effects are sufficiently monitored and a measure for the incidence of side effects be taken. Because of the great fears of such side effects, synovitis-suppressing drugs including MTX have no approved indication for other joint diseases such as OA, whose symptoms are milder than those of RA. Thus, if a means for lessening the systemic side effects of MTX or a means for enabling MTX to exert its action only in the region where the development of the beneficial effect of MTX is required is found out, it will become possible not only to provide a safer RA therapy, but also to use MTX in a wide range of joint diseases.

Several methods for localizing the effect of MTX only to the inside of a joint and the synovial membrane have been attempted as means for lessening the side effects of MTX and extracting only the desired effect thereof. For example, a method for topically (intra-articularly) administering MTX alone has been reported; however, it does not enable the sufficient beneficial effect thereof to be exerted, because MTX rapidly disappears from the joint cavity. A method for using MTX formed into a liposome to improve the intra-articular retention thereof utilizing the phagocytic capacity of macrophage has been also reported; however, its clinical usefulness has not yet been confirmed. Thus, technical improvement is still necessary in order to lessen the side effects of MTX as a therapeutic drug for joint diseases and extract only the expected effect.

As described above, the synovial membrane is a tissue in which HA is apt to accumulate. In addition, the synovial cell is provided with a mechanism for incorporating HA into the cell through an HA receptor such as CD44. Thus, HA seems to have a possibility of providing a carrier for accumulating a drug in the synovial membrane. Several techniques using HA as an internal carrier for drugs have been previously reported. However, there are few known examples of applying HA to a technique with regard to the creation of a drug delivery system (hereinafter also referred to as DDS) which is for therapeutic drugs suitable for joint diseases, particularly drugs suitable for controlling synovitis, represented by MTX.

Previously known examples of reports include a polysaccharide-drug conjugate, in which a drug is conjugated with a polysaccharide including HA through a peptide chain (Patent Document 1: Japanese Patent Laid-Open No. 05-39306, Patent Document 2: International Publication WO94/19376, and so on). Each of the documents relates to a DDS technique for anticancer drugs, and states that the DDS technique improves the transfer of the drug into a cancer tissue.

In Japanese Patent Laid-Open No. 05-39306, MTX is used, intended as an anticancer drug. However, since the technique is characterized by the improved transfer of MTX into a cancer tissue and the absence of long-term persistence thereof in the body, the binding rate of MTX is made high (6.4 to 19% in a working example of the patent document) and the molecular weight of HA is made low (100,000 daltons in a working example in the patent document), in order to enhance the anticancer effect. In addition, binding of a peptide chain with the hydroxy group of HA through isourea bonding makes the conjugate less stable in an aqueous solution.

There are also examples of reports, in each of which a conjugate in which HA is conjugated with a drug has been used as a therapeutic drug for joint diseases. For example, International Publication WO99/59603 (Patent Document 3) discloses a conjugate in which HA is conjugated with a drug through a spacer such as a butyleneamine group ($-C_4H_8NH-$) or an octyleneamine group ($-C_8H_{16}NH-$). This patent document describes the conjugate as that can exert a beneficial effect in the state where the drug is kept conjugated, assuming the beneficial effect outside cells. In this conjugate, in fact, the conjugation between a drug and HA through the spacer is relatively strong, and therefore this technique is difficult to apply to a drug which, like MTX, can not exert a beneficial effect unless it is released from the conjugate.

In addition, this patent document is directed to a conjugate using a matrix metalloproteinase inhibitor (hereinafter also referred to as MMPI) as a drug, and the disclosed working examples also relate only to a MMPI conjugate. No conjugate using MTX as a drug is specifically disclosed, and no description of the usefulness of the conjugate as a pharmaceutical is also contained.

International Publication WO02/44218 (Patent Document 4) discloses an HA-drug conjugate produced by using a spacer in which a particular group (norbornene) is further bound to a 13-amino-4,7,10-trioxatridecanyl group and forming carbamate bonding between the norbornene and the hydroxy group of HA. However, this conjugate also seems to be intended to show a beneficial effect outside cells as in Patent Document 2; the effect is exerted in the state where the drug is kept conjugated. Thus, this technique is difficult to apply to a drug such as MTX which can not exert a beneficial effect unless it is released from the conjugate. In addition, Patent Document 3 is directed to a conjugate using MMPI as a drug, and no indication of a conjugate using MTX as a drug is given.

As discussed previously, none of the above-mentioned documents describes an HA-MTX conjugate using MTX, and neither description nor indication of the use of an HA-MTX conjugate as a therapeutic drug for joint diseases is given.

In addition, the present inventors have demonstrated that, in a method for synthesizing an HA-drug conjugate known as a prior art, the molecular weight of HA greatly decreases during synthesis process, leading to the loss of the beneficial effect of HA. A conventional method for synthesizing an HA-drug conjugate uses general conditions of organic synthetic reaction and after-treatment, but the method is necessary to be further improved in order to prepare a conjugate of high molecular weight HA and a drug.

As described above, an HA-drug conjugate used as a pharmaceutical, particularly a high molecular weight HA-drug conjugate suitable for treating joint diseases, a preparation using the same, and a method for synthesizing the conjugate have not been previously known.

Patent Document 1: Japanese Patent Laid-Open No. 5-39306
Patent Document 2: International Publication WO94/19376 pamphlet
Patent Document 3: International Publication WO99/59603 pamphlet
Patent Document 4: International Publication WO02/44218 pamphlet

DISCLOSURE OF THE INVENTION

Problems to be Solved by the Invention

An object of the present invention is to provide a hyaluronic acid-methotrexate conjugate useful as a therapeutic drug for joint diseases.

Means For Solving the Problems

The present inventors have found that a hyaluronic acid-methotrexate conjugate, in which methotrexate is conjugated with a carboxyl group of hyaluronic acid through a linker containing a peptide chain, has a prominent effect as a therapeutic drug for joint diseases, thereby accomplishing the invention.

Thus, one aspect of the invention provides a hyaluronic acid-methotrexate conjugate in which methotrexate is conjugated with a carboxyl group of hyaluronic acid through a linker containing a peptide chain consisting of 1 to 8 amino acids. In one embodiment of the invention, the linker contains a peptide chain consisting of 1 to 8 amino acids and a $C_{2-20}$ alkylenediamine chain into which 1 to 5 oxygen atoms are optionally inserted and/or which is optionally substituted by a carboxyl group or a $C_{1-6}$ alkoxycarbonyl group.

Another aspect of the invention also provides the above-described hyaluronic acid-methotrexate conjugate, wherein methotrexate conjugated with the linker is represented by formula (I), (II), (III), or (IV):

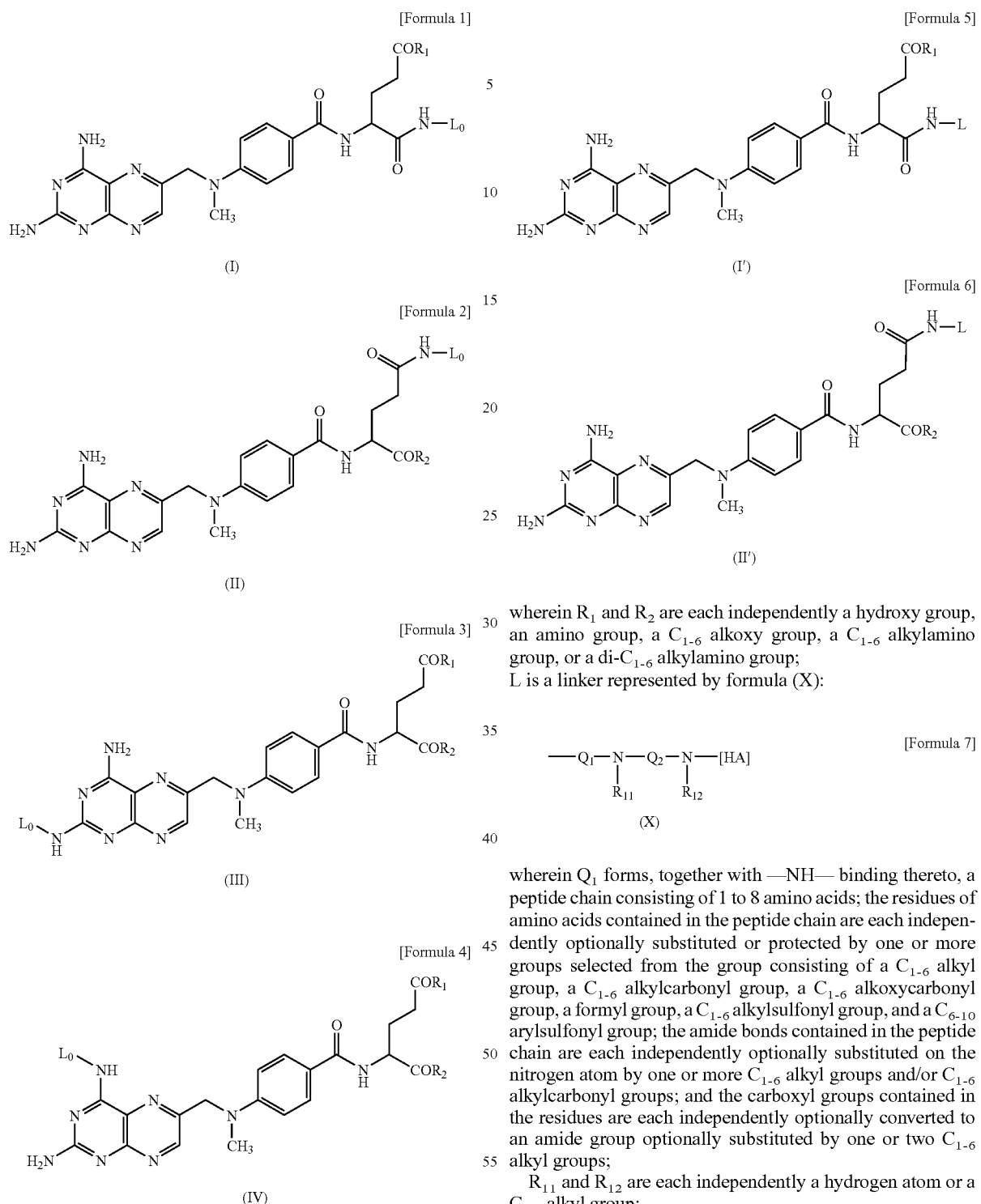

(I)

(II)

(III)

(IV)

wherein $R_1$ and $R_2$ are each independently a hydroxy group, an amino group, a $C_{1-6}$ alkoxy group, a $C_{1-6}$ alkylamino group, or a di-$C_{1-6}$ alkylamino group;

$L_0$ is the conjugating position of the linker.

A further aspect of the invention provides the above-described hyaluronic acid-methotrexate conjugate, wherein the linker containing a peptide chain and methotrexate conjugated with the linker is represented by formula (I') or (II'):

(I')

(II')

wherein $R_1$ and $R_2$ are each independently a hydroxy group, an amino group, a $C_{1-6}$ alkoxy group, a $C_{1-6}$ alkylamino group, or a di-$C_{1-6}$ alkylamino group;

L is a linker represented by formula (X):

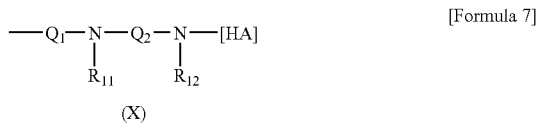

(X)

wherein $Q_1$ forms, together with —NH— binding thereto, a peptide chain consisting of 1 to 8 amino acids; the residues of amino acids contained in the peptide chain are each independently optionally substituted or protected by one or more groups selected from the group consisting of a $C_{1-6}$ alkyl group, a $C_{1-6}$ alkylcarbonyl group, a $C_{1-6}$ alkoxycarbonyl group, a formyl group, a $C_{1-6}$ alkylsulfonyl group, and a $C_{6-10}$ arylsulfonyl group; the amide bonds contained in the peptide chain are each independently optionally substituted on the nitrogen atom by one or more $C_{1-6}$ alkyl groups and/or $C_{1-6}$ alkylcarbonyl groups; and the carboxyl groups contained in the residues are each independently optionally converted to an amide group optionally substituted by one or two $C_{1-6}$ alkyl groups;

$R_{11}$ and $R_{12}$ are each independently a hydrogen atom or a $C_{1-6}$ alkyl group;

$Q_2$ is $C_{2-20}$ alkylene, wherein the alkylene optionally has 1 to 5 oxygen atoms inserted and/or is optionally substituted by a carboxyl group or a $C_{1-6}$ alkoxycarbonyl group; and

[HA] represents the position of conjugation with hyaluronic acid, and the linker forms an amide bond with a carboxyl group contained in the hyaluronic acid.

Other aspects of the invention also provide a pharmaceutical composition and a therapeutic drug for joint diseases, each of which contains the above-described hyaluronic acid-methotrexate conjugate as an active ingredient.

A further aspect of the invention provides a compound of the following formula (Va) or (Vb), which can be used in producing the above-described hyaluronic acid-methotrexate conjugate:

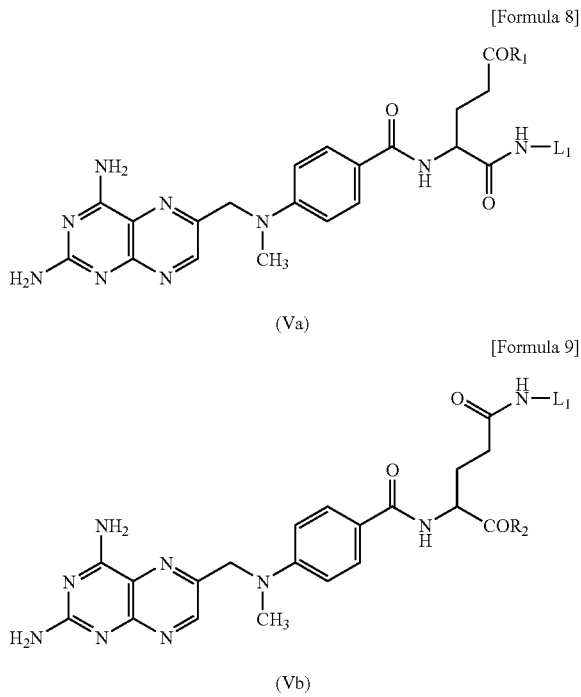

[Formula 8]

(Va)

[Formula 9]

(Vb)

wherein $R_1$ and $R_2$ are each independently a hydroxy group, an amino group, a $C_{1-6}$ alkoxy group, a $C_{1-6}$ alkylamino group, or a di-$C_{1-6}$ alkylamino group;
$L_1$ is a linker represented by formula (X'):

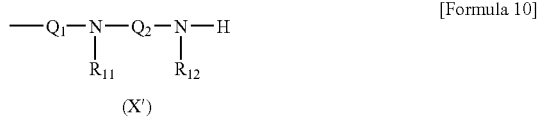

[Formula 10]

(X')

wherein $Q_1$ forms, together with —NH— binding thereto, a peptide chain consisting of 1 to 8 amino acids; the residues of amino acids contained in the peptide chain are each independently optionally substituted or protected by one or more groups selected from the group consisting of a $C_{1-6}$ alkyl group, a $C_{1-6}$ alkylcarbonyl group, a $C_{1-6}$ alkoxycarbonyl group, a formyl group, a $C_{1-6}$ alkylsulfonyl group, and a $C_{6-10}$ arylsulfonyl group; the amide bonds contained in the peptide chain are each independently optionally substituted on the nitrogen atom by one or more $C_{1-6}$ alkyl groups and/or $C_{1-6}$ alkylcarbonyl groups; and the carboxyl groups contained in the residues are each independently optionally converted to an amide group optionally substituted by one or two $C_{1-6}$ alkyl groups;
$R_{11}$ and $R_{12}$ are each independently a hydrogen atom or a $C_{1-6}$ alkyl group; and
$Q^2$ is $C_{2-20}$ alkylene into which 1 to 5 oxygen atoms are optionally inserted and/or which is optionally substituted by a carboxyl group or a $C_{1-6}$ alkoxycarbonyl group.

A further aspect of the invention also provides a process for producing the above-described hyaluronic acid-methotrexate conjugate, which comprises the steps of reacting the above-described compound of formula (Va) or (Vb) with hyaluronic acid and converting a carboxyl group of the hyaluronic acid to an N-substituted amide group.

The present invention is described below in detail.

The hyaluronic acid-methotrexate conjugate (HA-MTX conjugate) of the invention is a novel compound. According to the invention, a structure in which methotrexate (MTX) is conjugated with a carboxyl group of hyaluronic acid (HA) through a linker containing a peptide chain is used as a means for conjugating hyaluronic acid HA with MTX to allow the conjugate to maintain the pain-eliminating effect of HA and also to have a synovitis-alleviating effect of MTX. Thus, the HA-MTX conjugate of the invention will be accumulated on the synovial membrane and then incorporated into synovial cells to exert the beneficial effect of MTX in the cells.

Hence, when administered into the knee joint of OA or RA patients, the HA-MTX conjugate of the invention exerts a pain-eliminating effect based on the property of HA as in a conventional HA preparation while it accumulates in synovial tissue and simultaneously is gradually incorporated into synovial cells and releases MTX to persistently exert a synovitis-suppressing effect. This enables the dose of MTX to be greatly reduced compared to that for the oral administration thereof and thereby can eliminate fears of systemic side effects, which would be problematical for the oral administration. At the site of administration, further, an HA preparation and MTX can exert pharmacological effects different in the action mechanism from those of each other, and a synergistic beneficial effect therebetween can be therefore expected.

Thus, according to the HA-MTX conjugate of the invention, there is provided a non-conventional excellent therapeutic drug for joint diseases, which has the aspect of HA as an intra-articular therapy and by which the synovitis-suppressing effect of MTX can be safely exerted only in the treated joint.

The hyaluronic acid-methotrexate conjugate (HA-MTX conjugate) of the invention is methotrexate conjugated with a carboxyl group of hyaluronic acid through a linker containing a peptide chain.

For the purpose of the invention, "hyaluronic acid (HA)" is not particularly restricted, but, for example, is a polymer of disaccharide consisting of glucuronic acid and N-acetylglucosamine, which polymer has an average molecular weight of 50,000 to 10,000,000 daltons. Salts of hyaluronic acid are not particularly restricted, but include, for example, the salts of sodium, potassium, calcium, aluminium, zinc, iron, ammonium, and tetrabutylammonium. Specific examples of hyaluronic acid or its salt and a mixture thereof include Suvenyl™ (manufacture and distribution: Chugai Pharmaceutical Co., Ltd.); Artz™ (manufacture: Seikagaku Corporation, distribution: Kaken Pharmaceutical Co., Ltd.); and Opegan™ (manufacture: Seikagaku Corporation, distribution: Santen Pharmaceutical Co., Ltd.). For the purpose of the invention, "hyaluronic acid derivative" refers to a substance having a HA skeleton, which is derived from HA. Hyaluronic acid derivatives are not particularly restricted, but include, for example, HA wherein one or more carboxyl groups are esterified (e.g., benzyl esterified HA (trade name: Hyaff™, from Fidia Advanced Biopolymers), HA further polymerized by crosslinking using formaldehyde (e.g., trade name: Synvisc™ from Biomatrix), and acetylated HA obtained by acetylating one or more hydroxy groups in HA.

The HA-MTX conjugate of the invention preferably holds the size of molecular weight and viscoelasticity comparable to those of HA whose pain-eliminating effect is clinically confirmed, in order not to diminish the pain-eliminating effect of HA therein. Specifically, the HA-MTX conjugate preferably has a molecular weight of 600,000 to 6,000,000 daltons, more preferably 800,000 to 6,000,000 daltons, particularly preferably 1,000,000 to 5,000,000 daltons, considering the factor that increased molecular weight leads to an increase in viscoelasticity which renders it difficult to handle, and the effect of HA as an internal carrier.

Here, the molecular weights of the raw material HA and the HA-MTX conjugate are determined by a method for calculating viscosity-average molecular weight from limiting viscosity. Conversion from limiting viscosity ([η]) to viscosity-average molecular weight (Mw) can be calculated using the following equation.

$$Mw=([\eta]/0.00036)^{1.282}$$

In the linker containing a peptide chain of the invention, the peptide chain is composed of amino acids. Examples of the amino acids include natural α-amino acids such as glycine, alanine, serine, proline, valine, threonine, cysteine, leucine, isoleucine, asparagine, aspartic acid, lysine, glutamine, glutamic acid, methionine, histidine, phenylalanine, arginine, tyrosine, and tryptophan; and non-natural α-amino acids such as an α-amino acid having an alkyl side chain (e.g., norvaline, norleucine, or t-leucine), alanine or glycine substituted by a cycloalkyl group (e.g., cyclopentylalanine, cyclohexylalanine, or cyclohexylglycine), and alanine or glycine substituted by an aryl group (e.g., pyridylalanine, thienylalanine, naphthylalanine, substituted phenylalanine, or phenylglycine), β-amino acids such as β-alanine, γ-amino acids such as γ-aminobutyric acid, and aminosulfonic acids such as taurine. Amino acids in the linker peptide of the invention also include those whose residues are properly substituted or protected. For example, the functional group of the residue can be protected using a protective group. Protective groups used for this purpose are well known in the art, and some examples thereof are described in other paragraphs of the present specification. A method for introducing each of the substituents and protective groups, particularly the protective groups, may be that well-known in the art.

The linker may be composed of only amino acids, or may contain, inside or in the end of a peptide chain, a part derived from a compound other than amino acid. For example, the linkers include a linker which has a peptide chain wherein a diamino compound such as alkylenediamine or oxaalkylenediamine or a dicarboxylic acid compound such as succinic acid is linked inside or in the end of the peptide chain. When the linker contains a compound other than amino acid inside or in the end of the peptide chain and is linked to carboxyl groups of MTX and hyaluronic acid, a diamino compound such as alkylenediamine or oxaalkylenediamine is preferably present at the end of the peptide chain; particularly preferably, ethylenediamine or 4,7,10-trioxa-1,13-tridecanediamine is present at the end of the peptide chain. The amino acids constituting the peptide chain are not particularly restricted, but are preferably α-amino acids in view of affinity to protease; the end of the linker containing a peptide chain, which conjugates to MTX, is preferably an α-amino acid.

The number of amino acids constituting the peptide chain is not particularly restricted, but typically 1 to 8, preferably 1 to 6, particularly preferably 1 to 4. The residues of amino acids constituting the peptide chain can each independently be properly substituted or protected by one or more groups. Non-limiting examples of such groups include $C_{1-6}$ alkyl groups, $C_{1-6}$ alkylcarbonyl groups, $C_{1-6}$ alkoxycarbonyl groups (e.g., a methoxycarbonyl group, an ethoxycarbonyl group, an (n- or i-)propyloxycarbonyl group, and an (n-, s-, or t-)butoxycarbonyl group), a formyl group, $C_{1-6}$ alkylsulfonyl groups (e.g., a methanesulfonyl group, an ethanesulfonyl group, and an (n- or i-)propanesulfonyl group), and $C_{6-10}$ arylsulfonyl groups (e.g., a benzenesulfonyl group, a (o-, m-, or p-)toluenesulfonyl group, and a (1- or 2-)naphthalenesulfonyl group). As a result of substitution or protection, for example, the carboxyl groups contained in the residues may be converted to $C_{1-6}$ alkoxycarbonyl groups; the hydroxy groups therein to $C_{1-6}$ alkoxy groups or $C_{1-6}$ alkylcarbonyloxy groups; and the amino groups therein to $C_{1-6}$ alkylamino groups, di-$C_{1-6}$ alkylamino groups, $C_{1-6}$ alkylcarbonylamino groups, or N—$C_{1-6}$ alkyl-$C_{1-6}$ alkylcarbonylamino groups. In addition, the carboxyl group contained in the residue is optionally converted to an amide group optionally substituted by one or two $C_{1-6}$ alkyl groups. When nitrogen-containing heterocycles such as an indole ring and an imidzole ring are contained in the residues, the nitrogen atoms on the rings may be each independently protected by a $C_{1-6}$ alkyl group or a $C_{1-6}$ alkylcarbonyl group. When a guanidine group is contained in the residue, the nitrogen atom contained therein may be also protected by a $C_{1-6}$ alkyl group or a $C_{1-6}$ alkylcarbonyl group. Other protective groups for the nitrogen atom are not particularly restricted, but may be also selected from commonly used groups such as the above-described alkoxycarbonyl, formyl, $C_{1-6}$ alkylsulfonyl, and $C_{1-6}$ arylsulfonyl groups. When a thiol group is contained in the residue, it may be protected by a $C_{1-6}$ alkyl group or a $C_{1-6}$ alkylcarbonyl group. In addition, the amide bond contained in the peptide may be also substituted by a $C_{1-6}$ alkyl group and/or a $C_{1-6}$ alkylcarbonyl group, and may be, for example, converted to —CON($C_{1-6}$ alkyl)-.

The amino acid sequence composing the peptide chain is not particularly restricted, but examples thereof include the following. In this regard, when a target protease is present in the living body and the substrate recognition amino acid sequence therefor is known, an amino acid sequence containing the recognition site and/or cleavage site may be also used.

Peptide chains consisting of one amino acid: Ala, Arg, Asn, Asp, Cys, Gln, Glu, Gly, His, Ile, Leu, Lys, Met, Phe, Pro, Ser, Thr, Trp, Tyr, Val, and the like. Preferred are Phe, Tyr, Ile, and Glu.

Peptide chains consisting of two amino acids: PhePhe, PheGly, PheLeu, TyrPhe, TrpPhe, PheTrp, PheTyr, GlyPhe, GlyGly, and the like. Preferred are PhePhe and PheGly.

Peptide chains consisting of three amino acids: PheGlyGly, PheLeuGly, PhePheGly, AsnPhePhe, GlyPhePhe, LeuPhePhe, LeuAlaLeu, AlaValAla, GlyAlaPhe, GlyPheAla, GlyIleAla, GlyIlePhe, GlyLeuAla, GlyValAla, GlyValPhe, GlyGlyGly, and the like. Preferred is AsnPhePhe.

Peptide chains consisting of four amino acids: GlyPheLeuGly, GlyPhePheLeu, GlyPhePheAla, GlyPheTyrAla, GlyPheGlyPhe, GlyPheGlyGly, GlyGlyPheGly, GlyGlyPheTyr, GlyGlyGlyGly, LeuAlaLeuAla, AlaLeuAlaLeu, AlaGlyValPhe, GluAsnPhePhe, and the like. Preferred is GlyPheLeuGly.

The linker according to the invention may have a structure represented, for example, by formula (X) above, where $Q_1$ forms, together with —NH— binding thereto, a peptide chain consisting of 1 to 8 of the amino acids as described above. In addition, $Q_2$ is $C_{2-20}$ alkylene into which 1 to 5 oxygen atoms are optionally inserted or which is optionally substituted by a carboxyl group or a $C_{1-6}$ alkoxycarbonyl group. Specific examples of $Q_2$ include an ethane-1,2-diyl group, propane-1,3-diyl group, butane-1,4-diyl group, pentane-1,5-diyl group, hexane-1,6-diyl group, heptane-1,7-diyl group, octane-1,8-diyl group, nonane-1,9-diyl group, decane-1,10-diyl group, 2-methylpropane-1,3-diyl group, 2-methylbutane-1,4-diyl group, 3-methylbutane-1,4-diyl group, 3-methylpentane-1,5-diyl group, 3-ethylpentane-1,5-diyl group, 2-methylhexane-1,6-diyl group, 3-methylhexane-1,6-diyl group, 4-methylheptane-1,7-diyl group, 3-oxapentane-1,5-diyl group, 3-oxahexane-1,6-diyl group, 4-oxahexane-1,6-diyl group, 3-oxaheptane-1,7-diyl group, 4-oxaheptane-1,7-diyl group, 4-oxaoctane-1,8-diyl group, 3,6-dioxaoctane-1,8-diyl group, 3,6-dioxanonane-1,9-diyl group, 3,6-dioxa-4-methyl-nonane-1,9-diyl group, 4,7-dioxadecane-1,10-diyl group, 4,9-dioxadodecane-1,12-diyl group, and 4,7,10-trioxatridecane-1,13-diyl group. Preferred examples include an ethane-1,2-diyl group, pentane-1,5-diyl group, 3-oxapentane-1,5-diyl group, 3,6-dioxaoctane-1,8-diyl group, 4,7-dioxadecane-1,10-diyl group, 4,9-dioxadodecane-1,12-diyl group, and 4,7,10-trioxatridecane-1,13-diyl group.

The HA-MTX conjugate of the invention may take any conjugating mode provided that MTX is conjugated to a carboxyl group of HA through a linker containing a peptide chain. Thus, the linker containing a peptide chain can be conjugated with:
1) the carboxyl group at the α-position of MTX;
2) the carboxyl group at the γ-position of MTX; or
3) the amino group of MTX,
and plural such conjugating modes may coexist (for example, conjugates conjugated with the carboxyl group at the α-position of MTX and conjugates conjugated with the carboxyl group at the γ-position of MTX may coexist). However, the linker containing a peptide chain is preferably conjugated with the carboxyl group at the α-position of MTX and/or the carboxyl group at the γ-position thereof, more preferably the carboxyl group at the α-position of MTX, in view of affinity to protease and synthesis.

According to the HA-MTX conjugate of the invention, the linker containing a peptide chain is particularly preferably a linker containing a peptide chain which consists of α-amino acids and has a diamino compound at the end of the peptide chain; and the conjugating mode of the linker is particularly preferably a conjugating mode consisting of the conjugating of the N-terminal of the peptide chain with the carboxyl group at the α-position of MTX through acid amide bonding and the conjugating of the C-terminal of the peptide chain with a carboxyl group of HA through acid amide bonding via the diamino compound.

In the hyaluronic acid-methotrexate conjugate of the invention, the part of methotrexate (MTX) may be made in the form of a prodrug by a known method, in addition to modification by the linker.

As used herein, "$C_{1-6}$ alkyl group" refers to a straight-chain or branched alkyl group of 1-6 carbon atoms, and examples of the group include a methyl group, an ethyl group, a n-propyl group, an i-propyl group, a n-butyl group, a s-butyl group, an i-butyl group, a t-butyl group, a n-pentyl group, a 3-methylbutyl group, a 2-methylbutyl group, a 1-methylbutyl group, a 1-ethylpropyl group, and a n-hexyl group.

As used herein, "$C_{1-6}$ alkylcarbonyl" refers to a straight-chain or branched alkylcarbonyl group of 1-6 carbon atoms, and examples of the group include those having the previously defined alkyl group as an alkyl part, such as an acetyl group, a propionyl group, a 2-methylpropionyl group, or a 2,2-dimethylpropionyl group.

As used herein, "$C_{1-6}$ alkoxy" refers to a straight-chain or branched alkoxy group of 1-6 carbon atoms, and examples of the group include those having the previously defined alkyl group as an alkyl part, such as a methoxy group, an ethoxy group, or a n-propoxy group.

As used herein, "$C_{1-6}$ alkylamino" refers to a straight-chain or branched alkylamino group of 1-6 carbon atoms, and examples of the group include those having the previously defined alkyl group as an alkyl part, such as a methylamino group, an ethylamino group, or an n-propylamino group.

As used herein, "di-$C_{1-6}$ alkylamino" refers to a straight-chain or branched dialkylamino group of 1-6 carbon atoms, and examples of the group include those having as alkyl parts the previously defined alkyl groups, which may be identical or different, such as a dimethylamino group, an ethylmethylamino group, a diethylamino group, or an ethyl-n-propylamino group.

As used herein, "di-$C_{2-20}$ alkylene" refers to a straight-chain or branched alkylene group of 2-20 carbon atoms, and examples of the group include an ethylene group, a propylene group, a butylene group, an octylene group, and a decalene group.

As used herein, "$C_{1-6}$ alkoxycarbonyl group" refers to a straight-chain or branched alkoxycarbonyl group of 1-6 carbon atoms, and examples of the group include those having the previously defined alkyl group as an alkyl part, such as a methoxycarbonyl group, an ethoxycarbonyl group, or an n-propoxycarbonyl group.

As used herein, "$C_{1-6}$ alkylsulfonyl group" refers to a straight-chain or branched alkylsulfonyl group of 1-6 carbon atoms, and examples of the group include those having the previously defined alkyl group as an alkyl part, such as a methanesulfonyl group, an ethanesulfonyl group, or a n-propanesulfonyl group.

As used herein, "acylation" includes $C_{1-6}$ alkylcarbonylation and benzoylation; the benzoyl group is optionally substituted by a $C_{1-6}$ alkyl, a halogen atom, a $C_{1-6}$ alkoxy, and so on.

The conjugation rate of MTX in the HA-MTX conjugate of the invention is preferably in such a range that the beneficial effect is exerted and there is no fear of side effects. As used herein, "conjugation rate of MTX" is calculated from the following equation:

$$\begin{pmatrix} \text{Conjugation rate} \\ \text{of } MTX\ (\%) \end{pmatrix} = \frac{\begin{pmatrix} \text{Number of } MTX \text{ moieties} \\ \text{conjugated in a molecule} \end{pmatrix}}{\begin{pmatrix} \text{Number of glucoronic} \\ \text{acid moieties in a molecule} \end{pmatrix}} \times 100 \quad \text{[Formula 11]}$$

The conjugation rate of MTX is not particularly restricted, but is preferably 0.5% or more, more preferably 1.0% or more in view of the exertion of the beneficial effect. On the other hand, the conjugation rate is preferably less than 10% in order to localize the effect of MTX to the administration region and reduce the systemic side effects of MTX. In addition, considering that the HA-MTX conjugate of the invention causes insolubilization thereof and thereby produces troubles on synthesis when the conjugate has a high molecular weight and a high conjugation rate of MTX, the conjugation rate of MTX is preferably 0.5% or more and less than 4.5%, particularly preferably 1.0% or more and less than 4.5%.

The HA-MTX conjugate of the invention may be also present in the form of a salt, but the salt is preferably a pharmaceutically acceptable salt in view of the application thereof. Examples of the salt include salts of sodium, potassium, calcium, aluminium, zinc, iron, ammonium, and tetrabutylammonium.

In synthesizing the HA-MTX conjugate of the invention, HA, a linker containing a peptide chain, and MTX may be conjugated in proper order. For example, there are exemplified a route in which a linker containing HA-peptide chain is constructed before introducing MTX, and a route in which a linker containing MTX-peptide chain is constructed before introducing HA. Each of the conjugating reactions may be accomplished by reaction at a temperature of −20° C. to 40° C. for several minutes to several days using a solvent and condensation agent which are employed for conventional acid amide conjugating reaction and, if necessary, a reaction-promoting additive. An example of the solvent includes water, N,N-dimethylformamide, N,N-dimethylacetamide, dimethylsulfoxide, tetrahydrofuran, dioxane, methanol, ethanol, dichloromethane, chloroform, and so on, or a mixture thereof. An example of the condensation agent includes a carbodiimide compound such as 1-ethyl-3-(3-dimethylaminopropyl)carbodiimide; dicyclohexylcarbodiimide, or diisopropylcarbodiimide, benzotriazol-1-yl-oxy-tris(dimethylamino)phosphonium hexafluorophosphate, O-(7-azabenzotriazol-1-yl-)-1,1,3,3-tetramethyluronium hexafluorophosphate, and 1-ethoxycarbonyl-2-ethoxy-1,2-dihydroquinoline. An example of the reaction-promoting additive includes an active ester agent such as N-hydroxysuccinimide, N-hydroxy-5-norbornene-2,3-carboximide, 1-hydroxybenzotriazole, 1-hydroxy-7-azabenzotriazole, or 3,4-dihydro-3-hydroxy-4-oxo-1,2,3-benzotriazole; and a pH adjustor such as triethylamine, N-methylmorpholine, N,N-diisopropylethylamine, or tris[2-(2-methoxyethoxy)ethyl]amine. In the reaction, to a functional group such as an amino acid side chain (e.g., a hydroxy group, a carboxyl group, or an amino group), it is possible to use a protective group widely employed in conventional organic synthesis.

Here, to prevent a reduction in the molecular weight of HA, it is preferable to use the route in which a linker containing MTX-peptide chain is constructed before introducing HA, in view of the ease of controlling the conjugatation reaction. The solvent is preferably water, N,N-dimethylformamide, tetrahydrofuran, ethanol, or a mixture thereof, and most preferably a mixture of water and tetrahydrofuran in which the mixing ratio thereof is most preferably 1:1. The condensation agent is preferably a water-soluble one, and most preferably 1-ethyl-3-(3-dimethylaminopropyl)carbodiimide, which is most preferably added at an amount of 0.1 equivalent based on the carboxyl group in HA. The reaction-promoting additive is most preferably 3,4-dihydro-3-hydroxy-4-oxo-1,2,3-benzotriazole for the active ester agent, which is most preferably added at an amount of 0.1 equivalent based on the carboxyl group in HA. The pH adjustor is most preferably tris[2-(2-methoxyethoxy)ethyl]amine; the pH during reaction is most preferably 6 to 7. The reaction temperature is preferably −10° C. to 30° C. and most preferably 0° C. to 15° C. The reaction time is preferably 1 hour to 48 hours and most preferably 12 hours to 24 hours.

As used herein, "joint disease" refers specifically to a disease such as articular cartilage defect, osteoarthritis (including a primary disease, which has no evident cause, and a secondary disease, in which causative disease is present), shoulder periarthritis, rheumatoid arthritis, reactive arthritis, viral arthritis, suppurative arthritis, tuberculous arthritis, or neuroarthropathy, and further includes joint pains in these diseases (for example, knee joint pain in rheumatoid arthritis). As used herein, "therapeutic drug for joint diseases" includes not only a drug used for treating the above-described joint diseases but also a drug used for the prevention thereof, the suppression of the progression of the pathologic condition (the prevention of deterioration or the maintenance of the existing condition), or the like.

The HA-MTX conjugate of the invention may be used in the form of a pharmaceutical composition by properly adding, to an effective amount thereof, a pharmaceutically acceptable carrier, excipient, disintegrator, lubricant, binder, perfume or colorant, or the like. The pharmaceutical composition containing the HA-MTX conjugate of the invention as active ingredient is preferably used as a therapeutic drug for joint diseases, and particularly preferably employed in the form of a topical preparation for administration into the joint.

By way of non-limiting example, when the HA-MTX conjugate of the invention is formulated as a therapeutic drug for joint diseases, it may be dissolved at a desired concentration e.g., in physiological saline or phosphate physiological saline for formulation in the form of an injection preparation. In this case, the solution may be optionally adjusted to a desired pH by adding an acid or base. The solution may be also adjusted to a desired salt concentration by adding an inorganic salt including a monovalent metal salt such as sodium or potassium or a divalent metal salt such as magnesium, calcium, or manganese. In addition, a stabilizer and the like may be optionally added. The solution of the HA-MTX conjugate of the invention thus prepared may be distributed, preliminarily charged in a disposal injection syringe or the like. When a therapeutic drug for joint diseases containing the HA-MTX conjugate of the invention as active ingredient is administered, 1 to 3 mL of solution thereof may be used at a HA-MTX conjugate concentration of 0.01% to 10% w/v, preferably 0.1% to 2.0% w/v, particularly preferably 0.5% to 1.5% w/v for each administration to a patient. However, the dose may be changed into optimum depending on physician instruction, a subject patient, the type and severity of disease, the molecular weight of the HA-MTX conjugate, and the like.

As described in Examples below, the HA-MTX conjugate of the invention, when intra-articularly administered to an arthritis model in which pathosis occurs in the knee joint, exerts an alleviating effect on synovitis, which is not seen with HA. In addition, the present inventors have found that the alleviating effect on synovitis of a HA-MTX conjugate with a molecular weight of 600,000 daltons or more, particularly 800,000 daltons or more is confirmed to be extremely high compared to that of a HA-MTX conjugate with a lower molecular weight (300,000 daltons).

BEST MODE FOR CARRYING OUT THE INVENTION

Figure 1:
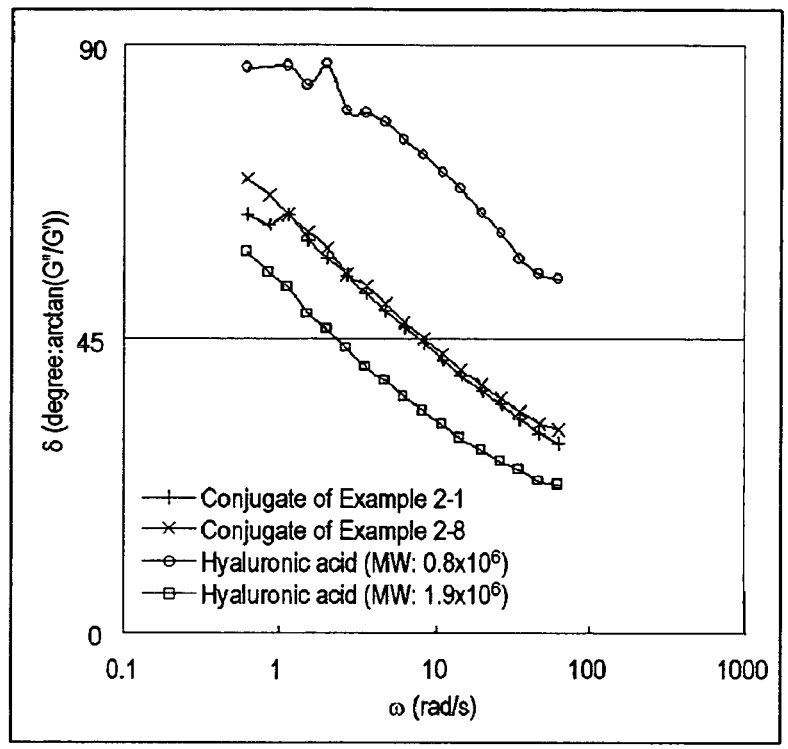
FIG. 1 is a set of graphs showing the result of determining the viscoelasticities of test substances and control substances (hyaluronic acid with a molecular weight of 1900,000 and hyaluronic acid with a molecular weight of 800,000)
Figure 1:
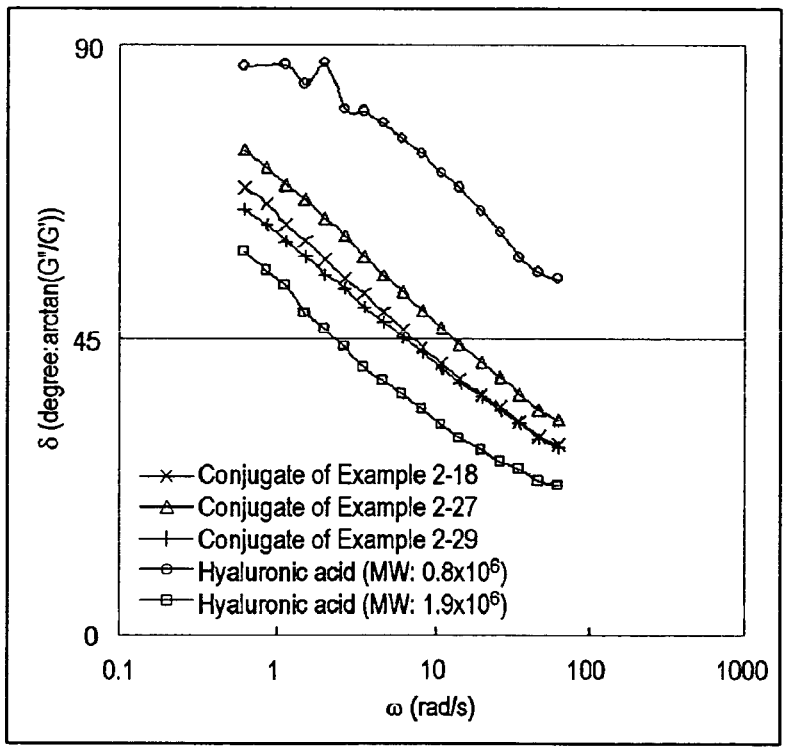

The present invention is described in further detail, based on Examples below. However, the invention is not intended to be limited to these Examples.

EXAMPLES

Example 1-1

Production of 2-[N-[N-[N-[4-[[(2,4-diamino-6-pteridinyl)methyl]methylamino]benzoyl]-α-(O5-methylglutamyl)]phenylalanyl]phenylalanylamino]ethylamine: MTX-α-PhePhe-NH—$C_2H_4$—$NH_2$ (compound 1)

(a) Production of Cbz-Phe-NH—$C_2H_4$—NH-Boc (compound 1a)

N-carbobenzoxy-L-phenylalanine (Cbz-Phe: 7.16 g, 25.4 mmol), N-t-butoxycarbonyl-ethylenediamine hydrochloride (5.00 g, 25.4 mmol), 1-hydroxybenzotriazole hydrate (HOBT: 4.28 g, 28.0 mmol), and N-methylmorpholine (NMM: 3.07 mL, 28.0 mmol) were dissolved in 100 mL of dimethylformamide (DMF), to which 1-ethyl-3-(3-dimethylaminopropyl)carbodiimide hydrochloride (EDC: 5.36 g, 28.0 mmol) was then added under stirring and cooling with ice, followed by stirring at room temperature for one day. A 10% citric acid aqueous solution was added to the reaction solution, and the precipitated solid was dissolved in chloroform and a small amount of methanol, followed by washing the solution with a saturated sodium bicarbonate solution and a saturated saline solution before drying with sodium sulfate. It was concentrated under reduced pressure, followed by purifying the resultant residue using silica gel column chromatography (elution solvent: chloroform:methanol=95:5) to provide 9.69 g of the title compound as a white solid.

$^1$H-NMR (270 MHz, DMSO-$d_6$): δ1.37 (9H, s), 2.69-3.19 (6H, m), 4.12-4.22 (1H, m), 4.93 (2H, dd, J=12.9 Hz, J=15.1 Hz), 6.75 (1H, br.t), 7.22-7.33 (10H, m), 7.48 (1H, d, J=8.6 Hz), 8.05 (1H, br.t)

LC/MS: 441.9 (M+H$^+$) 464.1 (M+Na$^+$)

(b) Production of Cbz-PhePhe-NH—$C_2H_4$—NH-Boc (compound 1b)

Compound 1a (9.69 g, 21.9 mmol) was dissolved in 200 mL of methanol, to which 500 mg of 10% palladium carbon was then added, followed by stirring at room temperature for one day under an atmosphere of hydrogen. The catalyst was filtered off from the reaction mixture, followed by concentration under reduced pressure. This residue, Cbz-Phe (6.92 g, 23.1 mmol), HOBT (3.71 g, 24.2 mmol), and NMM (2.66 mL, 24.2 mmol) were dissolved in 50 mL of dimethylformamide (DMF), to which EDC (4.64 g, 24.2 mmol) was then added under stirring and cooling with ice, followed by stirring at room temperature for one day. Water was added to the reaction solution, which was then washed with a 10% citric acid aqueous solution, a saturated sodium bicarbonate solution, and water before drying. The resultant residue was purified using silica gel column chromatography (elution solvent: chloroform:methanol=90:10) to provide 12.8 g of the title compound as a white solid.

$^1$H-NMR (270 MHz, DMSO-$d_6$): δ1.37 (9H, s), 2.62-3.18 (8H, m), 4.18-4.29 (1H, m), 4.40-4.51 (1H, m), 4.93 (2H, s), 6.72 (1H, br.t), 7.10-7.32 (15H, m), 7.46 (1H, d, J=8.6 Hz), 7.97 (1H, br.t), 8.11 (1H, d, J=7.9 Hz)

LC/MS: 588.8 (M+H$^+$) 611.1 (M+Na$^+$)

(c) Production of Cbz-Glu(OMe)PhePhe-NH—$C_2H_4$—NH-Boc (compound 1c)

Compound 1b (11.1 g, 18.9 mg) was dissolved in 800 mL of methanol, 50 mL of DMF, and 500 mL of THF, to which 1.00 g of 10% palladium carbon was then added, followed by stirring at room temperature for one day under an atmosphere of hydrogen. The catalyst was filtered off from the reaction mixture, followed by concentration under reduced pressure. This residue, N-carbobenzoxy-L-glutamic acid-γ-methyl ester (Cbz-Glu(OMe): 5.58 g, 18.9 mmol), HOBT (3.18 g, 20.8 mmol), and NMM (2.29 mL, 20.8 mmol) were dissolved in 100 mL of DMF, to which EDC (3.99 g, 20.8 mmol) was then added under stirring and cooling with ice, followed by stirring at room temperature for two days. To the reaction solution was added 10% citric acid under stirring and cooling with ice, and the generated precipitate was washed with a 5% sodium bicarbonate solution and water before purification using silica gel column chromatography (elution solvent: dichloromethane:methanol=10:1), followed by adding methanol to generate a precipitate to provide 11.1 g of the title compound as a white powder.

$^1$H-NMR (270 MHz, DMSO-$d_6$): δ1.36 (9H, s), 1.64-1.80 (2H, m), 2.17-2.23 (2H, m), 2.76-3.12 (8H, m), 3.56 (3H, s), 3.93-4.03 (1H, m), 4.40-4.58 (2H, m), 5.00 (2H, s), 6.68 (1H, br.t), 7.18-7.44 (16H, m), 7.84-7.90 (2H, m), 8.19 (1H, d, J=7.7 Hz)

LC/MS: 732.4 (M+H$^+$), 754.4 (M+Na$^+$)

(d) Production of MTX-α-PhePhe-NH—$C_2H_4$—NH-Boc (compound 1d)

Compound 1c (348 mg, 0.476 mmol) was suspended in 10 mL of methanol and 10 mL of tetrahydrofuran, to which 33 mg of 10% palladium carbon was then added, followed by stirring at room temperature for 1.5 hours under an atmosphere of hydrogen. The catalyst was filtered off from the reaction mixture, followed by concentration under reduced pressure. This residue, 4-[N-(2,4-diamino-6-pteridinylmethyl)-N-methylamino]benzoic acid (197 mg, 0.547 mmol), and HOBT (76 mg, 0.499 mmol) were dissolved in 4 mL of N-methylpyrrolidone (NMP), to which N-methylmorpholine (NMM, 55 μL, 0.499 mmol) and EDC (105 mg, 0.547 mmol) were then added under stirring and cooling with ice, followed by stirring at room temperature for 4 days. A 5% sodium bicarbonate solution was added to the reaction solution, and the generated precipitate was purified by silica gel column chromatography (elution solvent: dichloromethane:methanol=10:1) and then amine silica gel (NH-DM1020, 100-200 mesh, from Fuji Silysia Chemical Ltd.) column chromatography (elution solvent: dichloromethane:methanol=10:1) to provide 362 mg of the title compound as a yellow powder.

$^1$H-NMR (270 MHz, DMSO-$d_6$): δ1.35 (9H, s), 1.78-1.94 (2H, m), 2.23 (2H, m), 2.69-3.10 (8H, m), 3.22 (3H, s), 3.55 (3H, s), 4.27-4.52 (3H, m), 4.79 (2H, s), 6.63 (2H, br.s), 6.70 (1H, br.t), 6.82 (2H, d, J=8.9 Hz), 7.06-7.25 (10H, m), 7.46 (1H, br.s), 7.66-7.88 (5H, m), 8.06-8.17 (2H, m), 8.56 (1H, s)

LC/MS: 905.5 (M+H$^+$)

(e) Production of MTX-α-PhePhe-NH—$C_2H_4$—$NH_2$ (compound 1)

To compound 1d (360 mg, 0.398 mmol) was added 5 mL of trifluoroacetic acid under cooling with ice, followed by stirring for one hour. The reaction solution was concentrated under reduced pressure, followed by purifying the residue using amine silica gel column chromatography (elution solvent: dichloromethane:methanol=100:10, twice) to provide 275 mg of the title compound as a yellow powder.

$^1$H-NMR (270 MHz, DMSO-$d_6$): δ1.80-1.96 (2H, m), 2.20-2.28 (2H, m), 2.45 (2H, t, J=6.6 Hz), 2.70-3.10 (6H, m), 3.22 (3H, s), 3.55 (3H, s), 4.26-4.52 (3H, m), 4.79 (2H, s), 6.61 (2H, br.s), 6.82 (2H, d, J=8.7 Hz), 7.06-7.21 (10H, m), 7.46 (1H, br.s), 7.65-7.73 (3H, m), 7.85 (1H, d, J=8.1 Hz), 8.08-8.16 (2H, m), 8.56 (1H, s)

LC/MS: 805.3 (M+H$^+$)

Example 1-2

Production of 4,7,10-trioxa-13-[N-[N-[N-[4-[[(2,4-diamino-6-pteridinyl)methyl]methylamino]benzoyl]-α-(O5-methylglutamyl)]phenylalanyl]phenylalanylamino]tridecanylamine: MTX-α-PhePhe-NH—C$_{10}$H$_{20}$O$_3$—NH$_2$ (compound 2)

(a) Production of Cbz-Phe-NH—C$_{10}$H$_{20}$O$_3$—NH-Boc (compound 2a)

N-carbobenzoxy-L-phenylalanine (Cbz-Phe: 852 mg, 2.85 mmol), N-t-butoxycarbonyl-4,7,10-trioxa-1,13-tridecanediamine (760 mg, 2.37 mmol), and 1-hydroxybenzotriazole hydrate (HOBT: 363 mg, 2.37 mmol) were dissolved in 6 mL of dimethylformamide (DMF), to which 1-ethyl-3-(3-dimethylaminopropyl)carbodiimide hydrochloride (EDC: 546 mg, 2.85 mmol) was then added under stirring and cooling with ice, followed by stirring at room temperature for two days. Ethyl acetate was added to the reaction solution, followed by washing with a 10% citric acid aqueous solution, a 5% sodium bicarbonate solution, and a saturated saline solution before drying with sodium sulfate. It was concentrated under reduced pressure, followed by purifying the resultant residue using silica gel column chromatography (elution solvent: dichloromethane:methanol=100:3) to provide 1.35 g of the title compound as an oily material.

$^1$H-NMR (270 MHz, CDCl$_3$): δ1.43 (9H, s), 1.56-1.74 (4H, m), 3.06 (2H, d, J=6.8 Hz), 3.17-3.58 (16H, m), 4.30-4.39 (1H, m), 4.98 (1H, br), 5.08 (2H, s), 5.50 (1H, br), 6.40 (1H, br), 7.16-7.32 (10H, m)

LC/MS: 624.3 (M+Na$^+$)

(b) Production of Cbz-PhePhe-NH—C$_{10}$H$_{20}$O$_3$—NH-Boc (compound 2b)

Compound 2a (1.35 g, 2.24 mmol) was dissolved in 12 mL of methanol, to which 200 mg of 10% palladium carbon was then added, followed by stirring at room temperature for 4 hours under an atmosphere of hydrogen. The catalyst was filtered off from the reaction mixture, followed by concentration under reduced pressure. This residue, Cbz-Phe (1.07 g, 3.57 mmol) and HOBT (514 mg, 3.36 mmol) were dissolved in 10 mL of DMF, to which EDC (688 mg, 3.59 mmol) was then added under stirring and cooling with ice, followed by stirring at room temperature for two days. Ethyl acetate was added to the reaction solution, which was then washed with a 10% citric acid aqueous solution, a 5% sodium bicarbonate solution, and a saturated saline solution before drying with sodium sulfate. It was concentrated under reduced pressure, followed by purifying the resultant residue using silica gel column chromatography (elution solvent: dichloromethane:methanol=100:3). n-Hexane was added thereto to generate a white precipitate which was then collected by filtration to provide 1.56 g of the title compound.

$^1$H-NMR (270 MHz, CDCl$_3$): δ1.43 (9H, s), 1.60-1.78 (4H, m), 2.96-3.60 (20H, m), 4.42-4.59 (2H, m), 4.96-5.07 (3H, m), 5.41 (1H, br.d), 6.39 (1H, br), 6.73 (1H, br.d), 7.08-7.31 (15H, m)

LC/MS: 771.3 (M+Na$^+$)

(c) Production of Cbz-Glu(OMe)PhePhe-NH—C$_{10}$H$_{20}$O$_3$—NH-Boc (compound 2c)

Compound 2b (500 mg, 0.668 mmol) was dissolved in 10 mL of methanol, to which 150 mg of 10% palladium carbon was then added, followed by stirring at room temperature for one day under an atmosphere of hydrogen. The catalyst was filtered off from the reaction mixture, followed by concentration under reduced pressure. This residue, N-carbobenzoxy-L-glutamic acid-γ-methyl ester (Cbz-Glu(OMe): 217 mg, 0.734 mmol) and HOBT (102 mg, 0.668 mmol) were dissolved in 5 mL of DMF, to which EDC (141 mg, 0.734 mmol) was then added under stirring and cooling with ice, followed by stirring at room temperature for 16 hours. Ethyl acetate was added to the reaction solution, which was then washed with a 10% citric acid aqueous solution, a 5% sodium bicarbonate solution, and a saturated saline solution before drying with sodium sulfate. It was concentrated under reduced pressure, followed by purifying the resultant residue using silica gel column chromatography (elution solvent: dichloromethane:methanol=100:5). n-Hexane was added thereto to generate a white precipitate which was then collected by filtration to provide 529 mg of the title compound.

$^1$H-NMR (270 MHz, DMSO-$d_6$): δ1.36 (9H, s), 1.50-1.85 (6H, m), 2.20 (2H, t, J=7.9 Hz), 2.70-3.10 (8H, m), 3.25-3.48 (12H, m), 3.56 (3H, s), 3.93-4.02 (1H, m), 4.20-4.60 (2H, m), 5.00 (2H, s), 6.77 (1H, br.t), 7.10-7.45 (16H, m), 7.82 (1H, br.t, J=6.1 Hz), 7.91 (1H, d, J=7.9 Hz), 8.22 (1H, d, J=7.9 Hz)

LC/MS: 914.3 (M+Na$^+$)

(d) Production of MTX-α-PhePhe-NH—C$_{10}$H$_{20}$O$_3$—NH-Boc (compound 2d)

Compound 2c (514 mg, 0.576 mmol) was suspended in 30 mL of methanol, to which 100 mg of 10% palladium carbon was then added, followed by stirring at room temperature for 1.5 hours under an atmosphere of hydrogen. The catalyst was filtered off from the reaction mixture, followed by concentration under reduced pressure. This residue, 4-[N-(2,4-diamino-6-pteridinylmethyl)-N-methylamino]benzoic acid (281 mg, 0.864 mmol), and HOBT (132 mg, 0.864 mmol) were dissolved in 5 mL of DMF, to which EDC (166 mg, 0.864 mmol) were then added under stirring and cooling with ice, followed by stirring at room temperature for 2 days. A 5% sodium bicarbonate solution was added to the reaction solution, and the generated precipitate was purified by amine silica gel (NH-DM1020, 100-200 mesh, from Fuji Silysia Chemical Ltd.) column chromatography (elution solvent: 1st elution; dichloromethane:methanol=100:7, 2nd elution; chloroform:methanol=100:4) to provide 415 mg of the title compound as a yellow powder.

$^1$H-NMR (270 MHz, DMSO-$d_6$): δ1.36 (9H, s), 1.48-1.61 (4H, m), 1.81-1.92 (2H, m), 2.24 (2H, t, J=7.9 Hz), 2.70-3.10 (8H, m), 3.22 (3H, s), 3.25-3.47 (12H, m), 3.54 (3H, s), 4.25-4.50 (3H, m), 4.79 (2H, s), 6.61 (2H, br.s), 6.76-6.83 (3H, m), 7.06-7.24 (10H, m), 7.45 (1H, br.s), 7.67-7.80 (4H, m), 7.86 (1H, d, J=8.1 Hz), 8.09 (1H, d, J=7.4 Hz), 8.15 (1H, d, J=8.1 Hz), 8.56 (1H, s)

LC/MS: 1087.5 (M+Na$^+$)

(e) Production of MTX-α-PhePhe-NH—C$_{10}$H$_{20}$O$_3$—NH$_2$ (compound 2)

To compound 2d (413 mg, 0.388 mmol) was added 3 mL of trifluoroacetic acid under cooling with ice, followed by stirring for 40 minutes. The reaction solution was concentrated under reduced pressure, followed by purifying the residue using amine silica gel column chromatography (elution solvent: dichloromethane:methanol=100:7, twice) to provide 344 mg of the title compound as a yellow powder.

$^1$H-NMR (270 MHz, DMSO-$d_6$): δ1.49-1.95 (4H, m), 1.81-1.92 (2H, m), 2.24 (2H, t, J=7.9 Hz), 2.70-3.10 (8H, m), 3.22 (3H, s), 3.25-3.47 (12H, m), 3.54 (3H, s), 4.25-4.50 (3H, m), 4.79 (2H, s), 6.61 (2H, br.s), 6.76-6.83 (3H, m), 7.06-7.24 (10H, m), 7.45 (1H, br.s), 7.83 (1H, br.t, J=5.8 Hz), 8.01 (1H, d, J=7.9 Hz), 8.09 (1H, d, J=7.1 Hz), 8.15 (1H, d, J=7.8 Hz), 8.56 (1H, s)

LC/MS: 965.5 (M+H$^+$)

Example 1-3

Production of MTX-α-PhePhe-NH—C$_{10}$H$_{20}$O$_2$—NH$_2$ (compound 3)

By a method similar to that in Example 1-2 was obtained 221 mg of the title compound as a yellow powder using N-t-butoxycarbonyl-4,9-dioxa-1,12-dodecanediamine in place of N-t-butoxycarbonyl-4,7,10-trioxa-1,13-tridecanediamine.

$^1$H-NMR (400 MHz, DMSO-d$_6$): δ1.47-1.60 (8H, m), 1.80-1.95 (2H, m), 2.20-2.29 (2H, m), 2.60 (2H, t), 2.70-3.10 (6H, m), 3.22 (3H, s), 3.25-3.50 (8H, m), 3.54 (3H, s), 4.25-4.49 (3H, m), 4.79 (2H, s), 6.60 (2H, br.s), 6.81 (2H, d, J=8.4 Hz), 7.06-7.20 (10H, m), 7.45 (1H, br.s), 7.65 (1H, br.s), 7.70 (2H, d), 7.73 (1H, br.t), 7.83 (1H, d), 8.10 (1H, d), 8.11 (1H, d), 8.55 (1H, s)

LC/MS: 949.5 (M+H$^+$)

Example 1-4

Production of MTX-α-PhePhe-NH—C$_8$H$_{16}$O$_2$—NH$_2$ (compound 4)

By a method similar to that in Example 1-2 was obtained 407 mg of the title compound as a yellow powder using N-t-butoxycarbonyl-4,7-dioxa-1,10-decanediamine in place of N-t-butoxycarbonyl-4,7,10-trioxa-1,13-tridecanediamine.

$^1$H-NMR (400 MHz, DMSO-d$_6$): δ1.50-1.57 (4H, m), 1.85-1.91 (2H, m), 2.21-2.28 (2H, m), 2.60 (2H, t), 2.70-3.13 (6H, m), 3.22 (3H, s), 3.25-3.45 (8H, m), 3.55 (3H, s), 4.27-4.49 (3H, m), 4.79 (2H, s), 6.60 (2H, br.s), 6.82 (2H, d, J=8.8 Hz), 7.07-7.21 (10H, m), 7.43 (1H, br.s), 7.69 (1H, br.s), 7.71 (2H, d, J=8.8 Hz), 7.75 (1H, br.t), 7.85 (1H, d), 8.08 (1H, d), 8.13 (1H, d), 8.56 (1H, s)

LC/MS: 921.4 (M+H$^+$)

Example 1-5

Production of MTX-α-PhePhe-NH—C$_6$H$_{12}$O$_2$—NH$_2$ (compound 5)

By a method similar to that in Example 1-2 was obtained 148 mg of the title compound as a yellow powder using N-t-butoxycarbonyl-3,6-dioxa-1,8-octanediamine in place of N-t-butoxycarbonyl-4,7,10-trioxa-1,13-tridecanediamine.

$^1$H-NMR (270 MHz, DMSO-d$_6$): δ1.81-1.91 (2H, m), 2.20-2.25 (2H, m), 2.61-2.64 (2H, t), 2.70-2.97 (6H, m), 3.22 (3H, s), 3.27-3.47 (8H, m), 3.55 (3H, s), 4.27-4.47 (3H, m), 4.79 (2H, s), 6.62 (2H, br.s), 6.82 (2H, d, J=8.7 Hz), 7.06-7.25 (10H, m), 7.46 (1H, br.s), 7.67 (1H, br.s), 7.71 (2H, d, J=8.6 Hz), 7.85 (1H, d), 7.92 (1H, br.t), 8.07 (1H, d), 8.15 (1H, d), 8.56 (1H, s)

LC/MS: 893.6 (M+H$^+$)

Example 1-6

Production of MTX-α-PhePhe-NH—C$_4$H$_8$O—NH$_2$ (compound 6)

By a method similar to that in Example 1-2 was obtained 52 mg of the title compound as a yellow powder using N-t-butoxycarbonyl-3-oxa-1,5-pentanediamine in place of N-t-butoxycarbonyl-4,7,10-trioxa-1,13-tridecanediamine.

$^1$H-NMR (270 MHz, DMSO-d$_6$): δ1.84-1.92 (2H, m), 2.20-2.27 (2H, m), 2.60-2.64 (2H, t), 2.71-2.99 (6H, m), 3.22 (3H, s), 3.25-3.45 (4H, m), 3.54 (3H, s), 4.27-4.50 (3H, m), 4.79 (2H, s), 6.61 (2H, br.s), 6.81 (2H, d, J=8.4 Hz), 7.05-7.21 (10H, m), 7.45 (1H, br.s), 7.65 (1H, br.s), 7.70 (2H, d, J=8.6 Hz), 7.84 (1H, d), 7.91 (1H, br.t), 8.07 (1H, d), 8.15 (1H, d), 8.55 (1H, s)

LC/MS: 849.4 (M+H$^+$)

Example 1-7

Production of MTX-α-PhePhe-NH—C$_5$H$_{10}$—NH$_2$ (compound 7)

By a method similar to that in Example 1-1 was obtained 148 mg of the title compound as a yellow powder using N-t-butoxycarbonyl-1,5-pentanediamine in place of N-t-butoxycarbonyl-1,2-ethylenediamine.

$^1$H-NMR (270 MHz, DMSO-d$_6$): δ1.16-1.56 (6H, m), 1.81-1.97 (2H, m), 2.21-2.29 (2H, m), 2.69-3.06 (6H, m), 3.23 (3H, s), 3.55 (3H, s), 4.25-4.50 (3H, m), 4.80 (2H, s), 6.65 (2H, br.s), 6.82 (2H, d, J=8.6 Hz), 7.08-7.24 (10H, m), 7.50 (1H, br.s), 7.60-7.89 (5H, m), 8.10-8.16 (2H, m), 8.55 (1H, s)

LC/MS: 847.4 (M+H$^+$)

Example 1-8

Production of MTX-α-PhePhe-Lys-OMe (compound 8)

By a method similar to that in Example 1-2 was obtained 178 mg of the title compound as a yellow powder using N-ε-t-butoxycarbonyl-L-lysine methyl ester in place of N-t-butoxycarbonyl-4,7,10-trioxa-1,13-tridecanediamine.

$^1$H-NMR (270 MHz, DMSO-d$_6$): δ1.25-1.34 (4H, m), 1.56-1.69 (2H, m), 1.75-1.90 (2H, m), 2.18-2.25 (2H, br.t), 2.50-2.60 (2H, m), 2.65-3.07 (4H, m), 3.22 (3H, s), 3.54 (3H, s), 3.60 (3H, s), 4.15-4.60 (4H, m), 4.79 (2H, s), 6.63 (2H, br.s), 6.81 (2H, d, J=8.7 Hz), 7.00-7.25 (10H, m), 7.45 (1H, br.s), 7.62 (1H, br.s), 7.69 (2H, d, J=8.6 Hz), 7.80 (1H, d), 8.05 (1H, d), 8.16 (1H, d), 8.30 (1H, d), 8.56 (1H, s)

LC/MS: 905.4 (M+H$^+$)

Example 1-9

Production of MTX-α-PheGly-NH—C$_{10}$H$_{20}$O$_3$—NH$_2$ (compound 9)

In the same way as in Example 1-2 except for the use of N-carbobenzoxyglycine in place of N-carbobenzoxy-L-phenylalanine in the step of Example 1-2(a) was obtained 528 mg of the title compound as a yellow powder.

$^1$H-NMR (270 MHz, DMSO-d$_6$): δ1.51-1.64 (4H, m), 1.84-1.94 (2H, m), 2.21-2.30 (2H, m), 2.55 (2H, t, J=6.3 Hz), 2.78-2.92 (1H, m), 3.03-3.76 (17H, m), 3.22 (3H, s), 3.55 (3H, s), 4.26-4.52 (2H, m), 4.79 (2H, s), 6.63 (2H, br.s), 6.82 (2H, d, J=8.7 Hz), 7.11-7.24 (5H, m), 7.47 (1H, br.s), 7.62-7.72 (4H, m), 8.04-8.16 (2H, m), 8.28 (1H, br.t), 8.56 (1H, s)

LC/MS: 875.5 (M+H$^+$)

Example 1-10

Production of MTX-α-PheGly-NH—C$_{10}$H$_{20}$O$_2$—NH$_2$ (compound 10)

By a method similar to that in Example 1-9 was obtained 300 mg of the title compound as a yellow powder using N-t-butoxycarbonyl-4,9-dioxa-1,12-dodecanediamine in place of N-t-butoxycarbonyl-4,7,10-trioxa-1,13-tridecanediamine.

¹H-NMR (400 MHz, DMSO-d₆): δ1.47-1.50 (4H, m), 1.54-1.60 (4H, m), 1.82-1.95 (2H, m), 2.25-2.28 (2H, m), 2.58 (2H, t, J=6.6 Hz), 2.82-2.87 (1H, m), 3.02-3.07 (3H, m), 3.22 (3H, s), 3.25-3.41 (8H, m), 3.55 (3H, s), 3.55-3.63 (2H, m), 4.28-4.47 (2H, m), 4.79 (2H, s), 6.60 (2H, br.s), 6.81 (2H, d, J=8.8 Hz), 7.09-7.18 (5H, m), 7.45 (1H, br.s), 7.59 (1H, br.t), 7.66 (1H, br.s), 7.70 (2H, d, J=8.8 Hz), 8.02 (1H, d), 8.08 (1H, d), 8.26 (1H, br.t), 8.56 (1H, s)

LC/MS: 859.3 (M+H⁺)

Example 1-11

Production of MTX-α-PheGly-NH—C₈HL₆O₂—NH₂ (compound 11)

By a method similar to that in Example 1-9 was obtained 300 mg of the title compound as a yellow powder using N-t-butoxycarbonyl-4,7-dioxa-1,10-decanediamine in place of N-t-butoxycarbonyl-4,7,10-trioxa-1,13-tridecanediamine.

¹H-NMR (400 MHz, DMSO-d₆): δ1.53-1.62 (4H, m), 1.82-1.92 (2H, m), 2.20-2.27 (2H, m), 2.50-2.60 (2H, t), 2.81-2.86 (1H, m), 2.97-3.08 (3H, m), 3.22 (3H, s), 3.25-3.47 (8H, m), 3.55 (3H, s), 3.55-3.73 (2H, m), 4.24-4.47 (2H, m), 4.79 (2H, s), 6.60 (2H, br.s), 6.81 (2H, d), 7.12-7.21 (5H, m), 7.45 (1H, br.s), 7.60 (1H, br.t), 7.63 (1H, br.s), 7.69 (2H, d), 8.03 (1H, d), 8.10 (1H, d), 8.28 (1H, br.t), 8.56 (1H, s)

LC/MS: 831.3 (M+H⁺)

Example 1-12

Production of MTX-α-PheGly-NH—C₆H₁₂O₂—NH₂ (compound 12)

By a method similar to that in Example 1-9 was obtained 181 mg of the title compound as a yellow powder using N-t-butoxycarbonyl-3,6-dioxa-1,8-octanediamine in place of N-t-butoxycarbonyl-4,7,10-trioxa-1,13-tridecanediamine.

¹H-NMR (270 MHz, DMSO-d₆): δ1.83-1.92 (2H, m), 2.21-2.27 (2H, m), 2.60-2.65 (2H, t), 2.75-3.10 (2H, m), 3.22 (3H, s), 3.23-3.46 (10H, m), 3.55 (3H, s), 3.55-3.75 (2H, m), 4.25-4.52 (2H, m), 4.79 (2H, s), 6.61 (2H, br.s), 6.82 (2H, d, J=8.6 Hz), 7.10-7.20 (5H, m), 7.45 (1H, br.s), 7.63-7.72 (4H, m), 8.00 (1H, d), 8.10 (1H, d), 8.27 (1H, br.t), 8.56 (1H, s)
LC/MS: 803.4 (M+H⁺)

Example 1-13

Production of MTX-α-PheGly-NH—C₄H₈O—NH₂ (compound 13)

By a method similar to that in Example 1-9 was obtained 318 mg of the title compound as a yellow powder using N-t-butoxycarbonyl-3-oxa-1,5-pentanediamine in place of N-t-butoxycarbonyl-4,7,10-trioxa-1,13-tridecanediamine.

¹H-NMR (270 MHz, DMSO-d₆): δ1.82-1.95 (2H, m), 2.22-2.27 (2H, m), 2.59-2.64 (2H, t), 2.73-3.15 (2H, m), 3.23 (3H, s), 3.25-3.38 (6H, m), 3.55 (3H, s), 3.46-3.77 (2H, m), 4.23-4.51 (2H, m), 4.79 (2H, s), 6.62 (2H, br.s), 6.82 (2H, d, J=8.6 Hz), 7.10-7.17 (5H, m), 7.47 (1H, br.s), 7.63-7.75 (4H, m), 8.02 (1H, d), 8.11 (1H, d), 8.27 (1H, br.t), 8.56 (1H, s)

LC/MS: 759.3 (M+H⁺)

Example 1-14

Production of MTX-α-PhePro-NH—C₁₀H₂₀O₃—NH₂ (compound 14)

In the same way as in Example 1-2 except for the use of N-carbobenzoxy-L-proline in place of N-carbobenzoxy-L-phenylalanine in the step of Example 1-2(a) was obtained 382 mg of the title compound as a yellow powder.

¹H-NMR (270 MHz, DMSO-d₆): δ1.49-2.03 (10H, m), 2.19-2.30 (2H, m), 2.55 (2H, t, J=6.6 Hz), 2.62-3.69 (21H, m), 3.55 (3H, s), 4.28-4.38 (1H, m), 4.63-4.75 (1H, m), 4.79 (2H, s), 6.60 (2H, br.s), 6.82 (2H, d, J=8.6 Hz), 7.14-7.29 (5H, m), 7.47 (1H, br.s), 7.66-7.72 (4H, m), 7.94-8.10 (2H, m), 8.56 (1H, s)

LC/MS: 915.3 (M+H⁺)

Example 1-15

Production of MTX-α-PheβAla-NH—C₁₀H₂₀O₃—NH₂ (compound 15)

In the same way as in Example 1-2 except for the use of N-carbobenzoxy-β-alanine in place of N-carbobenzoxy-L-phenylalanine in the step of Example 1-2(a) was obtained 180 mg of the title compound as a yellow powder.

¹H-NMR (270 MHz, DMSO-d₆): δ1.52-1.62 (4H, m), 1.78-1.95 (2H, m), 2.16-2.22 (4H, m), 2.56 (2H, t, J=7.3 Hz), 2.71-3.48 (21H, m), 3.55 (3H, s), 4.10 (2H, br.s), 4.21-4.30 (1H, m), 4.38-4.49 (1H, m), 4.80 (2H, s), 6.59 (2H, br.s), 6.83 (2H, d, J=8.6 Hz), 7.10-7.21 (5H, m), 7.43 (1H, br.s), 7.65-7.74 (3H, m), 7.83-7.89 (2H, m), 7.96 (1H, br.t), 8.08 (1H, d, J=6.8 Hz), 8.56 (1H, s)

LC/MS: 889.5 (M+H⁺)

Example 1-16

Production of MTX-α-PheβAla-NH—C₂H₄—NH₂ (compound 16)

In the same way as in Example 1-1 except for the use of N-carbobenzoxy-β-alanine in place of N-carbobenzoxy-L-phenylalanine in the step of Example 1-1(a) was obtained 194 mg of the title compound as a yellow powder.

¹H-NMR (270 MHz, DMSO-d₆): δ1.80-1.94 (2H, m), 2.18-2.26 (4H, m), 2.54 (2H, t, J=6.1 Hz), 2.74-3.08 (6H, m), 3.23 (3H, s), 3.55 (3H, s), 4.24-4.48 (2H, m), 4.80 (2H, s), 6.59 (2H, br.s), 6.83 (2H, d, J=8.4 Hz), 7.13 (5H, s), 7.45 (1H, br.s), 7.65-7.86 (5H, m), 7.96 (1H, br.t), 8.09 (1H, d, J=6.8 Hz), 8.56 (1H, s)

LC/MS: 729.3 (M+H⁺)

Example 1-17

Production of MTX-α-Phe-NH—C₁₀H₂₀O₃—NH₂ (compound 17)

In the same way as in Example 1-2 except for the omission of the step of Example 1-2(b) was obtained 496 mg of the title compound as a yellow powder.

¹H-NMR (300 MHz, DMSO-d₆): δ1.49-1.59 (4H, m), 1.82-1.89 (2H, m), 2.19-2.27 (2H, m), 2.55 (2H, t, J=7.2 Hz), 2.73-3.10 (4H, m), 3.23 (3H, s), 3.17-3.48 (12H, m), 3.55 (3H, s), 4.21-4.28 (1H, m), 4.38-4.45 (1H, m), 4.80 (2H, s), 6.61 (2H, br.s), 6.83 (2H, d, J=9.3 Hz), 7.11-7.20 (5H, m), 7.46 (1H, br.s), 7.66 (1H, br.s), 7.73 (2H, d, J=9.0 Hz), 7.83 (1H, t), 7.92 (1H, d, J=8.4 Hz), 8.12 (1H, d, J=7.5 Hz), 8.56 (1H, s)

LC/MS: 818.4 (M+H⁺)

Example 1-18

Production of MTX-α-Ile-NH—C₁₀H₂₀O₃—NH₂ (compound 18)

By a method similar to that in Example 1-17 was obtained 562 mg of the title compound as a yellow powder using N-carbobenzoxy-L-isoleucine in place of N-carbobenzoxy-L-phenylalanine.

¹H-NMR (270 MHz, DMSO-d₆): δ0.76-0.80 (6H, m), 0.99-1.10 (1H, m), 1.36-1.45 (1H, m), 1.49-1.73 (5H, m), 1.88-2.07 (2H, m), 2.33-2.38 (2H, m), 2.55 (2H, t, J=6.6 Hz), 2.98-3.48 (14H, m), 3.21 (3H, s), 3.56 (3H, s), 4.05-4.13 (1H, m), 4.40-4.48 (1H, m), 4.78 (2H, s), 6.60 (2H, br.s), 6.82 (2H, d, J=8.4 Hz), 7.46 (1H, br.s), 7.66-7.72 (3H, m), 7.98 (1H, br.t), 8.12 (1H, d, J=7.6 Hz), 8.56 (1H, s)

LC/MS: 784.4 (M+H$^+$)

Example 1-19

Production of MTX-α-Ile-NH—C$_2$H$_4$—NH$_2$ (compound 19)

By a method similar to that in Example 1-18 was obtained 320 mg of the title compound as a yellow powder using N-t-butoxycarbonyl-1,2-ethylenediamine in place of N-t-butoxycarbonyl-4,7,10-trioxa-1,13-tridecanediamine.

¹H-NMR (300 MHz, DMSO-d₆): δ0.76-0.80 (6H, m), 0.96-1.08 (1H, m), 1.34-1.48 (1H, m), 1.62-1.70 (1H, m), 1.85-2.03 (2H, m), 2.36 (2H, t, J=7.8 Hz), 2.95-3.08 (2H, m), 3.21 (3H, s), 3.56 (3H, s), 4.06-4.12 (1H, m), 4.38-4.45 (1H, m), 4.78 (2H, s), 6.61 (2H, br.s), 6.83 (2H, d, J=9.0 Hz), 7.43 (1H, br.s), 7.64-7.72 (4H, m), 7.92 (1H, t, J=5.7 Hz), 8.12 (1H, d, J=7.5 Hz), 8.57 (1H, s).

LC/MS: 624.2 (M+H$^+$)

Example 1-20

Production of MTX-α-Glu(OMe)-NH—C$_{10}$H$_{20}$O$_3$—NH$_2$ (compound 20)

By a method similar to that in Example 1-17 was obtained 600 mg of the title compound as a yellow powder using N-carbobenzoxy-L-glutamic acid-γ-methyl ester in place of N-carbobenzoxy-L-phenylalanine.

¹H-NMR (270 MHz, DMSO-d₆): δ1.50-2.03 (8H, m), 2.24-2.31 (2H, t), 2.34-2.40 (2H, t), 2.49-2.57 (2H, t), 2.97-3.52 (14H, m), 3.21 (3H, s), 3.53 (3H, s), 3.55 (3H, s), 4.15-4.36 (2H, m), 4.78 (2H, s), 6.61 (2H, br.s), 6.81 (2H, d, J=8.7 Hz), 7.46 (1H, br.s), 7.67 (1H, br.s), 7.72 (2H, d, J=8.6 Hz), 7.84 (1H, br.t), 7.95 (1H, d), 8.14 (1H, d), 8.55 (1H, s)

LC/MS: 814.4 (M+H$^+$)

Example 1-21

Production of MTX-α-Glu(OMe)-NH—C$_2$H$_4$—NH$_2$ (compound 21)

By a method similar to that in Example 1-20 was obtained 283 mg of the title compound as a yellow powder using N-t-butoxycarbonyl-1,2-ethylenediamine in place of N-t-butoxycarbonyl-4,7,10-trioxa-1,13-tridecanediamine.

¹H-NMR (270 MHz, DMSO-d₆): δ1.71-2.09 (4H, m), 2.28 (2H, t, J=7.6 Hz), 2.39 (2H, t, J=7.6 Hz), 2.53 (2H, t, J=6.1 Hz), 2.99-3.05 (2H, m), 3.21 (3H, s), 3.54 (3H, s), 3.56 (3H, s), 4.14-4.36 (2H, m), 4.79 (2H, s), 6.61 (2H, br.s), 6.82 (2H, d, J=8.6 Hz), 7.43 (1H, br.s), 7.65-7.79 (4H, m), 7.95 (1H, d, J=7.8 Hz), 8.14 (1H, d, J=6.9 Hz), 8.56 (1H, s)

LC/MS: 654.1 (M+H$^+$)

Example 1-22

Production of MTX-α-Tyr-NH—C$_{10}$H$_{20}$O$_3$—NH$_2$ (compound 22)

By a method similar to that in Example 1-17 was obtained 133 mg of the title compound as a yellow powder using N-carbobenzoxy-L-tyrosine in place of N-carbobenzoxy-L-phenylalanine.

¹H-NMR (270 MHz, DMSO-d₆): δ1.51-1.62 (4H, m), 1.85-1.95 (2H, m), 2.23-2.31 (2H, m), 2.51-2.58 (2H, t), 2.63-2.91 (2H, m), 2.95-3.16 (2H, m), 3.22 (3H, s), 3.27-3.54 (12H, m), 3.56 (3H, s), 4.22-4.35 (2H, m), 4.79 (2H, s), 6.57 (2H, d, J=8.1 Hz), 6.61 (2H, br.s), 6.82 (2H, d, J=8.7 Hz), 6.92 (2H, d, J=8.1 Hz), 7.47 (1H, br.s), 7.67-7.88 (5H, m), 8.13 (1H, d), 8.55 (1H, s)

LC/MS: 834.4 (M+H$^+$)

Example 1-23

Production of MTX-α-Trp-NH—C$_{10}$H$_{20}$O$_3$—NH$_2$ (compound 23)

By a method similar to that in Example 1-17 was obtained 171 mg of the title compound as a yellow powder using N-carbobenzoxy-L-tryptophan in place of N-carbobenzoxy-L-phenylalanine.

¹H-NMR (270 MHz, DMSO-d₆): δ1.50-1.61 (4H, m), 1.84-1.97 (2H, m), 2.23-2.32 (2H, m), 2.50-2.56 (2H, t), 2.92-3.15 (4H, m), 3.22 (3H, s), 3.29-3.45 (12H, m), 3.55 (3H, s), 4.29-4.49 (2H, m), 4.78 (2H, s), 6.64 (2H, br.s), 6.80 (2H, d), 6.92 (1H, t), 7.04 (1H, t), 7.10 (1H, s), 7.26 (1H, d), 7.44 (1H, br.s), 7.51 (1H, d), 7.65 (1H, br.s), 7.69 (2H, d), 7.82 (1H, br.t), 7.93 (1H, d), 8.10 (1H, d), 8.55 (1H, s), 10.80 (1H, s)

LC/MS: 857.5 (M+H$^+$)

Example 1-24

Production of MTX-α-Ser-NH—C$_{10}$H$_{20}$O$_3$—NH$_2$ (compound 24)

By a method similar to that in Example 1-17 was obtained 416 mg of the title compound as a yellow powder using N-carbobenzoxy-L-serine in place of N-carbobenzoxy-L-phenylalanine.

¹H-NMR (300 MHz, DMSO-d₆): δ1.50-1.63 (4H, m), 1.90-2.08 (4H, m), 2.39 (2H, t, J=7.8 Hz), 2.55 (2H, t, J=6.6 Hz), 3.05-3.48 (16H, m) 3.21 (3H, s), 3.56 (3H, s), 4.13-4.20 (1H, m), 4.33-4.41 (1H, m), 4.78 (2H, s), 6.61 (2H, br.s), 6.82 (2H, d, J=9.0 Hz), 7.44 (1H, br.s), 7.66-7.80 (5H, m), 8.19 (1H, d, J=6.9 Hz), 8.56 (1H, s)

LC/MS: 758.4 (M+H$^+$)

Example 1-25

Production of MTX-α-Leu-NH—C$_{10}$H$_{20}$O$_3$—NH$_2$ (compound 25)

By a method similar to that in Example 1-17 was obtained 283 mg of the title compound as a yellow powder using N-carbobenzoxy-L-leucine in place of N-carbobenzoxy-L-phenylalanine.

¹H-NMR (270 MHz, DMSO-d₆): δ0.80-0.87 (6H, d), 1.43-1.64 (7H, m), 1.90-2.06 (2H, m), 2.34-2.30 (2H, t), 2.53-2.58 (2H, t), 3.04-3.08 (2H, m), 3.21 (3H, s), 3.33-3.47 (12H, m), 3.56 (3H, s), 4.19-4.37 (2H, m), 4.78 (2H, s), 6.62 (2H, br.s), 6.82 (2H, d, J=8.7 Hz), 7.45 (1H, br.s), 7.64-7.85 (5H, m), 8.10 (1H, d), 8.55 (1H, s)

LC/MS: 784.4 (M+H$^+$)

Example 1-26

Production of MTX-α-Val-NH—C$_{10}$H$_{20}$O$_3$—NH$_2$ (compound 26)

By a method similar to that in Example 1-17 was obtained 590 mg of the title compound as a yellow powder using N-carbobenzoxy-L-valine in place of N-carbobenzoxy-L-phenylalanine.

¹H-NMR (270 MHz, DMSO-d₆): δ0.79 (6H, d, J=6.8 Hz), 1.52-1.59 (4H, m), 1.85-2.04 (3H, m), 2.33-2.35 (2H, t), 2.56-2.58 (2H, t), 2.93-3.55 (14H, m), 3.21 (3H, s), 3.56 (3H, s), 4.03-4.08 (1H, m), 4.42-4.47 (1H, m), 4.78 (2H, s), 6.62 (2H, br.s), 6.82 (2H, d, J=8.7 Hz), 7.45 (1H, br.s), 7.61-7.72 (4H, m), 7.98 (1H, br.t), 8.13 (1H, d), 8.56 (1H, s)

LC/MS: 770.4 (M+H⁺)

Example 1-27

Production of MTX-α-His-NH—C₁₀H₂₀O₃—NH₂ (compound 27)

By a method similar to that in Example 1-17 was obtained 81 mg of the title compound as a yellow powder using N-carbobenzoxy-L-histidine in place of N-carbobenzoxy-L-phenylalanine.

¹H-NMR (300 MHz, DMSO-d₆): δ1.49-1.58 (4H, m), 1.90-2.04 (2H, m), 2.39 (2H, t, J=6.6 Hz), 2.55 (2H, t, J=6.9 Hz), 2.83 (2H, m), 3.02 (2H, m), 3.16-3.47 (12H, m), 3.23 (3H, s), 3.57 (3H, s), 4.22 (1H, m), 4.32 (1H, m), 4.80 (2H, s), 6.61 (2H, br.s), 6.72 (1H, s), 6.84 (2H, d, J=8.4 Hz), 7.10-7.70 (5H, m), 7.77 (2H, d, J=8.7 Hz), 8.36 (1H, br), 8.57 (1H, s)

LC/MS: 808.3 (M+H⁺)

Example 1-28

Production of MTX-α-Pro-NH—C₁₀H₂₀O₃—NH₂ (compound 28)

By a method similar to that in Example 1-17 was obtained 683 mg of the title compound as a yellow powder using N-carbobenzoxy-L-proline in place of N-carbobenzoxy-L-phenylalanine.

¹H-NMR (270 MHz, DMSO-d₆): δ1.58 (4H, dd, J=6.5 Hz, J=12.8 Hz), 1.69-2.10 (6H, m), 2.44 (2H, t, J=7.7 Hz), 2.60 (2H, t, J=6.8 Hz), 2.91-3.75 (19H, m), 3.57 (3H, s), 4.18-4.25 (1H, m), 4.61-4.72 (1H, m), 4.77 (2H, s), 6.61 (2H, br.s), 6.80 (2H, d, J=8.7 Hz), 7.44 (1H, br.s), 7.69-7.80 (4H, m), 8.15 (1H, d, J=7.1 Hz), 8.55 (1H, s)

LC/MS: 768.3 (M+H⁺)

Example 1-29

Production of MTX-α-βAla-NH—C₁₀H₂₀O₃—NH₂ (compound 29)

By a method similar to that in Example 1-17 was obtained 230 mg of the title compound as a yellow powder using N-carbobenzoxy-β-alanine in place of N-carbobenzoxy-L-phenylalanine.

¹H-NMR (270 MHz, DMSO-d₆): δ1.49-1.62 (4H, m), 1.79-2.02 (2H, m), 2.21 (2H, t, J=6.9 Hz), 2.32 (2H, t, J=7.3 Hz), 2.56 (2H, t, J=6.6 Hz), 3.00-3.61 (19H, m), 3.55 (3H, s), 4.29-4.38 (1H, m), 4.78 (2H, s), 6.61 (2H, br.s), 6.81 (2H, d, J=8.6 Hz), 7.43 (1H, br.s), 7.61-7.91 (3H, m), 7.72 (2H, d, J=8.6 Hz), 8.02 (1H, d, J=7.8 Hz), 8.55 (1H, s)

LC/MS: 742.4 (M+H⁺)

Example 1-30

Production of MTX-γ-PhePhe-NH—C₁₀H₂₀O₃—NH₂ (compound 30)

By a method similar to that in Example 1-2 was obtained 312 mg of the title compound as a yellow powder using N-carbobenzoxy-L-glutamic acid-α-methyl ester in place of N-carbobenzoxy-L-glutamic acid-γ-methyl ester.

¹H-NMR (270 MHz, DMSO-d₆): δ1.49-1.60 (4H, m), 1.76-1.98 (2H, m), 2.09-2.20 (2H, m), 2.56 (2H, t, J=6.6 Hz), 2.62-3.16 (6H, m), 3.21 (3H, s), 3.27-3.48 (12H, m), 3.59 (3H, s), 4.27-4.53 (3H, m), 4.78 (2H, s), 6.61 (2H, br.s), 6.81 (2H, d, J=8.6 Hz), 7.16-7.23 (10H, m), 7.48 (1H, br.s), 7.68-7.74 (3H, m), 7.83 (1H, br.t), 8.01 (1H, d, J=7.9 Hz), 8.10 (1H, d, J=7.8 Hz), 8.36 (1H, d, J=6.8 Hz), 8.55 (1H, s)

LC/MS: 965.5 (M+H⁺)

Example 1-31

Production of MTX-γ-PhePhe-NH—C₆H₁₂O₂—NH₂ (compound 31)

By a method similar to that in Example 1-5 was obtained 80 mg of the title compound as a yellow powder using N-carbobenzoxy-L-glutamic acid-α-methyl ester in place of N-carbobenzoxy-L-glutamic acid-γ-methyl ester.

¹H-NMR (270 MHz, DMSO-d₆): δ1.75-1.97 (2H, m), 2.08-2.17 (2H, m), 2.59-2.62 (2H, t), 2.58-3.05 (6H, m), 3.22 (3H, s), 3.15-3.52 (8H, m), 3.59 (3H, s), 4.23-4.52 (3H, m), 4.78 (2H, s), 6.63 (2H, br.s), 6.81 (2H, d, J=8.7 Hz), 7.11-7.21 (10H, m), 7.44 (1H, br.s), 7.65 (1H, br.s), 7.70 (2H, d), 7.94-8.12 (3H, m), 8.35 (1H, d), 8.55 (1H, s)

LC/MS: 893.5 (M+H⁺)

Example 1-32

Production of MTX-γ-PhePhe-NH—C₄H₈O—NH₂ (compound 32)

By a method similar to that in Example 1-6 was obtained 49 mg of the title compound as a yellow powder using N-carbobenzoxy-L-glutamic acid-α-methyl ester in place of N-carbobenzoxy-L-glutamic acid-γ-methyl ester.

¹H-NMR (270 MHz, DMSO-d₆): δ1.73-1.97 (2H, m), 2.08-2.18 (2H, m), 2.60-2.65 (2H, t), 2.59-3.02 (6H, m), 3.21 (3H, s), 3.13-3.44 (4H, m), 3.59 (3H, s), 4.25-4.53 (3H, m), 4.78 (2H, s), 6.63 (2H, br.s), 6.81 (2H, d, J=8.7 Hz), 7.09-7.25 (10H, m), 7.43 (1H, br.s), 7.66 (1H, br.s), 7.72 (2H, d, J=8.4 Hz), 7.95-8.10 (3H, m), 8.36 (1H, d), 8.55 (1H, s)

LC/MS: 849.5 (M+H⁺)

Example 1-33

Production of MTX-γ-PheGly-NH—C₁₀H₂₀O₃—NH₂ (compound 33)

By a method similar to that in Example 1-9 was obtained 693 mg of the title compound as a yellow powder using N-carbobenzoxy-L-glutamic acid-α-methyl ester in place of N-carbobenzoxy-L-glutamic acid-γ-methyl ester.

¹H-NMR (270 MHz, DMSO-d₆): δ1.50-1.68 (4H, m), 1.80-2.02 (2H, m), 2.12-2.27 (2H, m), 2.55 (2H, t, J=6.4 Hz), 2.71-2.79 (1H, m), 2.96-3.14 (3H, m), 3.22 (3H, s), 3.38-3.74 (12H, m), 3.59 (3H, s), 4.28-4.48 (2H, m), 4.79 (2H, s), 6.62 (2H, br.s), 6.81 (2H, d, J=8.4 Hz), 7.14-7.28 (5H, m), 7.47 (1H, br.s), 7.63-7.73 (4H, m), 8.19 (1H, d, J=7.6 Hz), 8.29-8.36 (2H, m), 8.56 (1H, s)

LC/MS: 875.4 (M+H⁺)

Example 1-34

Production of MTX-γ-Phe-NH—C₁₀H₂₀O₃—NH₂ (compound 34)

By a method similar to that in Example 1-17 was obtained 480 mg of the title compound as a yellow powder using N-carbobenzoxy-L-glutamic acid-α-methyl ester in place of N-carbobenzoxy-L-glutamic acid-γ-methyl ester.

¹H-NMR (300 MHz, DMSO-d₆): δ1.49-1.58 (4H, m), 1.79-2.00 (2H, m), 2.10-2.27 (2H, m), 2.55 (2H, t, J=6.9 Hz), 2.69-2.93 (2H, m), 2.96-3.12 (2H, m), 3.22 (3H, s), 3.26-3.48 (12H, m), 3.59 (3H, s), 4.25-4.33 (1H, m), 4.38-4.46 (1H, m), 4.79 (2H, s), 6.62 (2H, br.s), 6.81 (2H, d, J=8.7 Hz), 7.10-7.24 (5H, m), 7.44 (1H, br), 7.70 (1H, br), 7.72 (2H, d, J=8.7 Hz), 7.95 (1H, t), 8.10 (1H, d, J=8.1 Hz), 8.35 (1H, d, J=6.9 Hz), 8.56 (1H, s)

LC/MS: 818.4 (M+H$^+$)

Example 1-35

Production of MTX-γ-Glu(OMe)-NH—C$_{10}$H$_{20}$O$_3$—NH$_2$ (compound 35)

By a method similar to that in Example 1-20 was obtained 438 mg of the title compound as a yellow powder using N-carbobenzoxy-L-glutamic acid-α-methyl ester in place of N-carbobenzoxy-L-glutamic acid-γ-methyl ester.

$^1$H-NMR (270 MHz, DMSO-d$_6$): δ1.52-2.06 (8H, m), 2.22-2.30 (4H, m), 2.53-2.58 (2H, t), 3.03-3.15 (2H, m), 3.22 (3H, s), 3.25-3.54 (12H, m), 3.56 (3H, s), 3.61 (3H, s), 4.13-4.40 (2H, m), 4.79 (2H, s), 6.63 (2H, br.s), 6.81 (2H, d, J=8.6 Hz), 7.44 (1H, br.s), 7.67 (1H, br.s), 7.72 (2H, d, J=8.4 Hz), 7.90 (1H, br.t), 7.99 (1H, d), 8.37 (1H, d), 8.56 (1H, s)

LC/MS: 814.5 (M+H$^+$)

Example 1-36

Production of MTX-α-D-Phe-D-Phe-NH—C$_{10}$H$_{20}$O$_3$—NH$_2$ (compound 36)

By a method similar to that in Example 1-2 was obtained 313 mg of the title compound as a yellow powder using N-carbobenzoxy-D-phenylalanine in place of N-carbobenzoxy-L-phenylalanine.

$^1$H-NMR (270 MHz, DMSO-d$_6$): δ1.40-1.59 (4H, m), 1.74-1.83 (2H, m), 2.04-2.11 (2H, m), 2.56-2.58 (2H, t), 2.59-3.12 (6H, m), 3.21 (3H, s), 3.17-3.51 (12H, m), 3.55 (3H, s), 4.24-4.44 (3H, m), 4.78 (2H, s), 6.62 (2H, br.s), 6.81 (2H, d, J=8.6 Hz), 7.10-7.26 (10H, m), 7.45 (2H, m), 7.64 (1H, br.s), 7.72 (2H, d, J=8.4 Hz), 8.18 (2H, m), 8.43 (1H, d), 8.55 (1H, s)

LC/MS: 965.6 (M+H$^+$)

Example 1-37

Production of MTX-γ-D-Phe-D-Phe-NH—C$_{10}$H$_{20}$O$_3$—NH$_2$ (compound 37)

By a method similar to that in Example 1-30 was obtained 85 mg of the title compound as a yellow powder using N-carbobenzoxy-D-phenylalanine in place of N-carbobenzoxy-L-phenylalanine.

$^1$H-NMR (270 MHz, DMSO-d$_6$): δ1.51-1.61 (4H, m), 1.74-2.02 (2H, m), 2.11-2.16 (2H, m), 2.54-2.59 (2H, t), 2.62-3.12 (6H, m), 3.22 (3H, s), 3.25-3.53 (12H, m), 3.60 (3H, s), 4.31-4.46 (3H, m), 4.79 (2H, s), 6.61 (2H, br.s), 6.81 (2H, d, J=8.6 Hz), 7.08-7.26 (10H, m), 7.44 (1H, br.s), 7.66-7.77 (4H, m), 8.06 (2H, m), 8.36 (1H, d), 8.56 (1H, s)

LC/MS: 965.6 (M+H$^+$)

Example 1-38

Production of MTX-α-AsnPhePhe-NH—C$_{10}$H$_{20}$O$_3$—NH$_2$ (compound 38)

By a method similar to that in Example 1-2 was obtained 145 mg of the title compound as a yellow powder, elongating the peptide chain according to a conventional peptide synthesis method.

$^1$H-NMR (270 MHz, DMSO-d$_6$): δ1.52-1.59 (4H, m), 1.87-2.02 (2H, m), 2.32-3.48 (24H, m), 3.22 (3H, s), 3.55 (3H, s), 4.24-4.56 (4H, m), 4.79 (2H, s), 6.60 (2H, br.s), 6.81 (2H, d, J=8.6 Hz), 7.04-7.75 (17H, m), 8.07-8.26 (4H, m), 8.56 (1H, s)

LC/MS: 1079.5 (M+H$^+$)

Example 1-39

Production of MTX-α/γ-GlyPheLeuGly-NH—C$_{10}$H$_{20}$O$_3$—NH$_2$ (compound 39)

By a method similar to that in Example 1-2 was obtained 723 mg of the compound as a yellow powder, elongating the peptide chain according to a conventional peptide synthesis method. It was confirmed, using an LC/MS analysis, that isomerization occurred during purification to generate a mixture of α and γ (α:γ=3:1) (compound 39).

LC/MS: 1045.7 (M+H$^+$)

Example 2-1

Production of MTX-α-PhePhe-NHC$_2$H$_4$NH-HA

A solution consisting of 3-hydroxy-3,4-dihydro-4-oxo-1,2,3-benzotriazine (HOOBt) (0.125 mmol) and compound 1 (0.031 mmol) obtained in Example 1-1 dissolved in an equal quantity mixture (20 ml) of extrapure water and tetrahydrofuran (THF) was added to a suspension in which THF (10 ml) was added to sodium hyaluronate (500 mg, molecular weight: about 2,300,000), to which a solution consisting of tris[2-(2-methoxyethoxy)ethyl]amine (0.094 mmol) dissolved in an equal quantity mixture (10 ml) of extrapure water and THF was then added, followed by stirring at 5° C. A solution consisting of 1-ethyl-3-(3-dimethylaminopropyl)carbodiimide hydrochloride (EDC) (0.125 mmol) dissolved in extrapure water (10 ml) was added 30 minutes after the start of the stirring, followed by stirring at 5° C. for 20 hours. A 0.09N sodium hydroxide aqueous solution (220 ml) was added to the reaction solution, followed by stirring at 5° C. for 3.5 hours. To this solution was added 1N hydrochloric acid (20 ml) for neutralization, to which a solution consisting of sodium chloride (9 g) dissolved in extrapure water (45 ml) was further added, followed by dropwise adding ethanol (600 ml) for ethanol precipitation before separating the precipitate by centrifugation. The precipitate was dissolved in extrapure water (40 ml) to provide an aqueous solution of the title HA-MTX conjugate. The molecular weight thereof as determined by a gel filtration technique using hyaluronic acid as a standard substance was about 1,950,000. The conjugation rate of MTX in the resultant conjugate was 2.1% when calculated by measuring ultraviolet absorption (259 nm).

Sodium chloride (6 g) dissolved in extrapure water (160 mL) was added to the above aqueous solution, to which ethanol (400 mL) was then added dropwise for ethanol precipitation, followed by separating the precipitate through centrifugation. The precipitate was dissolved in extrapure water (500 mL), to which sodium chloride (15 g) was then added before filtration using a 0.45 μm filter (Stervex HV: Millipore), and then ethanol (1000 mL) was aseptically added dropwise to the filtrate for ethanol precipitation, followed by collecting the precipitate by filtration before vacuum drying. This precipitate was dissolved in a phosphate buffer solution (2 mM sodium phosphate, 154 mM sodium chloride, pH 7.2) (40 mL) to provide a sterile aqueous solution of the title HA-MTX conjugate. The molecular weight thereof as determined by a gel filtration technique using hyaluronic acid as a standard substance was about 1,860,000. The conjugation rate of MTX in the resultant conjugate was 2.1% when calculated by measuring ultraviolet absorption (259 nm).

$^1$H-NMR (500 MHz, D$_2$O): δ1.83 (m), 2.01 (br.s), 2.13 (m), 2.49 (m), 2.68 (m), 2.95 (m), 3.35 (br.s), 3.51 (br.s), 3.56 (br.s), 3.71 (br.s), 3.82 (br.s), 4.16 (t), 4.46 (br.s), 4.54 (br.d), 4.88 (d), 4.99 (d), 6.63 (d), 6.87-7.11 (m), 7.73 (d), 8.69 (s)

Example 2-2

Production of MTX-α-PhePhe-NHC$_2$H$_4$NH-HA

Sodium hyaluronate (500 mg, molecular weight: about 2,300,000) was reacted, by a method similar to Example 2-1, with compound 1 (0.031 mmol) obtained in Example 1-1 to provide an aqueous solution of the title HA-MTX conjugate. As determined by the same methods as in Example 2-1, the molecular weight thereof and the conjugation rate of MTX therein were about 2,280,000 and 1.9%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 2,180,000 and 1.9%, respectively.

$^1$H-NMR (500 MHz, D$_2$O): δ1.84 (m), 2.01 (br.s), 2.13 (m), 2.49 (t), 2.68 (m), 2.95 (m), 3.36 (br.d), 3.51 (br.d), 3.56 (br.s), 3.71 (br.s), 3.83 (br.s), 4.16 (t), 4.46 (br.d), 4.55 (br.d), 4.88 (d), 4.98 (d), 6.63 (d), 6.87-7.13 (m), 7.74 (d), 8.70 (s)

Example 2-2'

Production of MTX-α-PhePhe-NHC$_2$H$_4$NH-HA

Sodium hyaluronate (500 mg, molecular weight: about 2,300,000) was reacted with compound 1 (0.031 mmol) obtained in Example 1-1 by a method similar to Example 2-1 to provide an aqueous solution of the title HA-MTX conjugate. As determined by the same methods as in Example 2-1, the molecular weight thereof and the conjugation rate of MTX therein were about 2,190,000 and 2.2%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 2,060,000 and 2.3%, respectively.

$^1$H-NMR (500 MHz, D$_2$O): δ1.83 (m), 2.01 (br.s), 2.14 (m), 2.52 (m), 2.70 (m), 2.96 (m), 3.35 (br.s), 3.51 (br.s), 3.57 (br.s), 3.71 (br.s), 3.83 (br.s), 4.16 (t), 4.46 (br.s), 4.55 (br.s), 4.87 (d), 4.97 (d), 6.66 (d), 6.88-7.09 (m), 7.72 (d), 8.69 (s)

Example 2-3

Production of MTX-α-PhePhe-NHC$_2$H$_4$NH-HA

A solution consisting of 3-hydroxy-3,4-dihydro-4-oxo-1,2,3-benzotriazine (HOOBt) (0.125 mmol) and compound 1 (0.008 mmol) obtained in Example 1-1 dissolved in an equal quantity mixture (20 ml) of extrapure water and tetrahydrofuran (THF) was added to a suspension in which THF (10 ml) was added to sodium hyaluronate (500 mg, molecular weight: about 2,300,000), then a solution consisting of tris[2-(2-methoxyethoxy)ethyl]amine (0.118 mmol) dissolved in an equal quantity mixture (10 ml) of extrapure water and THF was added, followed by stirring at 5° C. A solution consisting of 1-ethyl-3-(3-dimethylaminopropyl)carbodiimide hydrochloride (EDC) (0.125 mmol) dissolved in extrapure water (10 ml) was added 30 minutes after the start of the stirring, followed by stirring at 5° C. for 20 hours. A 0.09N sodium hydroxide aqueous solution (220 ml) was added to the reaction solution, followed by stirring at 5° C. for 3.5 hours. To this solution was added 1N hydrochloric acid (20 ml) for neutralization, to which a solution consisting of sodium chloride (9 g) dissolved in extrapure water (45 ml) was further added, followed by dropwise adding ethanol (600 ml) for ethanol precipitation before separating the precipitate by centrifugation. The precipitate was dissolved in extrapure water (40 ml) to provide an aqueous solution of the title HA-MTX conjugate. The molecular weight thereof as determined by a gel filtration technique using hyaluronic acid as a standard substance was about 2,320,000. The conjugation rate of MTX in the resultant conjugate was 0.6% when calculated by measuring ultraviolet absorption (259 nm).

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 2,170,000 and 0.5%, respectively.

$^1$H-NMR (500 MHz, D$_2$O): δ2.01 (br.s), 2.52 (m), 2.69 (m), 2.95 (m), 3.34 (br.d), 3.51 (br.s), 3.57 (br.s), 3.71 (br.s), 3.83 (br.s), 4.16 (t), 4.46 (br.s), 4.55 (br.s), 6.66 (d), 6.87-7.10 (m), 7.72 (d), 8.69 (s)

Example 2-4

Production of MTX-α-PhePhe-NHC$_2$H$_4$NH-HA

A solution consisting of 3-hydroxy-3,4-dihydro-4-oxo-1,2,3-benzotriazine (HOOBt) (0.125 mmol) and compound 1 (0.015 mmol) obtained in Example 1-1 dissolved in an equal quantity mixture (20 ml) of extrapure water and tetrahydrofuran (THF) was added to a suspension in which THF (10 ml) was added to sodium hyaluronate (500 mg, molecular weight: about 2,300,000), to which a solution consisting of tris[2-(2-methoxyethoxy)ethyl]amine (0.110 mmol) dissolved in an equal quantity mixture (10 ml) of extrapure water and THF was then added, followed by stirring at 5° C. A solution consisting of 1-ethyl-3-(3-dimethylaminopropyl)carbodiimide hydrochloride (EDC) (0.125 mmol) dissolved in extrapure water (10 ml) was added 30 minutes after the start of the stirring, followed by stirring at 5° C. for 20 hours. A 0.09N sodium hydroxide aqueous solution (220 ml) was added to the reaction solution, followed by stirring at 5° C. for 3.5 hours. To this solution was added 1N hydrochloric acid (20 ml) for neutralization, to which a solution consisting of sodium chloride (9 g) dissolved in extrapure water (45 ml) was further added, followed by dropwise adding ethanol (600 ml) for ethanol precipitation before separating the precipitate by centrifugation. The precipitate was dissolved in extrapure water (40 ml) to provide an aqueous solution of the title HA-MTX conjugate. The molecular weight thereof as determined by a gel filtration technique using hyaluronic acid as a standard substance was about 2,320,000. The conjugation rate of MTX in the resultant conjugate was 1.1% when calculated by measuring ultraviolet absorption (259 nm).

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 2,230,000 and 1.1%, respectively.

$^1$H-NMR (500 MHz, D$_2$O): δ1.84 (m), 2.01 (br.s), 2.13 (m), 2.52 (m), 2.70 (m), 2.96 (m), 3.35 (br.s), 3.51 (br.s), 3.57 (br.s), 3.71 (br.s), 3.83 (br.s), 4.16 (t), 4.46 (br.s), 4.55 (br.s), 6.66 (d), 6.88-7.09 (m), 7.72 (d), 8.69 (s)

Example 2-5

Production of MTX-α-PhePhe-NHC$_2$H$_4$NH-HA

A solution consisting of 3-hydroxy-3,4-dihydro-4-oxo-1,2,3-benzotriazine (HOOBt) (0.125 mmol) and compound 1 (0.020 mmol) obtained in Example 1-1 dissolved in an equal quantity mixture (20 ml) of extrapure water and tetrahydrofuran (THF) was added to a suspension in which THF (10 ml) was added to sodium hyaluronate (500 mg, molecular weight: about 2,300,000), to which a solution consisting of tris[2-(2-methoxyethoxy)ethyl]amine (0.105 mmol) dissolved in an equal quantity mixture (10 ml) of extrapure water and THF was then added, followed by stirring at 5° C. A solution consisting of 1-ethyl-3-(3-dimethylaminopropyl)carbodiimide hydrochloride (EDC) (0.125 mmol) dissolved in extrapure water (10 ml) was added 30 minutes after the start of the stirring, followed by stirring at 5° C. for 20 hours. A 0.09N sodium hydroxide aqueous solution (220 ml) was added to the reaction solution, followed by stirring at 5° C. for 3.5 hours. To this solution was added 1N hydrochloric acid (20 ml) for neutralization, to which a solution consisting of sodium chloride (9 g) dissolved in extrapure water (45 ml) was further added, followed by dropwise adding ethanol (600 ml) for ethanol precipitation before separating the precipitate by centrifugation. The precipitate was dissolved in extrapure water (40 ml) to provide an aqueous solution of the title HA-MTX conjugate. The molecular weight thereof as determined by a gel filtration technique using hyaluronic acid as a standard substance was about 2,270,000. The conjugation rate of MTX in the resultant conjugate was 1.4% when calculated by measuring ultraviolet absorption (259 nm).

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 2,090,000 and 1.3%, respectively.

$^1$H-NMR (500 MHz, D$_2$O): δ1.84 (m), 2.01 (br.s), 2.13 (m), 2.49 (t), 2.68 (m), 2.95 (m), 3.36 (br.s), 3.51 (br.s), 3.56 (br.s), 3.71 (br.s), 3.83 (br.s), 4.16 (t), 4.46 (br.s), 4.55 (br.d), 4.88 (d), 4.98 (d), 6.63 (d), 6.87-7.13 (m), 7.74 (d), 8.70 (s)

Example 2-6

Production of MTX-α-PhePhe-NHC$_2$H$_4$NH-HA

A solution consisting of 3-hydroxy-3,4-dihydro-4-oxo-1,2,3-benzotriazine (HOOBt) (0.125 mmol) and compound 1 (0.063 mmol) obtained in Example 1-1 dissolved in an equal quantity mixture (20 ml) of extrapure water and tetrahydrofuran (THF) was added to a suspension in which THF (10 ml) was added to sodium hyaluronate (500 mg, molecular weight: about 2,300,000), to which a solution consisting of tris[2-(2-methoxyethoxy)ethyl]amine (0.063 mmol) dissolved in an equal quantity mixture (10 ml) of extrapure water and THF was then added, followed by stirring at 5° C. A solution consisting of 1-ethyl-3-(3-dimethylaminopropyl)carbodiimide hydrochloride (EDC) (0.125 mmol) dissolved in extrapure water (10 ml) was added 30 minutes after the start of the stirring, followed by stirring at 5° C. for 20 hours. A 0.09N sodium hydroxide aqueous solution (220 ml) was added to the reaction solution, followed by stirring at 5° C. for 3.5 hours. To this solution was added 1N hydrochloric acid (20 ml) for neutralization, to which a solution consisting of sodium chloride (9 g) dissolved in extrapure water (45 ml) was further added, followed by dropwise adding ethanol (600 ml) for ethanol precipitation before separating the precipitate by centrifugation. The precipitate was dissolved in extrapure water (40 ml) to provide an aqueous solution of the title HA-MTX conjugate. The molecular weight thereof as determined by a gel filtration technique using hyaluronic acid as a standard substance was about 2,050,000. The conjugation rate of MTX in the resultant conjugate was 3.9% when calculated by measuring ultraviolet absorption (259 nm).

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,910,000 and 3.8%, respectively.

$^1$H-NMR (500 MHz, D$_2$O): δ1.84 (m), 2.02 (br.s), 2.15 (m), 2.53 (t), 2.70 (m), 2.96 (m), 3.35 (br.s), 3.51 (br.s), 3.57 (br.s), 3.71 (br.s), 3.83 (br.s), 4.16 (t), 4.46 (br.s), 4.55 (br.s), 4.89 (s), 4.96 (d), 6.66 (d), 6.87-7.10 (m), 7.72 (d), 8.68 (s)

Example 2-7

Production of MTX-α-PhePhe-NHC$_2$H$_4$NH-HA

A solution consisting of 3-hydroxy-3,4-dihydro-4-oxo-1,2,3-benzotriazine (HOOBt) (0.125 mmol) and compound 1 (0.125 mmol) obtained in Example 1-1 dissolved in an equal quantity mixture (20 ml) of extrapure water and tetrahydrofuran (THF) was added to a suspension in which THF (10 ml) was added to sodium hyaluronate (500 mg, molecular weight: about 2,300,000), to which an equal quantity mixture (10 ml) of extrapure water and THF was then added, followed by stirring at 5° C. A solution consisting of 1-ethyl-3-(3-dimethylaminopropyl)carbodiimide hydrochloride (EDC) (0.125 mmol) dissolved in extrapure water (10 ml) was added 30 minutes after the start of the stirring, followed by stirring at 5° C. for 20 hours. A 0.09N sodium hydroxide aqueous solution (220 ml) was added to the reaction solution, followed by stirring at 5° C. for 3.5 hours. To this solution was added 1N hydrochloric acid (20 ml) for neutralization, to which a solution consisting of sodium chloride (9 g) dissolved in extrapure water (45 ml) was further added, followed by dropwise adding ethanol (600 ml) for ethanol precipitation before separating the precipitate by centrifugation. The precipitate was dissolved in extrapure water (40 ml) to provide an aqueous solution of the title HA-MTX conjugate. The molecular weight thereof as determined by a gel filtration technique using hyaluronic acid as a standard substance was about 1,970,000. The conjugation rate of MTX in the resultant conjugate was 4.5% when calculated by measuring ultraviolet absorption (259 nm).

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,740,000 and 4.4%, respectively.

$^1$H-NMR (500 MHz, D$_2$O): δ1.83 (m), 1.93 (m), 2.02 (br.s), 2.14 (m), 2.53 (t), 2.69 (m), 2.95 (m), 3.35 (br.s), 3.51 (br.s), 3.57 (br.s), 3.71 (br.s), 3.83 (br.s), 4.16 (t), 4.46 (br.s), 4.55 (br.d), 4.87 (d), 4.95 (d), 6.67 (d), 6.87-7.10 (m), 7.71 (d), 8.68 (s)

Example 2-8

Production of MTX-α-PhePhe-NHC$_{10}$H$_2$OO$_3$NH-HA

Sodium hyaluronate (500 mg, molecular weight: about 2,300,000) was reacted with compound 2 (0.031 mmol) obtained in Example 1-2 by a method similar to Example 2-1 to provide an aqueous solution of the title HA-MTX conjugate. As determined by the same methods as in Example 2-1,

Example 2-9

Production of MTX-α-PhePhe-NHC$_{10}$H$_{20}$O$_2$NH-HA

Sodium hyaluronate (500 mg, molecular weight: about 2,300,000) was reacted with compound 3 (0.031 mmol) obtained in Example 1-3 by a method similar to Example 2-1 to provide an aqueous solution of the title HA-MTX conjugate. As determined by the same methods as in Example 2-1, the molecular weight thereof and the conjugation rate of MTX therein were about 1,830,000 and 1.8%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,550,000 and 1.7%, respectively.

Example 2-10

Production of MTX-α-PhePhe-NHC$_8$H$_{16}$O$_2$NH-HA

Sodium hyaluronate (500 mg, molecular weight: about 2,300,000) was reacted with compound 4 (0.031 mmol) obtained in Example 1-4 by a method similar to Example 2-1 to provide an aqueous solution of the title HA-MTX conjugate. As determined by the same methods as in Example 2-1, the molecular weight thereof and the conjugation rate of MTX therein were about 1,890,000 and 1.6%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,620,000 and 1.6%, respectively.

Example 2-11

Production of MTX-α-PhePhe-NHC$_6$H$_{12}$O$_2$NH-HA

Sodium hyaluronate (500 mg, molecular weight: about 2,300,000) was reacted with compound 5 (0.031 mmol) obtained in Example 1-5 by a method similar to Example 2-1 to provide an aqueous solution of the title HA-MTX conjugate. As determined by the same methods as in Example 2-1, the molecular weight thereof and the conjugation rate of MTX therein were about 1,920,000 and 1.9%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,620,000 and 2.0%, respectively.

$^1$H-NMR (500 MHz, D$_2$O): δ1.77-1.85 (m), 2.02 (br.s), 2.16-2.24 (m), 2.51 (m), 2.66 (m), 2.92 (m), 3.00 (m), 3.35 (br.s), 3.51 (br.s), 3.57 (br.s), 3.72 (br.s), 3.83 (br.s), 4.20 (m), 4.46 (br.s), 4.55 (br.s), 6.68 (d), 6.95-7.18 (m), 7.76 (d), 8.72 (s)

Example 2-12

Production of MTX-α-PhePhe-NHC$_4$H$_{80}$NH-HA

Sodium hyaluronate (500 mg, molecular weight: about 2,300,000) was reacted with compound 6 (0.031 mmol) obtained in Example 1-6 by a method similar to Example 2-1 to provide an aqueous solution of the title HA-MTX conjugate. As determined by the same methods as in Example 2-1, the molecular weight thereof and the conjugation rate of MTX therein were about 1,720,000 and 2.0%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,490,000 and 1.9%, respectively.

$^1$H-NMR (500 MHz, D$_2$O): δ1.77-1.84 (m), 2.01 (br.s), 2.20-2.28 (m), 2.49 (m), 2.64 (m), 2.93 (m), 3.00 (m), 3.35 (br.s), 3.52 (br.s), 3.58 (br.s), 3.73 (br.s), 3.83 (br.s), 4.20 (t), 4.47 (br.s), 4.55 (br.s), 4.92 (d), 5.06 (d), 6.64 (d), 6.94-7.19 (m), 7.77 (d), 8.73 (s)

Example 2-13

Production of MTX-α-PhePhe-NHC$_5$H$_{10}$NH-HA

Sodium hyaluronate (500 mg, molecular weight: about 2,300,000) was reacted with compound 7 (0.031 mmol) obtained in Example 1-7 by a method similar to Example 2-1 to provide an aqueous solution of the title HA-MTX conjugate. As determined by the same methods as in Example 2-1, the molecular weight thereof and the conjugation rate of MTX therein were about 2,140,000 and 1.4%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,960,000 and 1.2%, respectively.

Example 2-14

Production of MTX-α-PhePhe-Lys-HA

Sodium hyaluronate (500 mg, molecular weight: about 2,300,000) was reacted with compound 8 (0.031 mmol) obtained in Example 1-8 by a method similar to Example 2-1 to provide an aqueous solution of the title HA-MTX conjugate. As determined by the same methods as in Example 2-1, the molecular weight thereof and the conjugation rate of MTX therein were about 1,890,000 and 1.4%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,720,000 and 1.4%, respectively.

Example 2-15

Production of MTX-α-PheGly-NHC$_{10}$H$_{20}$O$_3$NH-HA

Sodium hyaluronate (500 mg, molecular weight: about 800,000) was reacted with compound 2 (0.031 mmol) obtained in Example 1-2 by a method similar to Example 2-1 to provide an aqueous solution of the title HA-MTX conjugate. As determined by the same methods as in Example 2-1, the molecular weight thereof and the conjugation rate of MTX therein were about 830,000 and 1.4%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 800,000 and 1.4%, respectively.

Example 2-16

Production of MTX-α-PheGly-NHC$_{10}$H$_{20}$O$_3$NH-HA

A solution consisting of 3-hydroxy-3,4-dihydro-4-oxo-1,2,3-benzotriazine (HOOBt) (0.125 mmol) and compound 2 (0.009 mmol) obtained in Example 1-2 dissolved in an equal quantity mixture (20 ml) of extrapure water and tetrahydrofuran (THF) was added to a suspension in which THF (10 ml) was added to sodium hyaluronate (500 mg, molecular weight: about 800,000), to which a solution consisting of tris[2-(2-methoxyethoxy)ethyl]amine (0.116 mmol) dissolved in an equal quantity mixture (10 ml) of extrapure water and THF was then added, followed by stirring at 5° C. A solution consisting of 1-ethyl-3-(3-dimethylaminopropyl)carbodiimide hydrochloride (EDC) (0.125 mmol) dissolved in extrapure water (10 ml) was added 30 minutes after the start of the stirring, followed by stirring at 5° C. for 20 hours. A 0.09N sodium hydroxide aqueous solution (220 ml) was added to the reaction solution, followed by stirring at 5° C. for 3.5 hours. To this solution was added 1N hydrochloric acid (20 ml) for neutralization, to which a solution consisting of sodium chloride (9 g) dissolved in extrapure water (45 ml) was further added, followed by dropwise adding ethanol (600 ml) for ethanol precipitation before separating the precipitate by centrifugation. The precipitate was dissolved in Otsuka physiological saline (40 ml) to provide an aqueous solution of the title HA-MTX conjugate. The molecular weight thereof as determined by a gel filtration technique using hyaluronic acid as a standard substance was about 830,000. The conjugation rate of MTX in the resultant conjugate was 0.5% when calculated by measuring ultraviolet absorption (259 nm).

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 810,000 and 0.5%, respectively.

Example 2-17

Production of MTX-α-PheGly-NHC$_{10}$H$_{20}$O$_3$NH-HA

A solution consisting of 3-hydroxy-3,4-dihydro-4-oxo-1,2,3-benzotriazine (HOOBt) (0.125 mmol) and compound 2 (0.125 mmol) obtained in Example 1-2 dissolved in an equal quantity mixture (20 ml) of extrapure water and tetrahydrofuran (THF) was added to a suspension in which THF (10 ml) was added to sodium hyaluronate (500 mg, molecular weight: about 800,000), to which an equal quantity mixture (10 ml) of extrapure water and THF was then added, followed by stirring at 5° C. A solution consisting of 1-ethyl-3-(3-dimethylaminopropyl)carbodiimide hydrochloride (EDC) (0.125 mmol) dissolved in extrapure water (10 ml) was added 30 minutes after the start of the stirring, followed by stirring at 5° C. for 20 hours. A 0.09N sodium hydroxide aqueous solution (220 ml) was added to the reaction solution, followed by stirring at 5° C. for 3.5 hours. To this solution was added 1N hydrochloric acid (20 ml) for neutralization, to which a solution consisting of sodium chloride (9 g) dissolved in extrapure water (45 ml) was further added, followed by dropwise adding ethanol (600 ml) for ethanol precipitation before separating the precipitate by centrifugation. The precipitate was dissolved in extrapure water (40 ml) to provide an aqueous solution of the title HA-MTX conjugate. The molecular weight thereof as determined by a gel filtration technique using hyaluronic acid as a standard substance was about 770,000. The conjugation rate of MTX in the resultant conjugate was 3.4% when calculated by measuring ultraviolet absorption (259 nm).

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 760,000 and 3.4%, respectively.

Example 2-18

Production of MTX-α-PheGly-NHC$_{10}$H$_{20}$O$_3$NH-HA

Sodium hyaluronate (500 mg, molecular weight: about 2,300,000) was reacted with compound 9 (0.031 mmol) obtained in Example 1-9 by a method similar to Example 2-1 to provide an aqueous solution of the title HA-MTX conjugate. As determined by the same methods as in Example 2-1, the molecular weight thereof and the conjugation rate of MTX therein were about 1,990,000 and 1.5%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,860,000 and 1.4%, respectively.

$^1$H-NMR (500 MHz, D$_2$O): δ1.59 (m), 1.78 (m), 1.90-1.95 (m), 2.02 (br.s), 2.13-2.23 (m), 2.99-3.14 (m), 3.28 (s), 3.35 (br.s), 3.51 (br.s), 3.57 (br.s), 3.71 (br.s), 3.83 (br.s), 4.26 (t), 4.46 (br.s), 4.54 (br.s), 4.92 (s), 6.93 (d), 7.13-7.20 (m), 7.66 (d), 8.69 (s)

Example 2-19

Production of MTX-α-PheGly-NHC$_{10}$H$_{20}$O$_2$NH-HA

Sodium hyaluronate (500 mg, molecular weight: about 2,300,000) was reacted with compound 10 (0.031 mmol) obtained in Example 1-10 by a method similar to Example 2-1 to provide an aqueous solution of the title HA-MTX conjugate.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,440,000 and 1.8%, respectively.

$^1$H-NMR (500 MHz, D$_2$O): δ1.49 (m), 1.60 (m), 1.76 (m), 2.01 (br.s), 2.09-2.15 (m), 2.20-2.28 (m), 2.99-3.09 (m), 3.10-3.17 (m), 3.33 (br.s), 3.51 (br.s), 3.57 (br.s), 3.71 (br.s), 3.83 (br.s), 4.30 (m), 4.46 (br.s), 4.55 (br.d), 4.97 (s), 6.91 (d), 7.13 (m), 7.17-7.21 (m), 7.67 (d), 8.73 (s)

Example 2-20

Production of MTX-α-PheGly-NHC$_8$H$_{16}$O$_2$NH-HA

Sodium hyaluronate (500 mg, molecular weight: about 2,300,000) was reacted with compound 11 (0.031 mmol) obtained in Example 1-11 by a method similar to Example 2-1 to provide an aqueous solution of the title HA-MTX conjugate. As determined by the same methods as in Example 2-1, the molecular weight thereof and the conjugation rate of MTX therein were about 1,730,000 and 1.6%, respectively.

Example 2-21

Production of MTX-α-PheGly-NHC$_6$H$_{12}$O$_2$NH-HA

Sodium hyaluronate (500 mg, molecular weight: about 2,300,000) was reacted with compound 12 (0.031 mmol) obtained in Example 1-12 by a method similar to Example 2-1 to provide an aqueous solution of the title HA-MTX conjugate. As determined by the same methods as in Example 2-1, the molecular weight thereof and the conjugation rate of MTX therein were about 1,500,000 and 2.3%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,390,000 and 2.3%, respectively.

$^1$H-NMR (500 MHz, D$_2$O): δ1.64 (m), 1.78 (m), 2.01 (br.s), 2.09-2.17 (m), 2.24 (m), 3.01 (m), 3.08 (m), 3.16 (m), 3.34 (br.s), 3.51 (br.s), 3.56 (br.s), 3.71 (br.s), 3.83 (br.s), 4.31 (m), 4.46 (br.s), 4.54 (br.s), 4.97 (s), 6.91 (d), 7.11 (m), 7.14-7.21 (m), 7.67 (d), 8.72 (s)

Example 2-21

Production of MTX-α-PheGly-NHC$_6$H$_{12}$O$_2$NH-HA

Sodium hyaluronate (500 mg, molecular weight: about 2,300,000) was reacted with compound 12 (0.031 mmol) obtained in Example 1-12 by a method similar to Example 2-1 to provide an aqueous solution of the title HA-MTX conjugate. As determined by the same methods as in Example 2-1, the molecular weight thereof and the conjugation rate of MTX therein were about 1,500,000 and 2.3%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,390,000 and 2.3%, respectively.

Example 2-22

Production of MTX-α-PheGly-NHC$_4$H$_8$ONH-HA

Sodium hyaluronate (500 mg, molecular weight: about 2,300,000) was reacted with compound 13 (0.031 mmol) obtained in Example 1-13 by a method similar to Example 2-1 to provide an aqueous solution of the title HA-MTX conjugate. As determined by the same methods as in Example 2-1, the molecular weight thereof and the conjugation rate of MTX therein were about 1,560,000 and 2.0%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,400,000 and 2.2%, respectively.

Example 2-23

Production of MTX-α-PhePro-NHC$_{10}$H$_{20}$O$_3$NH-HA

Sodium hyaluronate (500 mg, molecular weight: about 2,300,000) was reacted with compound 14 (0.031 mmol) obtained in Example 1-14 by a method similar to Example 2-1 to provide an aqueous solution of the title HA-MTX conjugate. As determined by the same methods as in Example 2-1, the molecular weight thereof and the conjugation rate of MTX therein were about 1,660,000 and 1.6%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,520,000 and 1.6%, respectively.

Example 2-24

Production of MTX-α-PheβAla-NHC$_{10}$H$_{20}$O$_3$NH-HA

Sodium hyaluronate (500 mg, molecular weight: about 2,300,000) was reacted with compound 15 (0.031 mmol) obtained in Example 1-15 by a method similar to Example 2-1 to provide an aqueous solution of the title HA-MTX conjugate.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,520,000 and 1.5%, respectively.

Example 2-25

Production of MTX-α-PheβAla-NHC$_2$H$_4$NH-HA

Sodium hyaluronate (500 mg, molecular weight: about 2,300,000) was reacted with compound 16 (0.031 mmol) obtained in Example 1-16 by a method similar to Example 2-1 to provide an aqueous solution of the title HA-MTX conjugate. As determined by the same methods as in Example 2-1, the molecular weight thereof and the conjugation rate of MTX therein were about 2,090,000 and 2.3%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,980,000 and 2.3%, respectively.

Example 2-26

Production of MTX-α-Phe-NHC$_{10}$H$_{20}$O$_3$NH-HA

Sodium hyaluronate (500 mg, molecular weight: about 2,300,000) was reacted with compound 17 (0.031 mmol) obtained in Example 1-17 by a method similar to Example 2-1 to provide an aqueous solution of the title HA-MTX conjugate. As determined by the same methods as in Example 2-1, the molecular weight thereof and the conjugation rate of MTX therein were about 2,130,000 and 1.7%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,790,000 and 1.7%, respectively.

$^1$H-NMR (500 MHz, D$_2$O): δ1.63 (m), 1.79 (m), 2.02 (br.s), 2.20 (m), 2.28 (m), 3.08 (m), 3.10-3.20 (m), 3.31 (s), 3.35 (br.s), 3.52 (br.s), 3.56 (br.s), 3.72 (br.s), 3.84 (br.s), 4.28 (t), 4.47 (br.s), 4.54 (br.s), 4.97 (s), 6.94 (d), 7.06 (t), 7.13 (d), 7.67 (d), 8.73 (s)

Example 2-27

Production of MTX-α-Ile-NHC$_{10}$H$_{20}$O$_3$NH-HA

Sodium hyaluronate (500 mg, molecular weight: about 2,300,000) was reacted with compound 18 (0.031 mmol) obtained in Example 1-18 by a method similar to Example 2-1 to provide an aqueous solution of the title HA-MTX conjugate. As determined by the same methods as in Example 2-1, the molecular weight thereof and the conjugation rate of MTX therein were about 1,920,000 and 1.7%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,620,000 and 1.7%, respectively.

¹H-NMR (500 MHz, D₂O): δ0.84 (t), 0.89 (d), 1.18 (m), 1.47 (m), 1.78 (m), 1.83-1.90 (m), 2.02 (br.s), 2.36 (m), 3.24 (s), 3.35 (br.s), 3.51 (br.s), 3.57 (br.s), 3.63 (br.s), 3.71 (br.s), 3.83 (br.s), 4.09 (d), 4.45 (br.s), 4.55 (br.s), 4.93 (s), 6.92 (d), 7.72 (d), 8.68 (s)

Example 2-28

Production of MTX-α-Ile-NHC₂H₄NH-HA

Sodium hyaluronate (500 mg, molecular weight: about 2,300,000) was reacted with compound 19 (0.031 mmol) obtained in Example 1-19 by a method similar to Example 2-1 to provide an aqueous solution of the title HA-MTX conjugate. As determined by the same methods as in Example 2-1, the molecular weight thereof and the conjugation rate of MTX therein were about 2,310,000 and 2.1%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 2,020,000 and 2.1%, respectively.

Example 2-29

Production of MTX-α-Glu-NHC₁₀H₂₀O₃NH-HA

Sodium hyaluronate (500 mg, molecular weight: about 2,300,000) was reacted with compound 20 (0.031 mmol) obtained in Example 1-20 by a method similar to Example 2-1 to provide an aqueous solution of the title HA-MTX conjugate. As determined by the same methods as in Example 2-1, the molecular weight thereof and the conjugation rate of MTX therein were about 2,010,000 and 1.5%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,830,000 and 1.5%, respectively.

¹H-NMR (500 MHz, D₂O): δ1.57 (m), 1.77 (m), 2.02 (br.s), 2.25 (m), 2.37 (t), 3.24 (s), 3.25 (s), 3.35 (br.s), 3.51 (br.s), 3.56 (br.s), 3.71 (br.s), 3.83 (br.s), 4.13 (m), 4.22 (m), 4.36 (m), 4.46 (br.s), 4.55 (br.s), 4.91 (s), 6.94 (d), 7.76 (d), 8.66 (s), 8.68 (s)

Note: The underlined portions are minor signals. From the signals, it was deduced to be a mixture of α- and γ-isomers.

Example 2-30

Production of MTX-α-Glu-NHC₂H₄NH-HA

Sodium hyaluronate (500 mg, molecular weight: about 2,300,000) was reacted with compound 21 (0.031 mmol) obtained in Example 1-21 by a method similar to Example 2-1 to provide an aqueous solution of the title HA-MTX conjugate. As determined by the same methods as in Example 2-1, the molecular weight thereof and the conjugation rate of MTX therein were about 2,260,000 and 2.1%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 2,060,000 and 2.1%, respectively.

Example 2-31

Production of MTX-α-Tyr-NHC₁₀H₂₀O₃NH-HA

Sodium hyaluronate (500 mg, molecular weight: about 2,300,000) was reacted with compound 22 (0.031 mmol) obtained in Example 1-22 by a method similar to Example 2-1 to provide an aqueous solution of the title HA-MTX conjugate. As determined by the same methods as in Example 2-1, the molecular weight thereof and the conjugation rate of MTX therein were about 1,900,000 and 1.6%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,760,000 and 1.7%, respectively.

¹H-NMR (500 MHz, D₂O): δ1.63 (m), 1.77 (m), 2.02 (br.s), 2.23-2.35 (m), 2.95 (m), 3.03-3.21 (m), 3.34 (br.s), 3.51 (br.s), 3.58 (br.s), 3.71 (br.s), 3.83 (br.s), 4.28 (m), 4.47 (br.d), 4.54 (br.s), 4.92 (s), 6.58 (d), 6.94 (d), 7.66 (d), 8.68 (s)

Example 2-32

Production of MTX-α-Trp-NHC₁₀H₂₀O₃NH-HA

Sodium hyaluronate (500 mg, molecular weight: about 2,300,000) was reacted with compound 23 (0.031 mmol) obtained in Example 1-23 by a method similar to Example 2-1 to provide an aqueous solution of the title HA-MTX conjugate. As determined by the same methods as in Example 2-1, the molecular weight thereof and the conjugation rate of MTX therein were about 1,870,000 and 1.9%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,390,000 and 1.9%, respectively.

¹H-NMR (500 MHz, D₂O): δ1.53 (m), 1.74 (m), 2.01 (br.s), 2.09-2.15 (m), 2.46 (m), 2.85 (m), 3.05 (m), 3.35 (br.s), 3.52 (br.s), 3.58 (br.s), 3.74 (br.s), 3.83 (br.s), 4.27 (m), 4.48 (br.d), 4.55 (br.s), 6.83 (d), 6.99 (s), 7.05 (s), 7.15 (d), 7.43 (d), 7.49 (s), 8.74 (s)

Example 2-33

Production of MTX-α-Ser-NHC₁₀H₂₀O₃NH-HA

Sodium hyaluronate (500 mg, molecular weight: about 2,300,000) was reacted with compound 24 (0.031 mmol) obtained in Example 1-24 by a method similar to Example 2-1 to provide an aqueous solution of the title HA-MTX conjugate. As determined by the same methods as in Example 2-1, the molecular weight thereof and the conjugation rate of MTX therein were about 1,860,000 and 1.7%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,650,000 and 1.7%, respectively.

¹H-NMR (500 MHz, D₂O): δ1.61 (m), 1.76 (m), 2.02 (br.s), 2.38 (t), 2.51 (m), 3.24 (s), 3.25 (s), 3.35 (br.s), 3.50 (br.s), 3.56 (br.s), 3.58 (br.s), 3.71 (br.s), 3.83 (br.s), 4.28 (m), 4.39 (m), 4.46 (br.s), 4.54 (br.s), 4.91 (s), 6.93 (d), 7.70 (d), 7.76 (d), 8.66 (s), 8.68 (s)

Note: The underlined portions are minor signals. From the signals, it was deduced to be a mixture of α- and γ-isomers.

Example 2-34

Production of MTX-α-Leu-NHC$_{10}$H$_{20}$O$_3$NH-HA

Sodium hyaluronate (500 mg, molecular weight: about 2,300,000) was reacted with compound 25 (0.031 mmol) obtained in Example 1-25 by a method similar to Example 2-1 to provide an aqueous solution of the title HA-MTX conjugate. As determined by the same methods as in Example 2-1, the molecular weight thereof and the conjugation rate of MTX therein were about 1,890,000 and 1.7%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,470,000 and 1.6%, respectively.

$^1$H-NMR (500 MHz, D$_2$O): δ0.84 (d), 0.89 (d), 1.52-1.68 (m), 1.72-1.83 (m), 2.01 (br.s), 2.45 (t), 3.34 (br.s), 3.50 (br.s), 3.57 (br.s), 3.72 (br.s), 3.83 (br.s), 4.28 (m), 4.45 (br.d), 4.54 (br.s), 4.95 (s), 6.91 (d), 7.72 (d), 8.69 (s)

Example 2-35

Production of MTX-α-Val-NHC$_{10}$H$_{20}$O$_3$NH-HA

Sodium hyaluronate (500 mg, molecular weight: about 2,300,000) was reacted with compound 26 (0.031 mmol) obtained in Example 1-26 by a method similar to Example 2-1 to provide an aqueous solution of the title HA-MTX conjugate. As determined by the same methods as in Example 2-1, the molecular weight thereof and the conjugation rate of MTX therein were about 1,870,000 and 1.7%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,560,000 and 1.7%, respectively.

$^1$H-NMR (500 MHz, D$_2$O): δ0.93 (m), 1.78 (m), 2.01 (br.s), 2.11-2.19 (m), 2.47 (m), 3.24 (s), 3.34 (br.s), 3.51 (br.s), 3.57 (br.s), 3.63 (br.s), 3.72 (br.s), 3.83 (br.s), 4.02 (d), 4.47 (br.d), 4.54 (br.s), 4.95 (s), 6.91 (d), 7.72 (d), 8.69 (s)

Example 2-36

Production of MTX-α-His-NHC$_{10}$H$_{20}$O$_3$NH-HA

Sodium hyaluronate (500 mg, molecular weight: about 2,300,000) was reacted with compound 27 (0.031 mmol) obtained in Example 1-27 by a method similar to Example 2-1 to provide an aqueous solution of the title HA-MTX conjugate. As determined by the same methods as in Example 2-1, the molecular weight thereof and the conjugation rate of MTX therein were about 1,910,000 and 1.2%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,620,000 and 1.2%, respectively.

$^1$H-NMR (500 MHz, D$_2$O): δ1.70 (m), 1.79 (m), 2.01 (br.s), 2.23-2.36 (m), 3.13-3.22 (m), 3.26 (s), 3.34 (br.s), 3.50 (br.s), 3.56 (br.s), 3.61 (br.s), 3.71 (br.s), 3.83 (br.s), 4.33 (t), 4.46 (br.d), 4.54 (br.s), 4.96 (s), 6.92 (d), 7.30 (s), 7.73 (d), 8.57 (s), 8.70 (s)

Example 2-37

Production of MTX-α-Pro-NHC$_{10}$H$_{20}$O$_3$NH-HA

Sodium hyaluronate (500 mg, molecular weight: about 2,300,000) was reacted with compound 28 (0.031 mmol) obtained in Example 1-28 by a method similar to Example 2-1 to provide an aqueous solution of the title HA-MTX conjugate. As determined by the same methods as in Example 2-1, the molecular weight thereof and the conjugation rate of MTX therein were about 1,670,000 and 1.5%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,520,000 and 1.6%, respectively.

Example 2-38

Production of MTX-α-βAla-NHC$_{10}$H$_{20}$O$_3$NH-HA

Sodium hyaluronate (500 mg, molecular weight: about 2,300,000) was reacted with compound 29 (0.031 mmol) obtained in Example 1-29 by a method similar to Example 2-1 to provide an aqueous solution of the title HA-MTX conjugate. As determined by the same methods as in Example 2-1, the molecular weight thereof and the conjugation rate of MTX therein were about 1,910,000 and 1.7%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,430,000 and 1.7%, respectively.

$^1$H-NMR (500 MHz, D$_2$O): δ1.60 (m), 1.67 (m), 1.79 (m), 2.01 (br.s), 2.42 (m), 2.47 (m), 3.09 (t), 3.14 (t), 3.34 (br.s), 3.51 (br.s), 3.57 (br.s), 3.73 (br.s), 3.82 (br.s), 4.47 (br.s), 4.54 (br.d), 4.96 (s), 6.92 (d), 7.73 (d), 8.70 (s)

Example 2-39

Production of MTX-γ-PhePhe-NHC$_{10}$H$_{20}$O$_3$NH-HA

Sodium hyaluronate (500 mg, molecular weight: about 2,300,000) was reacted with compound 30 (0.031 mmol) obtained in Example 1-30 by a method similar to Example 2-1 to provide an aqueous solution of the title HA-MTX conjugate. As determined by the same methods as in Example 2-1, the molecular weight thereof and the conjugation rate of MTX therein were about 2,090,000 and 1.5%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,880,000 and 1.5%, respectively.

$^1$H-NMR (500 MHz, D$_2$O): δ1.52 (m), 1.81 (m), 2.02 (br.s), 2.16-2.29 (m), 2.60 (m), 2.76 (m), 2.99 (m), 3.07 (m), 3.18-3.26 (m), 3.32 (s), 3.35 (br.s), 3.52 (br.s), 3.56 (br.s), 3.66 (br.s), 3.73 (br.s), 3.84 (br.s), 4.15 (t), 4.27 (t), 4.36 (m), 4.47 (br.s), 4.55 (br.d), 6.86 (d), 6.92-6.99 (m), 7.02-7.16 (m), 7.79 (d), 8.71 (s)

Example 2-40

Production of MTX-γ-PhePhe-NHC$_6$H$_{12}$O$_2$NH-HA

Sodium hyaluronate (500 mg, molecular weight: about 2,300,000) was reacted with compound 31 (0.031 mmol) obtained in Example 1-31 by a method similar to Example 2-1 to provide an aqueous solution of the title HA-MTX conjugate. As determined by the same methods as in Example 2-1, the molecular weight thereof and the conjugation rate of MTX therein were about 1,890,000 and 2.0%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,760,000 and 2.0%, respectively.

$^1$H-NMR (500 MHz, D$_2$O): δ2.02 (br.s), 2.15-2.24 (m), 2.60 (m), 2.74-2.83 (m), 3.12-3.19 (m), 3.20-3.23 (m), 3.29 (s), 3.35 (br.s), 3.51 (br.s), 3.57 (br.s), 3.71 (br.s), 3.83 (br.s), 4.21 (t), 4.26 (t), 4.32 (m), 4.46 (br.s), 4.55 (br.d), 6.84 (s), 6.93 (d), 7.00-7.13 (m), 7.76 (d), 8.64 (s)

Example 2-41

Production of MTX-γ-PhePhe-NHC$_4$H$_8$ONH-HA

Sodium hyaluronate (500 mg, molecular weight: about 2,300,000) was reacted with compound 32 (0.031 mmol) obtained in Example 1-32 by a method similar to Example 2-1 to provide an aqueous solution of the title HA-MTX conjugate. As determined by the same methods as in Example 2-1, the molecular weight thereof and the conjugation rate of MTX therein were about 1,960,000 and 2.1%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,800,000 and 2.1%, respectively.

Example 2-42

Production of MTX-γ-PheGly-NHC$_{10}$H$_{20}$O$_3$NH-HA

Sodium hyaluronate (500 mg, molecular weight: about 2,300,000) was reacted with compound 33 (0.031 mmol) obtained in Example 1-33 by a method similar to Example 2-1 to provide an aqueous solution of the title HA-MTX conjugate. As determined by the same methods as in Example 2-1, the molecular weight thereof and the conjugation rate of MTX therein were about 1,900,000 and 1.4%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,720,000 and 1.5%, respectively.

$^1$H-NMR (500 MHz, D$_2$O): δ1.69 (m), 1.79 (m), 2.02 (br.s), 2.19-2.26 (m), 2.29 (m), 2.66 (m), 2.82 (m), 3.13 (m), 3.20 (m), 3.29 (s), 3.34 (br.s), 3.51 (br.s), 3.56 (br.s), 3.71 (br.s), 3.83 (br.s) 4.16 (t), 4.33 (m), 4.46 (br.s), 4.54 (br.s), 4.94 (d), 6.82 (s), 6.99-7.08 (m), 7.75 (d), 8.68 (s)

Example 2-43

Production of MTX-γ-Phe-NHC$_{10}$H$_{20}$O$_3$NH-HA

Sodium hyaluronate (500 mg, molecular weight: about 2,300,000) was reacted with compound 34 (0.031 mmol) obtained in Example 1-34 by a method similar to Example 2-1 to provide an aqueous solution of the title HA-MTX conjugate. As determined by the same methods as in Example 2-1, the molecular weight thereof and the conjugation rate of MTX therein were about 1,870,000 and 1.7%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,650,000 and 1.7%, respectively.

$^1$H-NMR (500 MHz, D$_2$O): δ1.44 (m), 1.80 (m), 2.02 (br.s), 2.31 (m), 2.53 (m), 2.68 (m), 2.88 (m), 3.01 (m), 3.13 (m), 3.18 (m), 3.31 (s), 3.35 (br.s), 3.51 (br.s), 3.58 (br.s), 3.63 (br.s), 3.72 (br.s), 3.84 (br.s), 4.02 (t), 4.37 (m), 4.47 (br.s), 4.55 (br.s), 4.86 (d), 4.98 (d), 6.76 (d), 7.02-7.09 (m), 7.78 (d), 8.72 (s)

Example 2-44

Production of MTX-γ-Glu-NHC$_{10}$H$_{20}$O$_3$NH-HA

Sodium hyaluronate (500 mg, molecular weight: about 2,300,000) was reacted with compound 35 (0.031 mmol) obtained in Example 1-35 by a method similar to Example 2-1 to provide an aqueous solution of the title HA-MTX conjugate. As determined by the same methods as in Example 2-1, the molecular weight thereof and the conjugation rate of MTX therein were about 1,790,000 and 1.6%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,490,000 and 1.7%, respectively.

$^1$H-NMR (500 MHz, D$_2$O): δ1.61-1.71 (m), 1.73-1.88 (m), 2.01 (br.s), 2.23 (m), 2.32 (t), 2.38-2.55 (m), 3.07 (m), 3.34 (br.s), 3.51 (br.s), 3.56 (br.s), 3.73 (br.s), 3.83 (br.s) 4.15 (m), 4.46 (br.s), 4.55 (br.s), 4.95 (s), 6.91 (d), 7.70 (d), 8.71 (s)

Example 2-45

Production of MTX-α-D-Phe-D-Phe-NHC$_{10}$H$_{20}$O$_3$NH-HA

Sodium hyaluronate (500 mg, molecular weight: about 2,300,000) was reacted with compound 36 (0.031 mmol) obtained in Example 1-36 by a method similar to Example 2-1 to provide an aqueous solution of the title HA-MTX conjugate. As determined by the same methods as in Example 2-1, the molecular weight thereof and the conjugation rate of MTX therein were about 1,480,000 and 1.4%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,350,000 and 1.4%, respectively.

Example 2-46

Production of MTX-γ-D-Phe-D-Phe-NHC$_{10}$H$_{20}$O$_3$NH-HA

Sodium hyaluronate (500 mg, molecular weight: about 2,300,000) was reacted with compound 37 (0.031 mmol) obtained in Example 1-37 by a method similar to Example 2-1 to provide an aqueous solution of the title HA-MTX conjugate. As determined by the same methods as in Example 2-1, the molecular weight thereof and the conjugation rate of MTX therein were about 1,600,000 and 1.4%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,410,000 and 1.3%, respectively.

Example 2-47

Production of MTX-α-AsnPhePhe-NHC$_{10}$H$_{20}$O$_3$NH-HA

Sodium hyaluronate (500 mg, molecular weight: about 2,300,000) was reacted with compound 38 (0.031 mmol) obtained in Example 1-38 by a method similar to Example 2-1 to provide an aqueous solution of the title HA-MTX conjugate. As determined by the same methods as in Example 2-1, the molecular weight thereof and the conjugation rate of MTX therein were about 2,100,000 and 1.3%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,780,000 and 1.2%, respectively.

$^1$H-NMR (500 MHz, D$_2$O): δ1.60 (m), 1.80 (m), 2.02 (br.s), 2.34 (m), 2.54 (m), 2.60-3.05 (m), 3.35 (br.s), 3.52 (br.s), 3.57 (br.s), 3.64 (br.s), 3.72 (br.s), 3.83 (br.s), 4.28 (m), 4.46 (br.s), 4.55 (br.s), 6.61 (d), 6.77 (t), 6.82-7.36 (m), 7.76 (d), 7.80 (d), 8.61 (s), 8.64 (s)

Note: The underlined portions are minor signals. From the signals, it was deduced to be a mixture of α- and γ-isomers.

Example 2-48

Production of MTX-α/γ-GlyPheLeuGly-NHC$_{10}$H$_{20}$O$_3$NH-HA

Sodium hyaluronate (500 mg, molecular weight: about 2,300,000) was reacted with compound 39 (0.031 mmol) obtained in Example 1-39 by a method similar to Example 2-1 to provide an aqueous solution of the title HA-MTX conjugate. As determined by the same methods as in Example 2-1, the molecular weight thereof and the conjugation rate of MTX therein were about 2,060,000 and 1.4%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 1,850,000 and 1.3%, respectively.

$^1$H-NMR (500 MHz, D$_2$O): δ0.72 (d), 0.77 (d), 0.81 (d), 1.32 (m), 1.50 (m), 1.67-1.82 (m), 2.01 (br.s), 2.23 (m), 2.33 (m), 2.75-3.03 (m), 3.51 (br.s), 3.58 (br.s), 3.71 (br.s), 3.83 (br.s), 4.16-4.28 (m), 4.46 (br.s), 4.54 (br.s), 6.85 (d), 6.92-7.06 (m), 7.75 (d), 7.78 (d), 8.63 (s), 8.65 (s)

Note: The underlined portions are minor signals. From the signals, it was deduced to be a mixture of α- and γ-isomers.

Example 2-49

Production of MTX-α-PhePhe-NHC$_{10}$H$_{20}$O$_3$NH-HA

Sodium hyaluronate (500 mg, molecular weight: about 320,000) was reacted with compound 2 (0.031 mmol) obtained in Example 1-2 by a method similar to Example 2-1 to provide an aqueous solution of the title HA-MTX conjugate.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 330,000 and 1.1%, respectively.

$^1$H-NMR (500 MHz, D$_2$O): δ1.67 (m), 1.79 (m), 1.84-1.94 (m), 2.02 (br.s), 2.12-2.20 (m), 2.59 (m), 2.77 (m), 2.91 (m), 2.99 (m), 3.12-3.25 (m), 3.35 (br.s), 3.49 (br.s), 3.51 (br.s), 3.57 (br.s), 3.71 (br.s), 3.83 (br.s) 4.18 (t), 4.45 (br.d), 4.55 (br.d), 4.88 (d), 4.96 (d), 6.76 (d), 6.95-7.10 (m), 7.72 (d), 8.68 (s)

Example 2-50

Production of MTX-α-PhePhe-NHC$_2$H$_4$NH-HA

Sodium hyaluronate (500 mg, molecular weight: about 340,000) was reacted with compound 1 (0.031 mmol) obtained in Example 1-1 by a method similar to Example 2-1 to provide an aqueous solution of the title HA-MTX conjugate. As determined by the same methods as in Example 2-1, the molecular weight thereof and the conjugation rate of MTX therein were about 340,000 and 2.0%, respectively.

This aqueous solution was purified by the same method as in Example 2-1 to provide a sterile aqueous solution of the title HA-MTX conjugate. As determined by the same methods as in Example 2-1, the molecular weight thereof and the conjugation rate of MTX therein were about 340,000 and 1.9%, respectively.

$^1$H-NMR (500 MHz, D$_2$O): δ1.83 (m), 2.01 (br.s), 2.12 (m), 2.52 (t), 2.69 (m), 2.95 (m), 3.34 (br.d), 3.49 (br.d), 3.57 (br.s), 3.70 (br.s), 3.83 (br.s), 4.16 (t), 4.45 (br.d), 4.54 (br.d), 4.87 (d), 4.96 (d), 6.66 (d), 6.88-7.09 (m), 7.72 (d), 8.68 (s)

The HA-MTX conjugates of the invention obtained in Examples 2-1 to 2-50 above are summarized in the following tables.

TABLE 1

| | Conjugation position (α/γ) | Linker containing peptide chain | Aqueous solution | | Sterile aqueous solution | |
|---|---|---|---|---|---|---|
| | | | Conjugation rate of MTX (%) | Molecular weight of conjugate (dalton) | Conjugation rate of MTX (%) | Molecular weight of conjugate (dalton) |
| Example 2-1 | α | -Phe-Phe-NH—C$_2$H$_4$—NH— | 2.1 | 1.95 × 10$^6$ | 2.1 | 1.86 × 10$^6$ |
| Example 2-2 | α | -Phe-Phe-NH—C$_2$H$_4$—NH— | 1.9 | 2.28 × 10$^6$ | 1.9 | 2.18 × 10$^6$ |
| Example 2-2' | α | -Phe-Phe-NH—C$_2$H$_4$—NH— | 2.2 | 2.19 × 10$^6$ | 2.3 | 2.06 × 10$^6$ |
| Example 2-3 | α | -Phe-Phe-NH—C$_2$H$_4$—NH— | 0.6 | 2.32 × 10$^6$ | 0.5 | 2.17 × 10$^6$ |
| Example 2-4 | α | -Phe-Phe-NH—C$_2$H$_4$—NH— | 1.1 | 2.32 × 10$^6$ | 1.1 | 2.23 × 10$^6$ |
| Example 2-5 | α | -Phe-Phe-NH—C$_2$H$_4$—NH— | 1.4 | 2.27 × 10$^6$ | 1.3 | 2.09 × 10$^6$ |
| Example 2-6 | α | -Phe-Phe-NH—C$_2$H$_4$—NH— | 3.9 | 2.05 × 10$^6$ | 3.8 | 1.91 × 10$^6$ |

TABLE 1-continued

|  | Conjugation position (α/γ) | Linker containing peptide chain | Aqueous solution | | Sterile aqueous solution | |
|---|---|---|---|---|---|---|
|  |  |  | Conjugation rate of MTX (%) | Molecular weight of conjugate (dalton) | Conjugation rate of MTX (%) | Molecular weight of conjugate (dalton) |
| Example 2-7 | α | -Phe-Phe-NH—$C_2H_4$—NH— | 4.5 | $1.97 \times 10^6$ | 4.4 | $1.74 \times 10^6$ |
| Example 2-8 | α | -Phe-Phe-NH—$C_{10}H_{20}O_3$—NH | 1.6 | $2.11 \times 10^6$ | 1.4 | $1.98 \times 10^6$ |
| Example 2-9 | α | -Phe-Phe-NH—$C_{10}H_{20}O_2$—NH— | 1.8 | $1.83 \times 10^6$ | 1.7 | $1.55 \times 10^6$ |
| Example 2-10 | α | -Phe-Phe-NH—$C_8H_{16}O_2$—NH— | 1.6 | $1.89 \times 10^6$ | 1.6 | $1.62 \times 10^6$ |
| Example 2-11 | α | -Phe-Phe-NH—$C_6H_{12}O_2$—NH— | 1.9 | $1.92 \times 10^6$ | 2.0 | $1.62 \times 10^6$ |
| Example 2-12 | α | -Phe-Phe-NH—$C_4H_8O$—NH— | 2.0 | $1.72 \times 10^6$ | 1.9 | $1.49 \times 10^6$ |
| Example 2-13 | α | -Phe-Phe-NH—$C_5H_{10}$—NH— | 1.4 | $2.14 \times 10^6$ | 1.2 | $1.96 \times 10^6$ |
| Example 2-14 | α | -Phe-Phe-Lys- | 1.4 | $1.89 \times 10^6$ | 1.4 | $1.72 \times 10^6$ |
| Example 2-15 | α | -Phe-Phe-NH—$C_{10}H_{20}O_3$—NH— | 1.4 | $0.83 \times 10^6$ | 1.4 | $0.80 \times 10^6$ |
| Example 2-16 | α | -Phe-Phe-NH—$C_{10}H_{20}O_3$—NH— | 0.5 | $0.83 \times 10^6$ | 0.5 | $0.81 \times 10^6$ |
| Example 2-17 | α | -Phe-Phe-NH—$C_{10}H_{20}O_3$—NH— | 3.4 | $0.77 \times 10^6$ | 3.4 | $0.76 \times 10^6$ |
| Example 2-18 | α | -Phe-Gly-NH—$C_{10}H_{20}O_3$—NH— | 1.5 | $1.99 \times 10^6$ | 1.4 | $1.86 \times 10^6$ |
| Example 2-19 | α | -Phe-Gly-NH—$C_{10}H_{20}O_2$—NH— | NT | NT | 1.8 | $1.44 \times 10^6$ |
| Example 2-20 | α | -Phe-Gly-NH—$C_8H_{16}O_2$—NH— | 1.6 | $1.73 \times 10^6$ | 1.6 | $1.50 \times 10^6$ |
| Example 2-21 | α | -Phe-Gly-NH—$C_6H_{12}O_2$—NH— | 2.3 | $1.50 \times 10^6$ | 2.3 | $1.39 \times 10^6$ |
| Example 2-22 | α | -Phe-Gly-NH—$C_4H_8O$—NH— | 2.0 | $1.56 \times 10^6$ | 2.2 | $1.40 \times 10^6$ |
| Example 2-23 | α | -Phe-Pro-NH—$C_{10}H_{20}O_3$—NH— | 1.6 | $1.66 \times 10^6$ | 1.6 | $1.52 \times 10^6$ |
| Example 2-24 | α | -Phe-βAla-NH—$C_{10}H_{20}O_3$—NH— | NT | NT | 1.5 | $1.52 \times 10^6$ |
| Example 2-25 | α | -Phe-βAla-NH—$C_2H_4$—NH— | 2.3 | $2.09 \times 10^6$ | 2.3 | $1.98 \times 10^6$ |
| Example 2-26 | α | -Phe-NH—$C_{10}H_{20}O_3$—NH— | 1.7 | $2.13 \times 10^6$ | 1.7 | $1.79 \times 10^6$ |
| Example 2-27 | α | -Ile-NH—$C_{10}H_{20}O_3$—NH— | 1.7 | $1.92 \times 10^6$ | 1.7 | $1.62 \times 10^6$ |
| Example 2-28 | α | -Ile-NH—$C_2H_4$—NH— | 2.1 | $2.31 \times 10^6$ | 2.1 | $2.02 \times 10^6$ |
| Example 2-29 | α | -Glu-NH—$C_{10}H_{20}O_3$—NH— | 1.5 | $2.01 \times 10^6$ | 1.5 | $1.83 \times 10^6$ |
| Example 2-30 | α | -Glu-NH—$C_2H_4$—NH— | 2.1 | $2.26 \times 10^6$ | 2.1 | $2.06 \times 10^6$ |
| Example 2-31 | α | -Tyr-NH—$C_{10}H_{20}O_3$—NH— | 1.6 | $1.90 \times 10^6$ | 1.7 | $1.76 \times 10^6$ |
| Example 2-32 | α | -Trp-NH—$C_{10}H_{20}O_3$—NH— | 1.9 | $1.87 \times 10^6$ | 1.9 | $1.39 \times 10^6$ |
| Example 2-33 | α/γ | -Ser-NH—$C_{10}H_{20}O_3$—NH— | 1.7 | $1.86 \times 10^6$ | 1.7 | $1.65 \times 10^6$ |
| Example 2-34 | α | -Leu-NH—$C_{10}H_{20}O_3$—NH— | 1.7 | $1.89 \times 10^6$ | 1.6 | $1.47 \times 10^6$ |
| Example 2-35 | α | -Val-NH—$C_{10}H_{20}O_3$—NH— | 1.7 | $1.87 \times 10^6$ | 1.7 | $1.56 \times 10^6$ |
| Example 2-36 | α | -His-NH—$C_{10}H_{20}O_3$—NH— | 1.2 | $1.91 \times 10^6$ | 1.2 | $1.62 \times 10^6$ |
| Example 2-37 | α | -Pro-NH—$C_{10}H_{20}O_3$—NH— | 1.5 | $1.67 \times 10^6$ | 1.6 | $1.52 \times 10^6$ |
| Example 2-38 | α | -βAla-NH—$C_{10}H_{20}O_3$—NH— | 1.7 | $1.91 \times 10^6$ | 1.7 | $1.43 \times 10^6$ |
| Example 2-39 | γ | -Phe-Phe-NH—$C_{10}H_{20}O_3$—NH— | 1.5 | $2.09 \times 10^6$ | 1.5 | $1.88 \times 10^6$ |
| Example 2-40 | γ | -Phe-Phe-NH—$C_6H_{12}O_2$—NH— | 2.1 | $1.89 \times 10^6$ | 2.0 | $1.76 \times 10^6$ |
| Example 2-41 | γ | -Phe-Phe-NH—$C_4H_8O$—NH— | 2.1 | $1.96 \times 10^6$ | 2.1 | $1.80 \times 10^6$ |
| Example 2-42 | γ | -Phe-Gly-NH—$C_{10}H_{20}O_3$—NH— | 1.4 | $1.90 \times 10^6$ | 1.5 | $1.72 \times 10^6$ |

TABLE 1-continued

| | Conjugation position (α/γ) | Linker containing peptide chain | Aqueous solution | | Sterile aqueous solution | |
|---|---|---|---|---|---|---|
| | | | Conjugation rate of MTX (%) | Molecular weight of conjugate (dalton) | Conjugation rate of MTX (%) | Molecular weight of conjugate (dalton) |
| Example 2-43 | γ | -Phe-NH—$C_{10}H_{20}O_3$—NH— | 1.7 | $1.87 \times 10^6$ | 1.7 | $1.65 \times 10^6$ |
| Example 2-44 | γ | -Glu-NH—$C_{10}H_{20}O_3$—NH— | 1.6 | $1.79 \times 10^6$ | 1.7 | $1.49 \times 10^6$ |
| Example 2-45 | α | -Dphe-DPhe-NH—$C_{10}H_{20}O_3$—NH— | 1.4 | $1.48 \times 10^6$ | 1.4 | $1.35 \times 10^6$ |
| Example 2-46 | γ | -Dphe-Dphe-NH—$C_{10}H_{20}O_3$—NH— | 1.4 | $1.60 \times 10^6$ | 1.3 | $1.41 \times 10^6$ |
| Example 2-47 | α/γ | -Asn-Phe-Phe-NH—$C_{10}H_{20}O_3$—NH— | 1.3 | $2.10 \times 10^6$ | 1.2 | $1.78 \times 10^6$ |
| Example 2-48 | α/γ | -Gly-Phe-Leu-Gly-NH—$C_{10}H_{20}O_3$—NH— | 1.4 | $2.06 \times 10^6$ | 1.3 | $1.85 \times 10^6$ |
| Example 2-49 | α | -Phe-Phe-NH—$C_{10}H_{20}O_3$—NH— | NT | NT | 1.1 | $0.33 \times 10^6$ |
| Example 2-50 | α | -Phe-Phe-NH—$C_2H_4$—NH— | 2.0 | $0.34 \times 10^6$ | 1.9 | $0.34 \times 10^6$ |

Experimental Example 1

Measurement of Viscoelasticity

The viscoelasticities of the sterile solutions of hyaluronic acids (molecular weights: 1,900,000 and 800,000) and the conjugates of Examples 2-1, 2-8, 2-18, 2-27, and 2-29 were measured at 37° C. using a cone 4 cm in diameter by a CSL500 stress-controlled rheometer (from Carri-Med Ltd.). FIG. 1 shows that the conjugates had viscoelasticities intermediate between those of the hyaluronic acids having molecular weights of 800,000 and 1,900,000.

Experimental Example 2

Anti-Proliferative Effect on Synovial Cells

An effect of the HA-MTX conjugates of the invention on cell proliferation induced by TNF-α stimulation was examined using human synovial cells (HFLS). The main lesion in rheumatoid arthritis (RA) occurs in the synovial tissue, and, as one of the features, it is known that synovial cells abnormally proliferate to form a granulation tissue (pannus) and thereby destroy the cartilage and bone of the joint. Secondary synovitis is also observed in osteoarthritis (OA). OA does not show such a marked change in the proliferation of synovial cells as that in RA, but synovitis becomes a cause of inflammatory symptoms such as hydrarthrosis, pain and heat, which are features of knee OA ("Hone, kansetsu Shikkan (Bone and joint diseases)" ed. Nobuyuki Miyasaka, 2003, Asakura Publishing Co., Ltd.). Thus, a compound inhibiting the proliferation of synovial cells stimulated by the inflammatory cytokine TNF-α suppresses the progression of the pathologic conditions of RA and OA and becomes a therapeutic drug therefor.

The sterile aqueous solutions of the HA-MTX conjugates in Example 2 (Table 2) were used as test substances. HFLS (CA40405, Lot Nos. 1413 and 1493) was purchased from Cell Applications Ins. for use.

HFLS was seeded at 5,000 cells/well on a 96-well plate (Falcon) and cultured for 3 hours in Iscove's modified Dulbecco's medium (IMDM) containing 5% FBS and 1× Antibiotic-Antimycotic (GIBOC). After cellular attachment, TNF-α (final concentration: 10 ng/mL) and each HA-MTX conjugate at each concentration was added, followed by cultivation for 5 days. Two days before the end of culture, was added 37 kBq/well of [$^3$H]-deoxyuridine in the cells (MORAVEK), followed by determining the uptake quantity (radioactivity) of [$^3$H]-deoxyuridine using a scintillation counter. Cells were recovered by unsticking them with 0.05% trypsin-0.2% EDTA.

Radioactivity determined in each of the experiments with each test substance was calculated as a relative value (% of control), using, as control, radioactivity in the group of cells cultured without adding any test substance. Since the concentration of a free carboxyl group is $2.49 \times 10^{-3}$ mol/L (1 g/401/L; 401 is the molecular weight of N-acetylglucosamine+glucuronic acid) for each 1 mg/mL of hyaluronic acid, the MTX concentration in each HA-MTX was calculated by multiplying the value by the conjugation rate of MTX. (For 1 mg/mL of HA-MTX conjugate with a conjugation rate of MTX of 1%, the concentration of MTX was $2.49 \times 10^{-5}$ mol/L) The value obtained was used to calculate the activity of inhibiting cell proliferation (IC$_{50}$ value) by a 4-parameter logistic method (analysis software: GraphPad Prism 3.02).

The IC$_{50}$ values of the HA-MTX conjugates in HFLS are shown in Table 2.

TABLE 2

Table 2: Suppressive effect on proliferation of human synovial cells stimulated by TNF-α

| | Conjugation position (α/γ) | Linker containing peptide chain | Conjugation rate of MTX (%) | Molecular weight of conjugate (dalton) | IC$_{50}$ (mol/L) |
|---|---|---|---|---|---|
| Example 2-1 | α | -Phe-Phe-NH—$C_2H_4$—NH— | 2.1 | $1.86 \times 10^6$ | 3.6E−07 |
| Example 2-2 | α | -Phe-Phe-NH—$C_2H_4$—NH— | 1.9 | $2.18 \times 10^6$ | 1.4E−07 |

TABLE 2-continued

Table 2: Suppressive effect on proliferation of human synovial cells stimulated by TNF-α

|  | Conjugation position (α/γ) | Linker containing peptide chain | Conjugation rate of MTX (%) | Molecular weight of conjugate (dalton) | $IC_{50}$ (mol/L) |
|---|---|---|---|---|---|
| Example 2-2' | α | -Phe-Phe-NH—$C_2H_4$—NH— | 2.3 | $2.06 \times 10^6$ | 7.2E−07 |
| Example 2-4 | α | -Phe-Phe-NH—$C_2H_4$—NH— | 1.1 | $2.23 \times 10^6$ | 1.1E−05 |
| Example 2-5 | α | -Phe-Phe-NH—$C_2H_4$—NH— | 1.3 | $2.09 \times 10^6$ | 1.1E−06 |
| Example 2-6 | α | -Phe-Phe-NH—$C_2H_4$—NH— | 3.8 | $1.91 \times 10^6$ | 9.1E−08 |
| Example 2-8 | α | -Phe-Phe-NH—$C_{10}H_{20}O_3$—NH | 1.4 | $1.98 \times 10^6$ | 8.4E−07 |
| Example 2-9 | α | -Phe-Phe-NH—$C_{10}H_{20}O_2$—NH— | 1.7 | $1.55 \times 10^6$ | 1.3E−06 |
| Example 2-10 | α | -Phe-Phe-NH—$C_8H_{16}O_2$—NH— | 1.6 | $1.62 \times 10^6$ | 1.2E−06 |
| Example 2-11 | α | -Phe-Phe-NH—$C_6H_{12}O_2$—NH— | 2.0 | $1.62 \times 10^6$ | 2.5E−07 |
| Example 2-12 | α | -Phe-Phe-NH—$C_4H_8O$—NH— | 1.9 | $1.49 \times 10^6$ | 3.0E−07 |
| Example 2-13 | α | -Phe-Phe-NH—$C_5H_{10}$—NH— | 1.2 | $1.96 \times 10^6$ | 1.5E−06 |
| Example 2-14 | α | -Phe-Phe-Lys- | 1.4 | $1.72 \times 10^6$ | 1.5E−05 |
| Example 2-15 | α | -Phe-Phe-NH—$C_{10}H_{20}O_3$—NH— | 1.4 | $0.80 \times 10^6$ | 4.8E−07 |
| Example 2-16 | α | -Phe-Phe-NH—$C_{10}H_{20}O_3$—NH— | 0.5 | $0.81 \times 10^6$ | 1.3E−05 |
| Example 2-17 | α | -Phe-Phe-NH—$C_{10}H_{20}O_3$—NH— | 3.4 | $0.76 \times 10^6$ | 1.3E−05 |
| Example 2-18 | α | -Phe-Gly-NH—$C_{10}H_{20}O_3$—NH— | 1.4 | $1.86 \times 10^6$ | 9.2E−06 |
| Example 2-19 | α | -Phe-Gly-NH—$C_{10}H_{20}O_2$—NH— | 1.8 | $1.44 \times 10^6$ | 5.4E−06 |
| Example 2-20 | α | -Phe-Gly-NH—$C_8H_{16}O_2$—NH— | 1.6 | $1.50 \times 10^6$ | 1.8E−06 |
| Example 2-21 | α | -Phe-Gly-NH—$C_6H_{12}O_2$—NH— | 2.3 | $1.39 \times 10^6$ | 8.3E−07 |
| Example 2-22 | α | -Phe-Gly-NH—$C_4H_8O$—NH— | 2.2 | $1.40 \times 10^6$ | 3.0E−06 |
| Example 2-23 | α | -Phe-Pro-NH—$C_{10}H_{20}O_3$—NH— | 1.6 | $1.52 \times 10^6$ | 1.2E−05 |
| Example 2-24 | α | -Phe-βAla-NH—$C_{10}H_{20}O_3$—NH— | 1.5 | $1.52 \times 10^6$ | 3.5E−06 |
| Example 2-25 | α | -Phe-βAla-NH—$C_2H_4$—NH— | 2.3 | $1.98 \times 10^6$ | 2.9E−07 |
| Example 2-26 | α | -Phe-NH—$C_{10}H_{20}O_3$—NH— | 1.7 | $1.79 \times 10^6$ | 1.7E−06 |
| Example 2-27 | α | -Ile-NH—$C_{10}H_{20}O_3$—NH— | 1.7 | $1.62 \times 10^6$ | 3.1E−06 |
| Example 2-28 | α | -Ile-NH—$C_2H_4$—NH— | 2.1 | $2.02 \times 10^6$ | 1.2E−05 |
| Example 2-29 | α | -Glu-NH—$C_{10}H_{20}O_3$—NH— | 1.5 | $1.83 \times 10^6$ | 8.4E−06 |
| Example 2-30 | α | -Glu-NH—$C_2H_4$—NH— | 2.1 | $2.06 \times 10^6$ | 5.4E−05 |
| Example 2-31 | α | -Tyr-NH—$C_{10}H_{20}O_3$—NH— | 1.7 | $1.76 \times 10^6$ | 7.0E−06 |
| Example 2-32 | α | -Trp-NH—$C_{10}H_{20}O_3$—NH— | 1.9 | $1.39 \times 10^6$ | 4.7E−06 |
| Example 2-33 | α | -Ser-NH—$C_{10}H_{20}O_3$—NH— | 1.7 | $1.65 \times 10^6$ | 3.6E−05 |
| Example 2-34 | α | -Leu-NH—$C_{10}H_{20}O_3$—NH— | 1.6 | $1.47 \times 10^6$ | 3.6E−06 |
| Example 2-35 | α | -Val-NH—$C_{10}H_{20}O_3$—NH— | 1.7 | $1.56 \times 10^6$ | 1.1E−05 |
| Example 2-36 | α | -His-NH—$C_{10}H_{20}O_3$—NH— | 1.2 | $1.62 \times 10^6$ | 1.7E−05 |
| Example 2-39 | γ | -Phe-Phe-NH—$C_{10}H_{20}O_3$—NH— | 1.5 | $1.88 \times 10^6$ | 3.2E−06 |
| Example 2-42 | γ | -Phe-Gly-NH—$C_{10}H_{20}O_3$—NH— | 1.5 | $1.72 \times 10^6$ | 1.4E−05 |
| Example 2-47 | α/γ | -Asn-Phe-Phe-NH—$C_{10}H_{20}O_3$—NH— | 1.2 | $1.78 \times 10^6$ | 1.1E−06 |
| Example 2-48 | α/γ | -Gly-Phe-Leu-Gly-NH—$C_{10}H_{20}O_3$—NH— | 1.3 | $1.85 \times 10^6$ | 1.3E−06 |
| Example 2-49 | α | -Phe-Phe-NH—$C_{10}H_{20}O_3$—NH— | 1.1 | $0.33 \times 10^6$ | 1.3E−05 |
| MTX alone | — | — |  | — | 5.5E−08 |

Table 2 demonstrates that each of the HA-TMX conjugates examined has a suppressive effect on the proliferation of HFLS cells enhanced by TNF-α stimulation.

Experimental Example 3

Suppressive Effect on Knee Joint Swelling in mBSA-Induced Monoarthritis Model

An in vivo synovitis-suppressing effect of each HA-MTX conjugate of the invention was assessed on the basis of a suppressive effect on knee joint swelling in a methylated bovine serum albumin (mBSA)-induced monoarthritis model of rat. Since the mBSA-induced arthritis model employed in this experimental example is widely used as an antigen-induced arthritis model, and known to develop synovitis (Sven E. Andersson, et al., The Journal of Rheumatology (1998) 25: 9, 1772-7), the in vivo knee joint swelling-suppressing effect observed in this model conceivably represents a synovitis-suppressing effect. The compounds of the invention suppressing synovitis in vivo are useful as therapeutic drugs for joint diseases accompanied by synovitis (RA, OA, and the like).

The animal used was the LEW/Crj rat (6-week old male, from Charles River Laboratories Japan, Inc.). Into the flank of the rat was subcutaneously injected 0.5 mL of an emulsion prepared from a 2 mg/mL mBSA (Calbiochem) aqueous solution and an equal amount of Freund's complete adjuvant (Difco) 21 and 14 days before inducing arthritis. The arthritis was induced by administering 50 μL of a 2 mg/mL mBSA aqueous solution into the right knee joint. The left knee joint was untreated, and served as control in each individual. Each test substance (sterile aqueous solution) and the control drug hyaluronic acid were each administered into the right knee joint in an amount of 50 μL 7 and 1 day before and 7 days after inducing arthritis.

The determination of knee joint swelling involved measuring the widths of both knee joints with calipers to define the left/right difference (right knee diameter-left knee diameter) as a knee joint swelling. The width of each knee joint was measured at a frequency of twice a week from immediately before inducing arthritis to two weeks later to calculate AUC (an abbreviation for Area Under the Curve; here, it means an area under a curve with time for the joint swelling) from the transition thereof with time. At each measurement, the mean and standard deviation of AUC were calculated to perform an unpaired t-test between each test substance-treated group and the HA-treated group, and significant difference was judged to be present if the probability level is less than 5%. Statistical analysis used SAS version 6.12 (SAS Institute Japan). In addition, the AUC of each test substance was calculated, using that in the HA-treated group as a control, as a relative value (% of control) therefor.

The results obtained by examining the efficacy of the HA-MTX conjugates of the invention by use of the above-described method are shown in Table 3.

TABLE 3

Table 3: Suppressive effect of HA-MTX conjugates on joint swelling in mBSA-induced monoarthritis model

| | Conjugation position ($\alpha/\gamma$) | Linker containing peptide chain | Conjugation rate of MTX (%) | Molecular weight of conjugate (dalton) | AUC (% of control) (mean ± SEM) | P value |
|---|---|---|---|---|---|---|
| Example 2-1 | $\alpha$ | -Phe-Phe-NH—$C_2H_4$—NH— | 2.1 | $1.86 \times 10^6$ | 48.5 ± 5.3 | P < 0.0001 |
| Example 2-2 | $\alpha$ | -Phe-Phe-NH—$C_2H_4$—NH— | 1.9 | $2.18 \times 10^6$ | 45.0 ± 6.8 | P < 0.0001 |
| Example 2-2' | $\alpha$ | -Phe-Phe-NH—$C_2H_4$—NH— | 2.3 | $2.06 \times 10^6$ | 65.5 ± 7.5 | P < 0.005 |
| Example 2-3 | $\alpha$ | -Phe-Phe-NH—$C_2H_4$—NH— | 0.5 | $2.17 \times 10^6$ | 76.2 ± 7.7 | P < 0.05 |
| Example 2-4 | $\alpha$ | -Phe-Phe-NH—$C_2H_4$—NH— | 1.1 | $2.23 \times 10^6$ | 69.0 ± 6.5 | P < 0.005 |
| Example 2-5 | $\alpha$ | -Phe-Phe-NH—$C_2H_4$—NH— | 1.3 | $2.09 \times 10^6$ | 51.7 ± 3.8 | P < 0.0001 |
| Example 2-6 | $\alpha$ | -Phe-Phe-NH—$C_2H_4$—NH— | 3.8 | $1.91 \times 10^6$ | 41.6 ± 7.6 | P < 0.0001 |
| Example 2-7 | $\alpha$ | -Phe-Phe-NH—$C_2H_4$—NH— | 4.4 | $1.74 \times 10^6$ | 46.5 ± 4.8 | P < 0.0001 |
| Example 2-8 | $\alpha$ | -Phe-Phe-NH—$C_{10}H_{20}O_3$—NH | 1.4 | $1.98 \times 10^6$ | 54.9 ± 7.2 | P < 0.005 |
| Example 2-10 | $\alpha$ | -Phe-Phe-NH—$C_8H_{16}O_2$—NH— | 1.6 | $1.62 \times 10^6$ | 63.7 ± 9.1 | P < 0.05 |
| Example 2-13 | $\alpha$ | -Phe-Phe-NH—$C_5H_{10}$—NH— | 1.2 | $1.96 \times 10^6$ | 60.5 ± 9.9 | P < 0.01 |
| Example 2-14 | $\alpha$ | -Phe-Phe-Lys- | 1.4 | $1.72 \times 10^6$ | 54.3 ± 7.4 | P < 0.0005 |
| Example 2-17 | $\alpha$ | -Phe-Phe-NH—$C_{10}H_{20}O_3$—NH— | 3.4 | $0.76 \times 10^6$ | 56.1 ± 8.2 | P < 0.01 |
| Example 2-18 | $\alpha$ | -Phe-Gly-NH—$C_{10}H_{20}O_3$—NH— | 1.4 | $1.86 \times 10^6$ | 61.5 ± 4.7 | P < 0.005 |
| Example 2-20 | $\alpha$ | -Phe-Gly-NH—$C_8H_{16}O_2$—NH— | 1.6 | $1.50 \times 10^6$ | 65.3 ± 9.6 | P < 0.01 |
| Example 2-21 | $\alpha$ | -Phe-Gly-NH—$C_6H_{12}O_2$—NH— | 2.3 | $1.39 \times 10^6$ | 47.4 ± 8.8 | P < 0.0005 |
| Example 2-27 | $\alpha$ | -Ile-NH—$C_{10}H_{20}O_3$—NH— | 1.7 | $1.62 \times 10^6$ | 75.1 ± 6.8 | P < 0.05 |
| Example 2-28 | $\alpha$ | -Ile-NH—$C_2H_4$—NH— | 2.1 | $2.02 \times 10^6$ | 63.5 ± 4.7 | P < 0.005 |
| Example 2-29 | $\alpha$ | -Glu-NH—$C_{10}H_{20}O_3$—NH— | 1.5 | $1.83 \times 10^6$ | 68.8 ± 6.7 | P < 0.005 |
| Example 2-30 | $\alpha$ | -Glu-NH—$C_2H_4$—NH— | 2.1 | $2.06 \times 10^6$ | 58.3 ± 7.4 | P < 0.005 |
| Example 2-31 | $\alpha$ | -Tyr-NH—$C_{10}H_{20}O_3$—NH— | 1.7 | $1.76 \times 10^6$ | 67.7 ± 6.2 | P < 0.005 |
| Example 2-38 | $\alpha$ | -$\beta$Ala-NH—$C_{10}H_{20}O_3$—NH— | 1.7 | $1.43 \times 10^6$ | 69.3 ± 4.2 | P < 0.001 |
| Example 2-41 | $\alpha$ | -Phe-Phe-NH—$C_4H_8O$—NH— | 2.1 | $1.80 \times 10^6$ | 67.1 ± 8.3 | P < 0.05 |
| Example 2-47 | $\alpha/\gamma$ | -Asn-Phe-Phe-NH—$C_{10}H_{20}O_3$—NH— | 1.2 | $1.78 \times 10^6$ | 42.1 ± 6.3 | P < 0.001 |
| Example 2-48 | $\alpha/\gamma$ | -Gly-Phe-Leu-Gly-NH—$C_{10}H_{20}O_3$—NH— | 1.3 | $1.85 \times 10^6$ | 58.8 ± 11.6 | P < 0.05 |

The results in Table 3 shows that each of the HA-MTX conjugates now examined significantly suppressed knee joint swelling in the arthritis model compared to that in the HA-treated group. When looking at an effect of the conjugation rate of MTX, which is conjugated with HA, it is suggested that the conjugation rate of MTX of 0.5 to 4.4% (Examples 1 to 7) significantly suppresses knee joint swelling in the arthritis model compared to that in a HA-treated group.

Experimental Example 4

Figure 2:
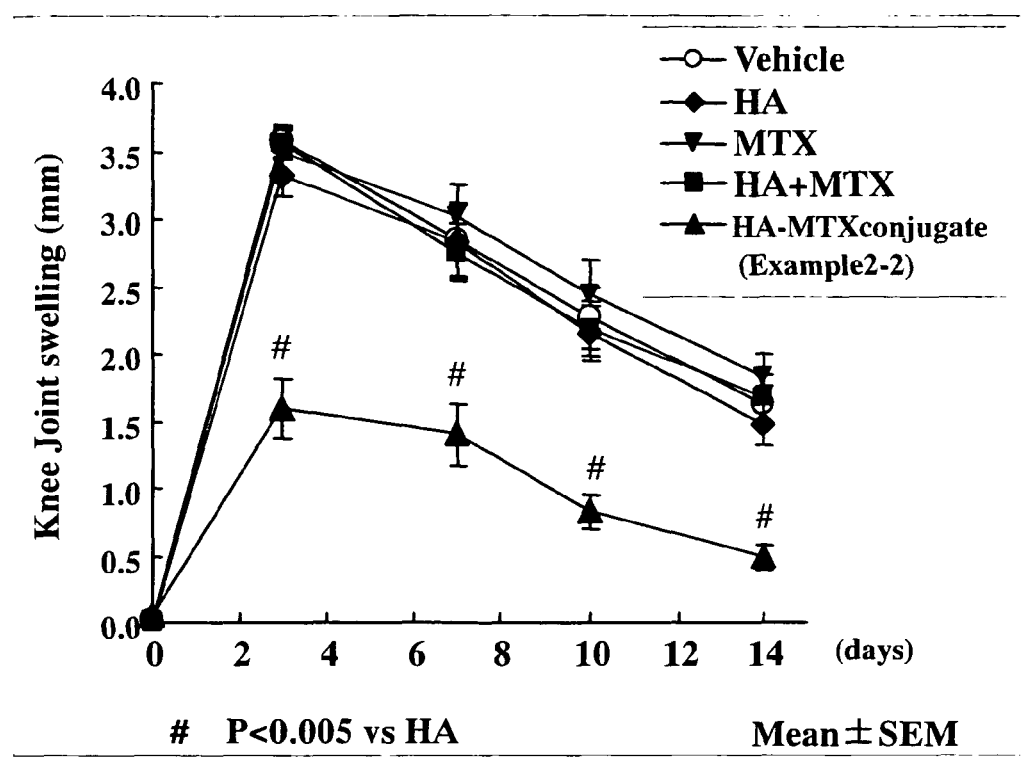
FIG. 2 is a graph showing the time course of knee joint swelling from immediately after injection of mBSA into the knee joint, in a test substance-treated group and control (HA and vehicle) groups.
Figure 3:
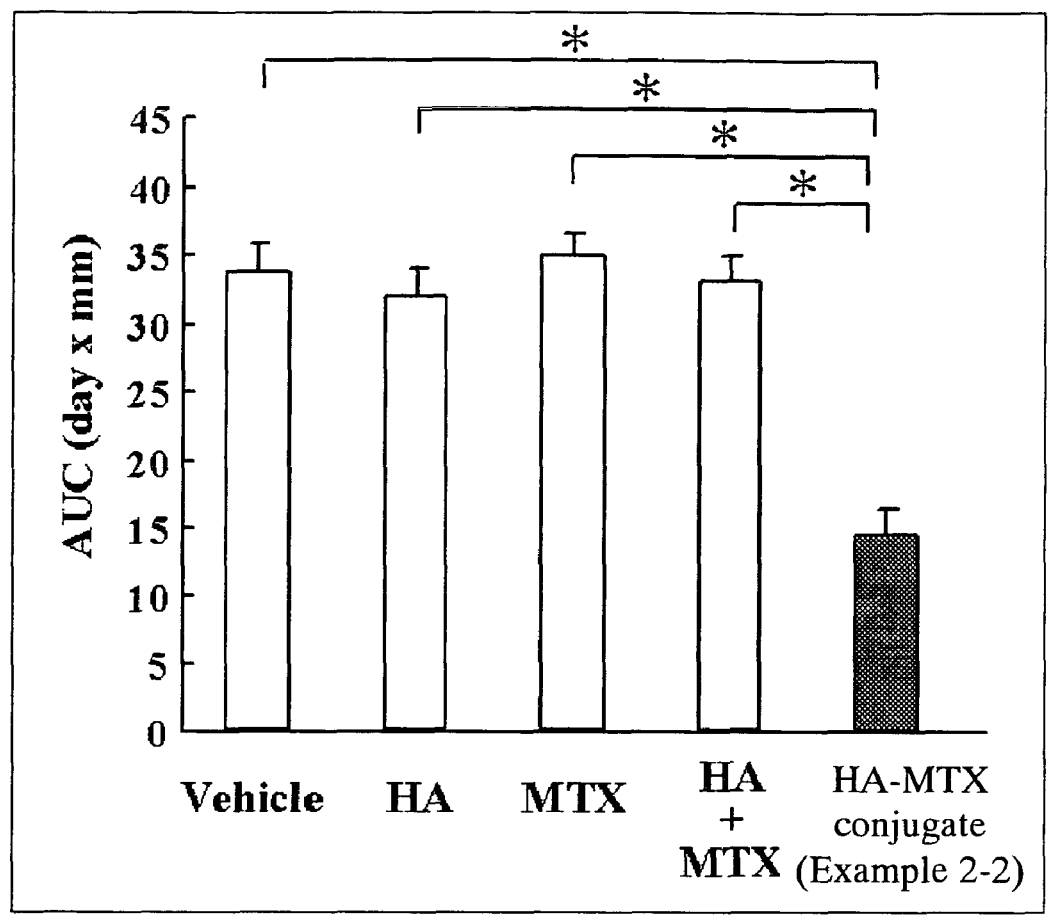
FIG. 3 is a graph showing the AUC of the graph for test substance-treated and control groups in FIG. 2.

To verify the usefulness of the HA-MTX conjugate of the invention, the suppressive effect on joint swelling was compared, in accordance with the method of Example 3, among: 1) a group treated with the HA-MTX conjugate (sterile aqueous solution) prepared in Example 2-2; 2) a group treated with a solution containing MTX of an amount equal to that of MTX contained in the HA-MTX conjugate; and 3) a group of treated with a mixture (HA+MTX) of MTX and hyaluronic acid (HA) of amounts equal to those contained in the conjugate. The transition of knee joint swelling with time in this test is shown in FIG. 2, and the AUC thereof in FIG. 3. The results in FIGS. 2 and 3 confirmed that the HA-MTX conjugate had a markedly strong suppressive effect on the joint swelling in the arthritis model compared to that of MTX alone or the mixture of MTX and HA. Therefore, it was demonstrated that the conjugation of MTX and HA significantly improved the joint swelling-suppressing effect of MTX.

From the above-described results, it was shown that the HA-MTX conjugate of the invention has a suppressive effect on in vitro proliferation of human synovial cells stimulated by TNF-α, and an alleviating effect on synovitis in the model developing arthritis in vivo. In the arthritis model, further, neither MTX alone nor the mixture of HA and MTX had a sufficient alleviating effect on synovitis, whereas the HA-MTX conjugate exerted a strong suppressive effect on synovitis.

Experimental Example 5

Effect on Collagen-Induced Arthritis Model

An in vivo synovitis-suppressing effect of the HA-MTX conjugate was evaluated in rat collagen-induced arthritis model (Kim et al., "Kansetsu geka (Articular surgery)" (1998) 17(2): 111-21) widely used as a model of rheumatoid arthritis (RA). The compound of the invention suppressing inflammation in this model will be useful for treating autoantigen-induced immune diseases represented by RA.

The animal used was the DA/Slc rat (Japan SLC Inc., 11-week old female). Bovine type II collagen (Collagen Gijutsu Kenshukai) was dissolved in a 0.01 mol/L acetic acid aqueous solution so as to provide a concentration of 1.5 mg/mL, to which an equal amount of Freund's incomplete adjuvant (Difco) was then added to make an emulsion. This emulsion was intradermaly administered in four places in the back of each rat at about 0.1 mL per place, or in a total amount of 0.4 mL to induce arthritis. Only into the right knee joint were administered 50 µL each of the test substance (sterile aqueous solution) and the control drugs hyaluronic acid (HA) and saline once every 5 days from the day of sensitization. The left knee joint was untreated. In addition, for a control for the pathologic model, saline was administered into the right knee joint of an (normal) animal in which arthritis was not induced.

A change in knee joint swelling was observed by measuring the widths of both knees with calipers to compare them with the widths in the normal group. The observation was carried out on the order of twice a week from immediately before inducing arthritis to 23 days later. At each measurement, the mean and standard error of the mean of knee joint widths was calculated to perform an unpaired t-test between the test substance-treated group and HA-treated group, and significant difference was judged to be present if the probability level is less than 5%. Statistical analysis used SAS version 8.02 (SAS Institute Japan).

The results obtained by examining the efficacy of the HA-MTX conjugates of the invention by use of the above-described method are shown in Table 4.

Figure 4:
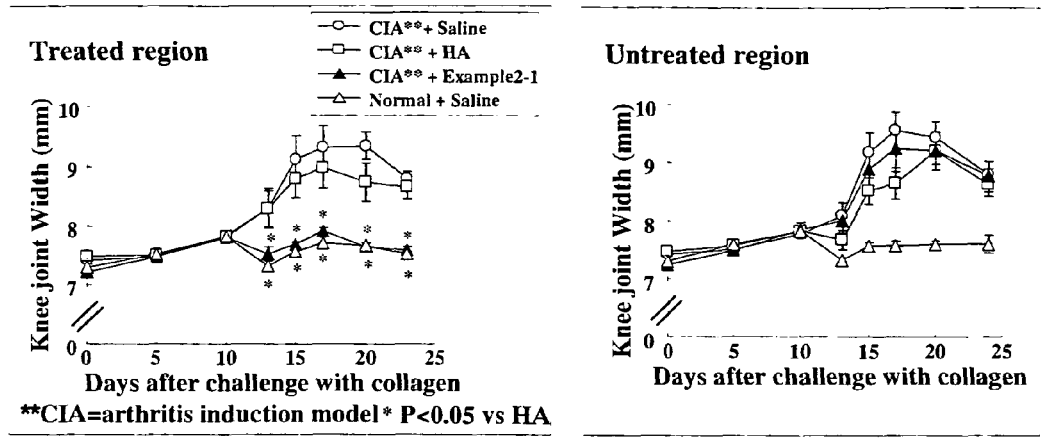
FIG. 4 is a set of graphs showing the time course of knee joint width from immediately after inducing collagen arthritis in a group treated with a substance from Example 1 and control (HA and saline) groups. The left figure shows the time course of the treated right knee joint, and the right figure shows the time course of the untreated left knee joint. In these graphs, the mean±standard error of the mean is shown.

The results in FIG. 4 shows that the HA-MTX conjugate of the invention significantly suppressed the width of the joint swelled by the induction of collagen-induced arthritis compared to that in the HA-treated group, and the transition of the width thereof with time was almost the same as that in the normal group. In addition, this effect was observed only in the region (right knee) into which the HA-MTX conjugate had been administered, and not seen in the untreated region (left knee). It was thus demonstrated that the present compound can exert an effect only in the region treated therewith.

Experimental Example 6

Suppressive Effect on Knee Joint Swelling in Collagenase-Induced Arthritis (OA) Model An in vivo synovitis-suppressing effect of the HA-MTX conjugate was evaluated in collagenase-induced OA model rats. The collagenase-induced OA model is a model in which inflammation has been induced within the knee joint by injecting collagenase into the knee joint to directly digest collagen in cartilage tissue. This model exhibits a histopathological change similar to the pathophysiology of human OA such as joint cargilage degeneration and synovitis and is useful for evaluating therapeutic drugs for OA (Takanori K, et al., Osteoarthritis and Cartilage (1998) δ: 177-86). Therefore, the compound of the invention suppressing inflammation in the model and inhibiting cartilage degeneration therein will be useful as a therapeutic drug for OA.

The animal used was the SD/Crj rat (6-week old male, from Charles River Laboratories Japan, Inc.). Into the articular cavity of the right knee was administered 50 µL of 1.5% collagenase (Sigma) solution to induce arthritis. The left knee joint was untreated to use as a control in each individual. Each test substance was administered into the right knee joint in an amount of 50 µL once a week from 7 and 1 day before inducing arthritis.

The determination of knee joint swelling involved measuring the widths of both knee joints with calipers to determine the left/right difference (right knee diameter-left knee diameter), which was defined as a knee joint swelling. The width of each knee joint was measured on the order of twice a week from immediately before inducing arthritis to 20 days later to calculate AUC from a graph showing the transition thereof with time. At each measurement, the mean and standard error of the mean of AUC were calculated to perform an unpaired t-test between each test substance-treated group and the HA-treated group, and significant difference was judged to be present if the probability level is less than 5%.

Figure 5:
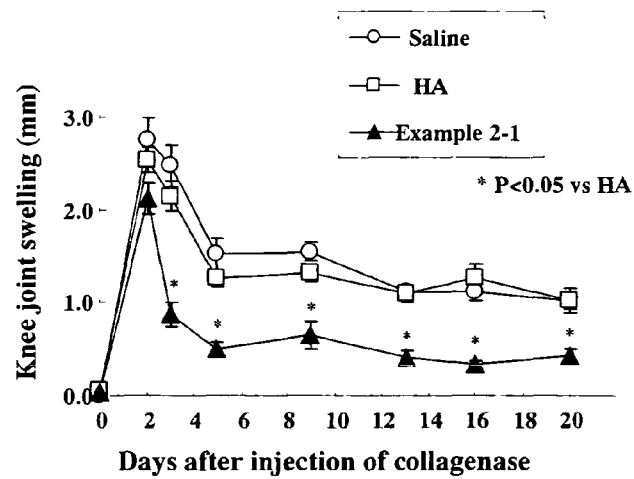
FIG. 5 is a graph showing the time course of knee joint swelling, from immediately after inducing the arthritis of a collagenase OA model to 20 days later, in a group treated with a substance from Example 1 and control (HA and saline) groups. In this graph, the mean±standard error of the mean is shown.

The results obtained by examining the efficacy of the HA-MTX conjugates of the invention by use of the above-described method are shown in FIG. 5 and Table 4. The transition of typical joint swelling with time for the HA-MTX conjugate is shown in FIG. 5, and the results about the test substances examined are indicated in Table 4.

TABLE 4

Suppressive effect of HA-MTX conjugates on knee joint swelling in collagenase-induced arthritis (OA) model

| | Conjugation position (α/γ) | Linker containing peptide chain | Conjugation rate of MTX (%) | Molecular weight of conjugate (dalton) | AUC (% of control) (mean ± SEM) | P value |
|---|---|---|---|---|---|---|
| Example 2-1 | α | -Phe-Phe-NH—$C_2H_4$—NH— | 2.1 | $1.86 \times 10^6$ | 45.7 ± 3.9 | P < 0.0001 |
| Example 2-2 | α | -Phe-Phe-NH—$C_2H_4$—NH— | 1.9 | $2.18 \times 10^6$ | 48.9 ± 3.7 | P < 0.001 |

TABLE 4-continued

Suppressive effect of HA-MTX conjugates on knee joint swelling in collagenase-induced arthritis (OA) model

| | Conjugation position (α/γ) | Linker containing peptide chain | Conjugation rate of MTX (%) | Molecular weight of conjugate (dalton) | AUC (% of control) (mean ± SEM) | P value |
|---|---|---|---|---|---|---|
| Example 2-8 | α | -Phe-Phe-NH—$C_{10}H_{20}O_3$—NH— | 1.4 | $1.98 \times 10^6$ | 54.8 ± 5.9 | P < 0.0001 |
| Example 2-18 | α | -Phe-Gly-NH—$C_{10}H_{20}O_3$—NH— | 1.4 | $1.86 \times 10^6$ | 65.9 ± 3.5 | P < 0.0001 |
| Example 2-27 | α | -Ile-NH—$C_{10}H_{20}O_3$—NH— | 1.7 | $1.62 \times 10^6$ | 82.6 ± 5.2 | P < 0.05 |

These results show that each of the HA-MTX conjugates now examined significantly suppressed joint swelling in the collagenase-induced arthritis model compared to that in the HA-treated group.

Experimental Example 7

Inhibitory Effect on Joint Cartilage Destruction in Collagenase-Induced Arthritis (OA) Model As described at the head of Example 6, a collagenase-induced OA model is known to be useful for evaluating a therapeutic drug for OA. Therefore, a compound suppressing inflammation in this model and inhibiting cartilage degeneration therein will be useful as a therapeutic drug for OA.

The animal used was the SD/Crj rat (6-week old male, from Charles River Laboratories Japan, Inc.). Into the articular cavity of the right knee was administered 50 μL of 1.5% collagenase (Sigma) solution to induce arthritis. The left knee joint was untreated to use as a control in each individual. A test substance, or saline as control was administered into the right knee joint in an amount of 50 μL once a week from 7 and 1 day before inducing arthritis.

To evaluate the degree of destruction of knee joint cartilage, the right knee joint was removed 28 days after inducing arthritis to photograph the image of degenerated joint cartilage in the medial malleolus of the crural bone using a scanning electron microscope (SEM). After the photographing, blinding was performed, followed by ranking the degree of joint cartilage degeneration from the SEM image of each individual. After fixing the data, the blinding was removed to calculate the ranking average of each group. The Wilcoxon rank sum test was performed between the saline-treated and test substance-treated groups, and significant difference was judged to be present if the probability level is less than 5%. Statistical analysis used SAS version 8.02 (SAS Institute Japan).

Figure 6:
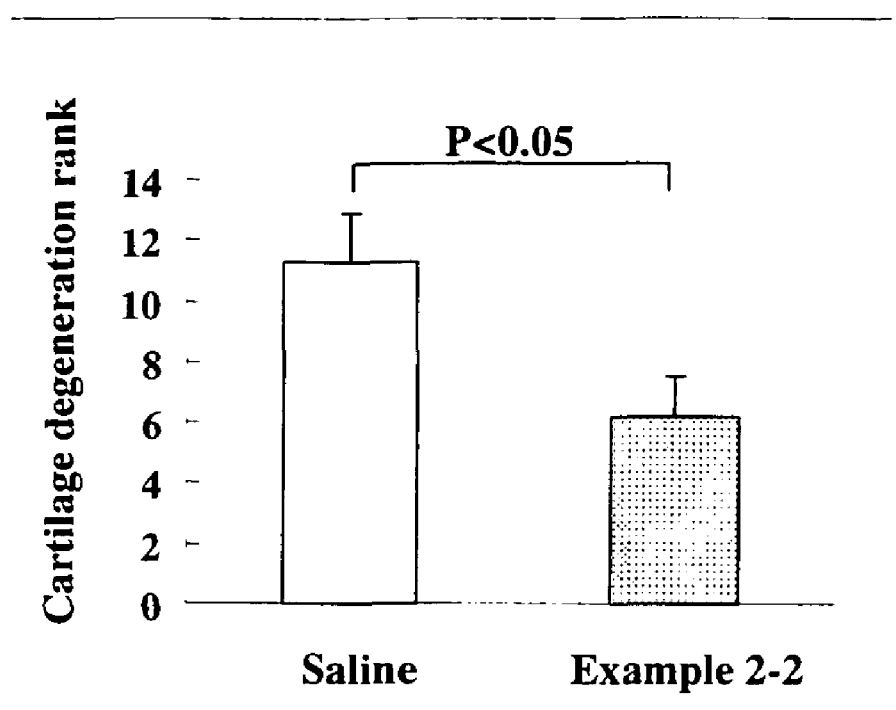
FIG. 6 is a graph showing the degree of cartilage degeneration in the medial tibial plateau of a collagenase OA model, in a group treated with a substance from Example 2-2 and a saline-treated group. In this graph, the mean±standard error of the mean is shown.

The results obtained by examining the efficacy of the HA-MTX conjugates of the invention by use of the above-described method are shown in FIG. 6.

The results in FIG. 6 show that the HA-MTX conjugate of the invention significantly inhibited cartilage degeneration in the collagenase-induced OA model compared to that in the saline-treated group. These results have demonstrated that the HA-MTX conjugate can suppress not only joint swelling but also the destruction of joint cartilage in an arthritis model. Therefore, the HA-MTX conjugate of the invention may be useful for treating joint diseases accompanied by joint cartilage degeneration or defect.

INDUSTRIAL APPLICABILITY

According to the HA-MTX conjugate of the invention, there is provided an excellent therapeutic drug for joint diseases, which has a non-conventional effect, has an aspect of HA as an intra-articular therapy and can safely exert a synovitis-suppressing effect of MTX only in the treated joint.

The invention claimed is:

1. A hyaluronic acid-methotrexate conjugate, wherein methotrexate is conjugated with a carboxyl group of hyaluronic acid, a hyaluronic acid derivative, or a salt thereof through a linker containing a peptide chain consisting of 1 to 8 amino acids; or a salt of the conjugate, wherein the linker containing a peptide chain and methotrexate conjugated with the linker is represented by formula (I') or (II'):

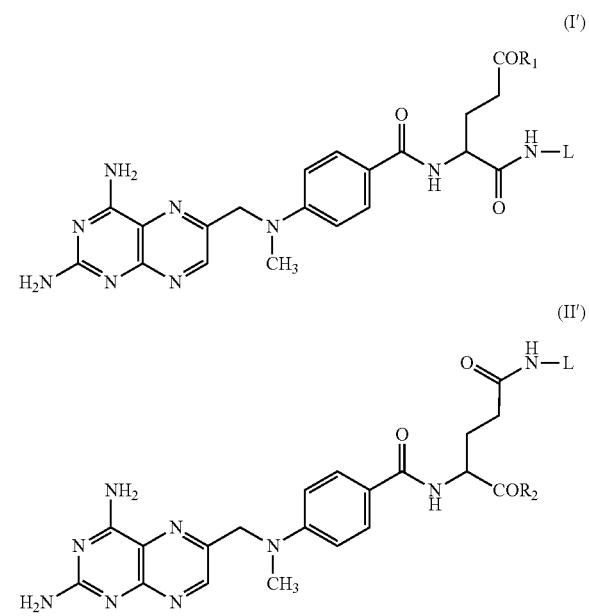

wherein $R_1$ and $R_2$ are each independently a hydroxy group, an amino group a $C_{1-6}$ alkoxy group, a $C_{1-6}$ alkylamino group, or a di-$C_{1-6}$ alkylamino group;

L is a linker represented by formula (x):

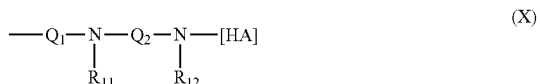

wherein $Q_1$ forms, together with —NH— binding thereto, a peptide chain consisting of 1 to 8 amino acids; residues of amino acids contained in the peptide chain are each independently optionally substituted or protected by one or more groups selected from the group consisting of a $C_{1-6}$ alkyl group, a $C_{1-6}$ alkylcarbonyl group, a $C_{1-6}$ alkoxycarbonyl group, a formyl group, a $C_{1-6}$ alkylsulfonyl group, and a $C_{6-10}$ arylsulfonyl group; amide bonds contained in the peptide chain are each independently optionally substituted on the nitrogen atom by one or more $C_{1-6}$ alkyl groups and/or $C_{1-6}$ alkylcarbonyl groups; and carboxyl groups contained in the residues are each independently optionally converted to an amide group optionally substituted by one or two $C_{1-6}$ alkyl groups;

$R_{11}$ and $R_{12}$ are each independently a hydrogen atom or a $C_{1-6}$ alkyl group;

$Q_2$ is $C_{2-20}$ alkylene, wherein the alkylene optionally has 1 to 5 oxygen atoms inserted thereinto and/or is optionally substituted by a carboxyl group or a $C_{1-6}$ alkoxycarbonyl group; and

[HA] represents the position of conjugation with the hyaluronic acid, derivative, or salt thereof, and the linker forms an amide bond with a carboxyl group contained in the hyaluronic acid, derivative or salt thereof.

2. The hyaluronic acid-methotrexate conjugate or the salt thereof according to claim 1, wherein the conjugation rate of methotrexate is 0.5% to 4.5% based on the total carboxyl groups of hyaluronic acid.

3. The hyaluronic acid-methotrexate conjugate or the salt thereof according to claim 1, wherein the molecular weight of hyaluronic acid is 600,000 daltons or more.

4. A pharmaceutical composition containing the hyaluronic acid-methotrexate conjugate or the salt thereof according to claim 1 as an active ingredient.

5. A therapeutic drug for joint diseases, containing the hyaluronic acid-methotrexate conjugate or the salt thereof according to claim 1 as an active ingredient.

6. The therapeutic drug for joint diseases according to claim 5, which is a topical preparation for administration into the joint.

7. A compound of formula (Va) or (Vb):

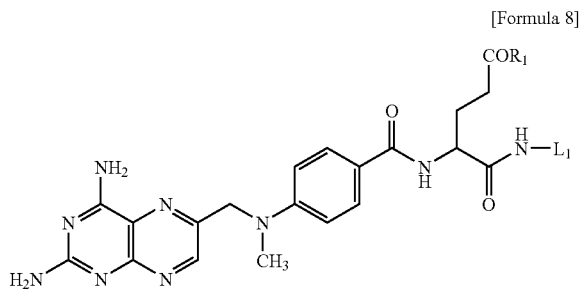

(Va)

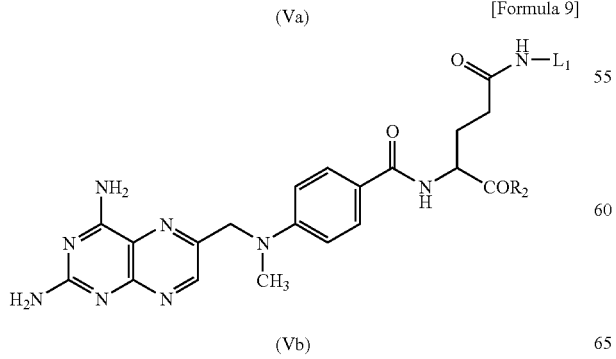

(Vb)

wherein $R_1$ and $R_2$ are each independently a hydroxy group, an amino group, a $C_{1-6}$ alkoxy group, a $C_{1-6}$ alkylamino group, or a di-$C_{1-6}$ alkylamino group;

$L_1$ is a linker represented by formula (X'):

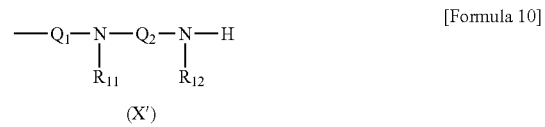

(X')

wherein $Q_1$ forms, together with —NH— binding thereto, a peptide chain consisting of 1 to 8 amino acids; residues of amino acids contained in the peptide chain are each independently optionally substituted or protected by one or more groups selected from the group consisting of a $C_{1-6}$ alkyl group, a $C_{1-6}$ alkylcarbonyl group, a $C_{1-6}$ alkoxycarbonyl group, a formyl group, a $C_{1-6}$ alkylsulfonyl group, and a $C_{6-10}$ arylsulfonyl group; amide bonds contained in the peptide chain are each independently optionally substituted on the nitrogen atom by one or more $C_{1-6}$ alkyl groups and/or $C_{1-6}$ alkylcarbonyl groups; and carboxyl groups contained in the residues are each independently optionally converted to an amide group optionally substituted by one or two $C_{1-6}$ alkyl groups;

$R_{11}$ and $R_{12}$ are each independently a hydrogen atom or a $C_{1-6}$ alkyl group; and $Q_2$ is a $C_{2-20}$ alkylene, wherein the alkylene optionally has 1 to 5 oxygen atoms inserted thereinto and/or is optionally substituted by a $C_{1-6}$ alkoxycarbonyl group.

8. A process for producing the hyaluronic acid-methotrexate conjugate or the salt thereof according to claim 1, which comprises the steps of reacting the compound of formula (Va) or (Vb) with hyaluronic acid, a hyaluronic acid derivative, or a salt thereof, and converting a carboxyl group of the hyaluronic acid, derivative, or salt thereof to an N-substituted amide group, wherein (Va) and (Vb) are as follows:

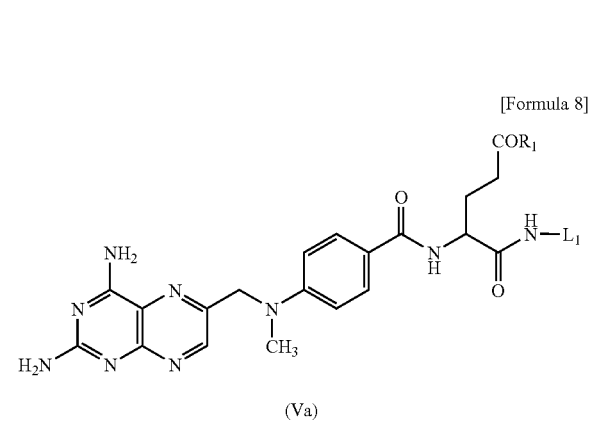

(Va)

[Formula 9]

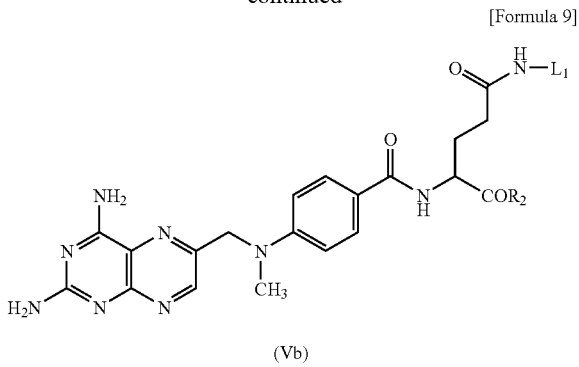

(Vb)

wherein $R_1$ and $R_2$ are each independently a hydroxy group, an amino group, a $C_{1-6}$ alkoxy group, a $C_{1-6}$ alkylamino group, or a di-$C_{1-6}$ alkylamino group;

$L_1$ is a linker represented by formula (X'):

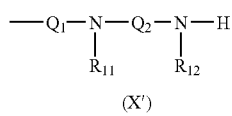

(X')

wherein $Q_1$ forms, together with —NH— binding thereto, a peptide chain consisting of 1 to 8 amino acids; residues of amino acids contained in the peptide chain are each independently optionally substituted or protected by one or more groups selected from the group consisting of a $C_{1-6}$ alkyl group, a $C_{1-6}$ alkylcarbonyl group, a $C_{1-6}$ alkoxycarbonyl group, a formyl group, a $C_{1-6}$ alkylsulfonyl group, and a $C_{6-10}$ arylsulfonyl group; amide bonds contained in the peptide chain are each independently optionally substituted on the nitrogen atom by one or more $C_{1-6}$ alkyl groups and/or $C_{1-6}$ alkylcarbonyl groups; and carboxyl groups contained in the residues are each independently optionally converted to an amide group optionally substituted by one or two $C_{1-6}$ alkyl groups;

$R_{11}$ and $R_{12}$ are each independently a hydrogen atom or a $C_{1-6}$ alkyl group; and $Q_2$ is a $C_{2-20}$ alkylene, wherein the alkylene optionally has 1 to 5 oxygen atoms inserted thereinto and/or is optionally substituted by a carboxyl group or a $C_{1-6}$ alkoxycarbonyl group.

9. The hyaluronic acid-methotrexate conjugate or the salt thereof according to claim 2, wherein the molecular weight of hyaluronic acid is 600,000 daltons or more.

\* \* \* \* \*